US009556421B2

(12) United States Patent
Granot et al.

(10) Patent No.: US 9,556,421 B2

(45) Date of Patent: Jan. 31, 2017

(54) USE OF FRUCTOKINASES AND SUCROSE SYNTHASES FOR INCREASING CELL WALL POLYMERS

(71) Applicant: The State of Israel—Ministry of Agriculture & Rural Development, Agricultural Research Organization (ARO) (Volcani Center) [IL/IL], Bet-Dagan (IL)

(72) Inventors: David Granot, Jerusalem (IL); Marcelo Ariel German, Lake Oswego, OR (US); Rakefet David-Schwartz, Givat Yeshayahu (IL); Nir Dai, Kiryat Ono (IL); Arthur Schaffer, Hashmonaim (IL); Marina Petrikov, Rishon Lezion (IL)

(73) Assignee: THE STATE OF ISRAEL, MINISTRY OF AGRICULTURE & RURAL DEVELOPMENT, AGRICULTURAL RESEARCH ORGANIZATION (ARO) (VOLCANI CENTER), Bet-Dagan (IL)

( * ) Notice: Subject to any disclaimer, the term of this patent is extended or adjusted under 35 U.S.C. 154(b) by 16 days.

(21) Appl. No.: 14/358,238

(22) PCT Filed: Nov. 15, 2012

(86) PCT No.: PCT/IB2012/056452

§ 371 (c)(1),
(2) Date: May 15, 2014

(87) PCT Pub. No.: WO2013/072868

PCT Pub. Date: May 23, 2013

(65) Prior Publication Data

US 2015/0322450 A1 Nov. 12, 2015

Related U.S. Application Data

(60) Provisional application No. 61/560,303, filed on Nov. 16, 2011.

(51) Int. Cl.

| | |
|---|---|
| ***C12N 15/82*** | (2006.01) |
| ***C12N 9/10*** | (2006.01) |
| ***C12N 9/12*** | (2006.01) |

(52) U.S. Cl.

CPC ........... *C12N 9/1062* (2013.01); *C12N 9/1205* (2013.01); *C12N 15/8201* (2013.01); *C12N 15/8245* (2013.01); *C12N 15/8246* (2013.01); *C12N 15/8261* (2013.01); *C12Y 207/01004* (2013.01)

(58) Field of Classification Search

None

See application file for complete search history.

(56) References Cited

U.S. PATENT DOCUMENTS

| | | | | |
|---|---|---|---|---|
| 6,031,154 A * | 2/2000 | Bennett | C12N 9/1205 435/101 |
| 2003/0135870 A1* | 7/2003 | Cheikh | C12N 15/8245 800/8 |

FOREIGN PATENT DOCUMENTS

| | | |
|---|---|---|
| WO | 2007116394 | 10/2007 |
| WO | 2007116394 A2 | 10/2007 |
| WO | 2010/062240 A1 | 6/2010 |

OTHER PUBLICATIONS

Coleman et al 2009, PNAS 31:13118-13123.*

Database NCBI [Online] Jun. 20, 1994 (Jun. 20, 1994). "Sucrose synthase [Solanum lycopersicum ]",Database accession number No. AAA34196. 17-19,22-25,43,44, Jun. 20, 1994 (Jun. 20, 1994).

German Marcelo A et al: "Suppression of Fructokinase Encoded by LeFRK2 in Tomato Stem Inhibits Growth and Causes Wilting of Young Leaves.", Plant Journal, vol. 34, No. 6, Jun. 2003, pp. 837-846, XP002739754, ISSN: 0960-7412.

Davies Howard V et al: "Modulation of Fructokinase Activity of Potato (*Solanum tuberosum*) Results in Substantial Shifts in Tuber Metabolism", Plant and Cell Physiology vol. 46, No. 7, Jul. 2005, pp. 1103-1115, XP002739755, ISSN:0032-0781.

Granot David: "Role of Tomato Hexose Kinases", Functional Plant Biology, CSIRO, AU, vol. 34, No. 6, Jan. 1, 2007, pp. 564-570, XP008176255, ISSN:1445-4408,DOI:10.1071/FP06207 [Retrived on Jun. 1, 2007].

Hauffe K D et al: "A Parsley 4CL-1 Promoter Fragment Specifies Complex Expressin Patterns in Transgenic Tobacco" Plant Cell, vol. 3, No. 5, 1991, pp. 435-444, XP002739756, ISSN: 1040-4651.

Hatton Diane et al: "Two Class of CIS Sequences Contribute to Tissue-Specific Expression of PAL2 Promoter in Transgenic Tobacco", Plant Journal, vol. 7, No. 6, 1995, pp. 859-876, XP002739757, ISSN: 0960-7412.

Inhibition of Fructokinase and Sucrose Synthase by Cytosolic Levels of Fructose in Young Tomato Fruit Undergoing Transient Starch Synthesis, Schaffer et al, Physiologia Phantarum, vol. 101, p. 800-806.

* cited by examiner

*Primary Examiner* — Brent Page

(74) *Attorney, Agent, or Firm* — Mark M. Friedman

(57) ABSTRACT

The invention relates to transgenic plants exhibiting increased cell wall content. In one embodiment, transgenic plants engineered to over-express fructokinase (FRK) or both FRK and sucrose synthase (SuSy) are provided. The FRK+SuSy double-transgenic plants of the invention consistently exhibit enhanced cell wall polymer deposition.

10 Claims, 3 Drawing Sheets

SEQUENCE LISTING

```
<160> NUMBER OF SEQ ID NOS: 40

<210> SEQ ID NO 1
<211> LENGTH: 806
<212> TYPE: PRT
<213> ORGANISM: Gossypium hirsutum
<300> PUBLICATION INFORMATION:
<308> DATABASE ACCESSION NUMBER: Q9XGB7
<309> DATABASE ENTRY DATE: 1999-11-01
<313> RELEVANT RESIDUES IN SEQ ID NO: (1)..(806)

<400> SEQUENCE: 1

Met Ala Glu Arg Ala Leu Thr Arg Val His Ser Leu Arg Glu Arg Leu
1               5                   10                  15

Asp Glu Thr Leu Leu Ala His Arg Asn Glu Ile Leu Ala Leu Leu Ser
            20                  25                  30

Arg Ile Glu Gly Lys Gly Lys Gly Ile Leu Gln His His Gln Ile Ile
        35                  40                  45
```

```
Leu Glu Phe Glu Ala Ile Pro Glu Glu Asn Arg Lys Lys Leu Ala Asn
    50                  55                  60

Gly Ala Phe Phe Glu Val Leu Lys Ala Ser Gln Glu Ala Ile Val Leu
65                  70                  75                  80

Pro Pro Trp Val Ala Leu Ala Val Arg Pro Arg Pro Gly Val Trp Glu
                85                  90                  95

Tyr Ile Arg Val Asn Val His Ala Leu Val Val Glu Glu Leu Thr Val
            100                 105                 110

Ala Glu Tyr Leu His Phe Lys Glu Glu Leu Val Asp Gly Ser Ser Asn
        115                 120                 125

Gly Asn Phe Val Leu Glu Leu Asp Phe Glu Pro Phe Asn Ser Ser Phe
    130                 135                 140

Pro Arg Pro Thr Leu Ser Lys Ser Ile Gly Asn Gly Val Glu Phe Leu
145                 150                 155                 160

Asn Arg His Leu Ser Ala Lys Leu Phe His Asp Lys Glu Ser Met His
                165                 170                 175

Pro Leu Leu Glu Phe Leu Arg Val His Cys His Lys Gly Lys Asn Met
            180                 185                 190

Met Leu Asn Asp Arg Ile Gln Asn Leu Asn Ala Leu Gln His Val Leu
        195                 200                 205

Arg Lys Ala Glu Glu Tyr Leu Gly Thr Leu Pro Pro Glu Thr Pro Cys
    210                 215                 220

Ala Glu Phe Glu His Arg Phe Gln Glu Ile Gly Leu Glu Arg Gly Trp
225                 230                 235                 240

Gly Asp Thr Ala Glu Arg Val Leu Glu Met Ile Gln Leu Leu Leu Asp
                245                 250                 255

Leu Leu Glu Ala Thr Asp Pro Cys Thr Leu Glu Lys Phe Leu Gly Arg
            260                 265                 270

Ile Pro Met Val Phe Asn Val Val Ile Leu Thr Pro His Gly Tyr Phe
        275                 280                 285

Ala Gln Asp Asn Val Leu Gly Tyr Pro Asp Thr Gly Gly Gln Val Val
    290                 295                 300

Tyr Ile Leu Asp Gln Val Arg Ala Leu Glu Asn Glu Met Leu Leu Arg
305                 310                 315                 320

Ile Lys Gln Gln Gly Leu Asn Ile Thr Pro Arg Ile Leu Ile Ile Thr
                325                 330                 335

Arg Leu Leu Pro Asp Ala Val Gly Thr Thr Cys Gly Gln Arg Leu Glu
            340                 345                 350

Lys Val Tyr Gly Thr Glu His Ser Asp Ile Leu Arg Val Pro Phe Arg
        355                 360                 365

Thr Glu Lys Gly Ile Val Arg Lys Trp Ile Ser Arg Phe Glu Lys Val
    370                 375                 380

Trp Pro Tyr Leu Glu Thr Tyr Thr Glu Asp Val Ala His Glu Ile Ser
385                 390                 395                 400

Lys Glu Leu His Gly Thr Pro Asp Leu Ile Ile Gly Asn Tyr Ser Asp
                405                 410                 415

Gly Asn Ile Val Ala Ser Leu Leu Ala His Lys Leu Gly Val Thr Gln
            420                 425                 430

Cys Thr Ile Ala His Ala Leu Glu Lys Thr Lys Tyr Pro Asp Ser Asp
        435                 440                 445

Ile Tyr Trp Lys Lys Leu Glu Asp Lys Tyr His Phe Ser Cys Gln Phe
    450                 455                 460
```

-continued

```
Thr Ala Asp Leu Phe Ala Met Asn His Thr Asp Phe Ile Ile Thr Ser
465                 470                 475                 480

Thr Phe Gln Glu Ile Ala Gly Ser Lys Asp Thr Val Gly Gln Tyr Glu
                485                 490                 495

Ser His Thr Ala Phe Thr Leu Pro Gly Leu Tyr Arg Val Val His Gly
            500                 505                 510

Ile Asp Val Phe Asp Pro Lys Phe Asn Ile Val Ser Pro Gly Ala Asp
        515                 520                 525

Met Glu Ile Tyr Phe Pro Tyr Thr Glu Glu Lys Arg Arg Leu Lys His
    530                 535                 540

Phe His Pro Glu Ile Glu Asp Leu Leu Tyr Thr Lys Val Glu Asn Glu
545                 550                 555                 560

Glu His Leu Cys Val Leu Asn Asp Arg Asn Lys Pro Ile Leu Phe Thr
                565                 570                 575

Met Pro Arg Leu Asp Arg Val Lys Asn Leu Thr Gly Leu Val Glu Trp
            580                 585                 590

Cys Gly Lys Asn Pro Lys Leu Arg Glu Leu Ala Asn Leu Val Val Val
        595                 600                 605

Gly Gly Asp Arg Arg Lys Glu Ser Lys Asp Leu Glu Glu Lys Ala Glu
    610                 615                 620

Met Lys Lys Met Phe Glu Leu Ile Asp Lys Tyr Asn Leu Asn Gly Gln
625                 630                 635                 640

Phe Arg Trp Ile Ser Ser Gln Met Asn Arg Ile Arg Asn Val Glu Leu
                645                 650                 655

Tyr Arg Tyr Ile Cys Asp Thr Lys Gly Ala Phe Val Gln Pro Ala Leu
            660                 665                 670

Tyr Glu Ala Phe Gly Leu Thr Val Val Glu Ala Met Thr Cys Gly Leu
        675                 680                 685

Pro Thr Phe Ala Thr Cys Asn Gly Gly Pro Ala Glu Ile Ile Val His
    690                 695                 700

Gly Lys Ser Gly Phe Asn Ile Asp Pro Tyr His Gly Asp Gln Ala Ala
705                 710                 715                 720

Asp Ile Leu Val Asp Phe Phe Glu Lys Cys Lys Lys Asp Pro Ser His
                725                 730                 735

Trp Asp Lys Ile Ser Gln Gly Gly Leu Lys Arg Ile Glu Glu Lys Tyr
            740                 745                 750

Thr Trp Lys Ile Tyr Ser Glu Arg Leu Leu Thr Leu Thr Gly Val Tyr
        755                 760                 765

Gly Phe Trp Lys His Val Ser Asn Leu Glu Arg Arg Glu Ser Arg Arg
    770                 775                 780

Tyr Leu Glu Met Phe Tyr Ala Leu Lys Tyr Arg Lys Leu Ala Glu Ser
785                 790                 795                 800

Val Pro Leu Ala Glu Glu
                805
```

<210> SEQ ID NO 2
<211> LENGTH: 347
<212> TYPE: PRT
<213> ORGANISM: Solanum lycopersicum
<300> PUBLICATION INFORMATION:
<308> DATABASE ACCESSION NUMBER: O04897
<309> DATABASE ENTRY DATE: 1997-01-07
<313> RELEVANT RESIDUES IN SEQ ID NO: (1)..(347)

<400> SEQUENCE: 2

```
Met Ala Gly Glu Ser Ile Ser Gly Asn Leu Lys Asp Leu Ser Leu Asn
```

-continued

```
1               5                   10                  15

Arg Asn Gly Ala Val Ser Lys Lys Ser His Leu Val Val Cys Phe Gly
            20                  25                  30

Glu Met Leu Ile Asp Phe Ile Pro Thr Val Ala Gly Val Ser Leu Ala
        35                  40                  45

Glu Ala Pro Ala Phe Glu Lys Ala Pro Gly Gly Ala Pro Ala Asn Val
    50                  55                  60

Ala Val Cys Ile Ser Lys Leu Gly Gly Ser Ser Ala Phe Ile Gly Lys
65                  70                  75                  80

Val Gly Asp Asp Glu Phe Gly Arg Met Leu Ala Asp Ile Leu Lys Gln
                85                  90                  95

Asn Asn Val Asp Asn Ser Gly Met Arg Phe Asp His Asp Ala Arg Thr
            100                 105                 110

Ala Leu Ala Phe Ile Thr Leu Thr Ala Glu Gly Glu Arg Glu Phe Val
        115                 120                 125

Phe Phe Arg Asn Pro Ser Ala Asp Met Leu Leu Arg Glu Ser Glu Leu
    130                 135                 140

Asp Val Asp Leu Ile Lys Lys Ala Thr Ile Phe His Tyr Gly Ser Ile
145                 150                 155                 160

Ser Leu Ile Asp Glu Pro Cys Arg Ser Thr His Leu Ala Ala Met Asp
                165                 170                 175

Ile Ala Lys Arg Ser Gly Ser Ile Leu Ser Tyr Asp Pro Asn Leu Arg
            180                 185                 190

Leu Pro Leu Trp Pro Ser Glu Asp Ala Ala Arg Ser Gly Ile Met Ser
        195                 200                 205

Val Trp Asn Leu Ala Asp Ile Ile Lys Ile Ser Glu Asp Glu Ile Ser
    210                 215                 220

Phe Leu Thr Gly Ala Asp Asp Pro Asn Asp Asp Glu Val Val Leu Lys
225                 230                 235                 240

Arg Leu Phe His Pro Asn Leu Lys Leu Leu Leu Val Thr Glu Gly Ser
                245                 250                 255

Ala Gly Cys Arg Tyr Tyr Thr Lys Glu Phe Lys Gly Arg Val Asn Ser
            260                 265                 270

Ile Lys Val Lys Ala Val Asp Thr Thr Gly Ala Gly Asp Ala Phe Thr
        275                 280                 285

Gly Gly Val Leu Lys Cys Leu Ala Ser Asp Ala Ser Leu Tyr Gln Asp
    290                 295                 300

Glu Lys Arg Leu Arg Glu Ala Ile Phe Phe Ala Asn Val Cys Ala Ala
305                 310                 315                 320

Leu Thr Val Thr Gly Arg Gly Gly Ile Pro Ser Leu Pro Thr Gln Asp
                325                 330                 335

Ala Val Arg Gln Thr Leu Ala Glu Val Thr Ala
            340                 345


<210> SEQ ID NO 3
<211> LENGTH: 328
<212> TYPE: PRT
<213> ORGANISM: Solanum lycopersicum
<300> PUBLICATION INFORMATION:
<308> DATABASE ACCESSION NUMBER: Q42896
<309> DATABASE ENTRY DATE: 2006-10-17
<313> RELEVANT RESIDUES IN SEQ ID NO: (1)..(328)

<400> SEQUENCE: 3

Met Ala Val Asn Gly Ala Ser Ser Ser Gly Leu Ile Val Ser Phe Gly
1               5                   10                  15
```

Glu Met Leu Ile Asp Phe Val Pro Thr Val Ser Gly Val Ser Leu Ala
20 25 30

Glu Ala Pro Gly Phe Leu Lys Ala Pro Gly Gly Ala Pro Ala Asn Val
35 40 45

Ala Ile Ala Val Thr Arg Leu Gly Gly Lys Ser Ala Phe Val Gly Lys
50 55 60

Leu Gly Asp Asp Glu Phe Gly His Met Leu Ala Gly Ile Leu Lys Thr
65 70 75 80

Asn Gly Val Gln Ala Glu Gly Ile Asn Phe Asp Lys Gly Ala Arg Thr
85 90 95

Ala Leu Ala Phe Val Thr Leu Arg Ala Asp Gly Glu Arg Glu Phe Met
100 105 110

Phe Tyr Arg Asn Pro Ser Ala Asp Met Leu Leu Thr Pro Ala Glu Leu
115 120 125

Asn Leu Asp Leu Ile Arg Ser Ala Lys Val Phe His Tyr Gly Ser Ile
130 135 140

Ser Leu Ile Val Glu Pro Cys Arg Ala Ala His Met Lys Ala Met Glu
145 150 155 160

Val Ala Lys Glu Ala Gly Ala Leu Leu Ser Tyr Asp Pro Asn Leu Arg
165 170 175

Leu Pro Leu Trp Pro Ser Ala Glu Glu Ala Lys Lys Gln Ile Lys Ser
180 185 190

Ile Trp Asp Ser Ala Asp Val Ile Lys Val Ser Asp Val Glu Leu Glu
195 200 205

Phe Leu Thr Gly Ser Asn Lys Ile Asp Asp Glu Ser Ala Met Ser Leu
210 215 220

Trp His Pro Asn Leu Lys Leu Leu Leu Val Thr Leu Gly Glu Lys Gly
225 230 235 240

Cys Asn Tyr Tyr Thr Lys Lys Phe His Gly Thr Val Gly Gly Phe His
245 250 255

Val Lys Thr Val Asp Thr Thr Gly Ala Gly Asp Ser Phe Val Gly Ala
260 265 270

Leu Leu Thr Lys Ile Val Asp Asp Gln Thr Ile Leu Glu Asp Glu Ala
275 280 285

Arg Leu Lys Glu Val Leu Arg Phe Ser Cys Ala Cys Gly Ala Ile Thr
290 295 300

Thr Thr Lys Lys Gly Ala Ile Pro Ala Leu Pro Thr Ala Ser Glu Ala
305 310 315 320

Leu Thr Leu Leu Lys Gly Gly Ala
325

<210> SEQ ID NO 4
<211> LENGTH: 319
<212> TYPE: PRT
<213> ORGANISM: Solanum tuberosum
<300> PUBLICATION INFORMATION:
<308> DATABASE ACCESSION NUMBER: P37829
<309> DATABASE ENTRY DATE: 1994-10-01
<313> RELEVANT RESIDUES IN SEQ ID NO: (1)..(319)

<400> SEQUENCE: 4

Met Ala Val Asn Gly Ser Ala Leu Ser Ser Gly Leu Ile Val Ser Phe
1 5 10 15

Gly Glu Met Leu Ile Asp Phe Val Pro Thr Val Ser Gly Val Ser Leu
20 25 30

```
Ala Glu Ala Pro Gly Phe Leu Lys Ala Pro Gly Gly Ala Pro Ala Asn
        35                  40                  45

Val Ala Ile Ala Val Thr Arg Leu Gly Gly Lys Ser Ala Phe Val Gly
    50                  55                  60

Lys Leu Gly Asp Asp Glu Phe Gly His Met Leu Ala Gly Ile Leu Lys
65                  70                  75                  80

Thr Asn Gly Val Gln Ala Asp Gly Ile Asn Phe Asp Lys Gly Ala Arg
                85                  90                  95

Thr Ala Leu Ala Phe Val Thr Leu Arg Ala Asp Gly Glu Arg Glu Phe
            100                 105                 110

Met Phe Tyr Arg Asn Pro Ser Ala Asp Met Leu Leu Thr Pro Asp Glu
        115                 120                 125

Leu Asn Leu Asp Leu Ile Arg Ser Ala Lys Val Phe His Tyr Gly Ser
    130                 135                 140

Ile Ser Leu Ile Val Glu Pro Cys Arg Ser Ala His Leu Lys Ala Met
145                 150                 155                 160

Glu Val Ala Lys Glu Ala Gly Ala Leu Leu Ser Tyr Asp Pro Asn Leu
                165                 170                 175

Arg Leu Pro Leu Trp Ser Ser Glu Ala Glu Ala Arg Lys Ala Ile Lys
            180                 185                 190

Val Ser Asp Val Glu Leu Glu Phe Leu Thr Gly Ser Asp Lys Ile Asp
        195                 200                 205

Asp Glu Ser Ala Met Ser Leu Trp His Pro Asn Leu Lys Leu Leu Leu
    210                 215                 220

Val Thr Leu Gly Glu Lys Gly Cys Asn Tyr Tyr Thr Lys Lys Phe His
225                 230                 235                 240

Gly Ser Val Gly Gly Phe His Val Lys Thr Val Asp Thr Thr Gly Ala
                245                 250                 255

Gly Asp Ser Phe Val Gly Ala Leu Leu Thr Lys Ile Val Asp Asp Gln
            260                 265                 270

Ala Ile Leu Glu Asp Glu Ala Arg Leu Lys Glu Val Leu Arg Phe Ser
        275                 280                 285

Cys Ala Cys Gly Ala Ile Thr Thr Thr Lys Lys Gly Ala Ile Pro Ala
    290                 295                 300

Leu Pro Thr Glu Ser Glu Ala Leu Thr Leu Leu Lys Gly Gly Ala
305                 310                 315


<210> SEQ ID NO 5
<211> LENGTH: 805
<212> TYPE: PRT
<213> ORGANISM: Solanum lycopersicum
<300> PUBLICATION INFORMATION:
<308> DATABASE ACCESSION NUMBER: P49037
<309> DATABASE ENTRY DATE: 1996-02-01
<313> RELEVANT RESIDUES IN SEQ ID NO: (1)..(805)

<400> SEQUENCE: 5

Met Ala Glu Arg Val Leu Thr Arg Val His Arg Leu Arg Glu Arg Val
1               5                   10                  15

Asp Ala Thr Leu Cys Ala His Arg Asn Glu Ile Leu Leu Phe Leu Ser
            20                  25                  30

Arg Ile Glu Ser His Gly Lys Gly Ile Leu Lys Pro His Glu Leu Leu
        35                  40                  45

Ala Glu Phe Asp Ala Ile Arg Gln Asp Asp Lys Asp Lys Leu Asn Glu
    50                  55                  60

His Ala Phe Glu Glu Leu Leu Lys Ser Thr Gln Glu Ala Ile Val Leu
```

-continued

```
65                  70                  75                  80

Pro Pro Trp Val Ala Leu Ala Ile Arg Leu Arg Pro Gly Val Trp Glu
                85                  90                  95

Tyr Val Arg Val Asn Val Asn Ala Leu Val Val Glu Glu Leu Ser Val
            100                 105                 110

Pro Glu Tyr Leu Gln Phe Lys Glu Glu Leu Val Asp Gly Ala Ser Asn
        115                 120                 125

Gly Asn Phe Val Leu Glu Leu Asp Phe Glu Pro Phe Thr Ala Ser Phe
    130                 135                 140

Pro Lys Pro Thr Leu Thr Lys Ser Ile Gly Asn Gly Val Glu Phe Leu
145                 150                 155                 160

Asn Arg His Leu Ser Ala Lys Met Phe His Asp Lys Glu Ser Met Ala
                165                 170                 175

Pro Leu Leu Glu Phe Leu Arg Ala His His Tyr Lys Gly Lys Thr Met
            180                 185                 190

Met Leu Asn Asp Arg Ile His Asn Ser Asn Thr Leu Gln Asn Val Leu
        195                 200                 205

Arg Lys Ala Glu Glu Tyr Leu Ile Met Leu Pro Pro Glu Thr Pro Phe
    210                 215                 220

Phe Glu Phe Glu His Lys Phe Gln Glu Ile Gly Leu Glu Lys Gly Trp
225                 230                 235                 240

Gly Asp Thr Ala Glu Arg Val Leu Glu Met Val Cys Met Leu Leu Asp
                245                 250                 255

Leu Leu Glu Ala Pro Asp Ser Cys Thr Leu Glu Lys Phe Leu Gly Arg
            260                 265                 270

Ile Pro Met Val Phe Asn Val Val Ile Leu Ser Pro His Gly Tyr Phe
        275                 280                 285

Ala Gln Glu Asn Val Leu Gly Tyr Pro Asp Thr Gly Gly Gln Val Val
    290                 295                 300

Tyr Ile Leu Asp Gln Val Pro Ala Leu Glu Arg Glu Met Leu Lys Arg
305                 310                 315                 320

Ile Lys Glu Gln Gly Leu Asp Ile Ile Pro Arg Ile Leu Ile Val Thr
                325                 330                 335

Arg Leu Leu Pro Asp Ala Val Gly Thr Thr Cys Gly Gln Arg Leu Glu
            340                 345                 350

Lys Val Tyr Gly Thr Glu His Ser His Ile Leu Arg Val Pro Phe Gly
        355                 360                 365

Thr Glu Lys Gly Ile Val Arg Lys Trp Ile Ser Arg Phe Glu Val Trp
    370                 375                 380

Pro Tyr Met Glu Thr Phe Ile Glu Asp Val Ala Lys Glu Ile Ser Ala
385                 390                 395                 400

Glu Leu Gln Ala Lys Pro Asp Leu Ile Ile Gly Asn Tyr Ser Glu Gly
                405                 410                 415

Asn Leu Ala Ala Ser Leu Leu Ala His Lys Leu Gly Val Thr Gln Cys
            420                 425                 430

Thr Ile Ala His Ala Leu Glu Lys Thr Lys Tyr Pro Asp Ser Asp Ile
        435                 440                 445

Tyr Trp Lys Lys Phe Asp Glu Lys Tyr His Phe Ser Ser Gln Phe Thr
    450                 455                 460

Ala Asp Leu Ile Ala Met Asn His Thr Asp Phe Ile Ile Thr Ser Thr
465                 470                 475                 480

Phe Gln Glu Ile Ala Gly Ser Lys Asp Thr Val Gly Gln Tyr Glu Ser
                485                 490                 495
```

-continued

```
His Met Ala Phe Thr Met Pro Gly Leu Tyr Arg Val Val His Gly Ile
            500                 505                 510

Asn Val Phe Asp Pro Lys Phe Asn Ile Val Ser Pro Gly Ala Asp Ile
        515                 520                 525

Asn Leu Tyr Phe Pro Tyr Ser Glu Ser Glu Lys Arg Leu Thr Ala Phe
    530                 535                 540

His Pro Glu Ile Asp Glu Leu Leu Tyr Ser Asp Val Glu Asn Asp Glu
545                 550                 555                 560

His Leu Cys Val Leu Lys Asp Arg Thr Lys Pro Ile Leu Phe Thr Met
                565                 570                 575

Ala Arg Leu Asp Arg Val Lys Asn Leu Thr Gly Leu Val Glu Trp Tyr
            580                 585                 590

Ala Lys Asn Pro Arg Leu Arg Gly Leu Val Asn Leu Val Val Val Gly
        595                 600                 605

Gly Asp Arg Arg Lys Glu Ser Lys Asp Leu Glu Glu Gln Ala Glu Met
    610                 615                 620

Lys Lys Met Tyr Glu Leu Ile Glu Thr His Asn Leu Asn Gly Gln Phe
625                 630                 635                 640

Arg Trp Ile Ser Ser Gln Met Asn Arg Val Arg Asn Gly Glu Leu Tyr
                645                 650                 655

Arg Tyr Ile Ala Asp Thr Lys Gly Ala Phe Val Gln Pro Ala Phe Tyr
            660                 665                 670

Glu Ala Phe Gly Leu Thr Val Val Glu Ala Met Thr Cys Gly Leu Pro
        675                 680                 685

Thr Phe Ala Thr Asn His Gly Gly Pro Ala Glu Ile Ile Val His Gly
    690                 695                 700

Lys Ser Gly Phe His Ile Asp Pro Tyr His Gly Glu Gln Ala Ala Asp
705                 710                 715                 720

Leu Leu Ala Asp Phe Phe Glu Lys Cys Lys Lys Glu Pro Ser His Trp
                725                 730                 735

Glu Thr Ile Ser Thr Gly Gly Leu Lys Arg Ile Gln Glu Lys Tyr Thr
            740                 745                 750

Trp Gln Ile Tyr Ser Glu Arg Leu Leu Thr Leu Ala Ala Val Tyr Gly
        755                 760                 765

Phe Trp Lys His Val Ser Lys Leu Asp Arg Leu Glu Ile Arg Arg Tyr
    770                 775                 780

Leu Glu Met Phe Tyr Ala Leu Lys Tyr Arg Lys Met Ala Glu Ala Val
785                 790                 795                 800

Pro Leu Ala Ala Glu
                805


<210> SEQ ID NO 6
<211> LENGTH: 805
<212> TYPE: PRT
<213> ORGANISM: Solanum lycopersicum
<300> PUBLICATION INFORMATION:
<308> DATABASE ACCESSION NUMBER: O82693
<309> DATABASE ENTRY DATE: 1998-11-01
<313> RELEVANT RESIDUES IN SEQ ID NO: (1)..(805)

<400> SEQUENCE: 6

Met Ala Glu Arg Val Leu Thr Arg Val His Arg Leu Arg Glu Arg Val
1               5                   10                  15

Asp Ala Thr Leu Ala Ala His Arg Asn Glu Ile Leu Leu Phe Leu Ser
            20                  25                  30
```

-continued

```
Arg Ile Glu Ser His Gly Lys Gly Ile Leu Lys Pro His Glu Leu Leu
        35                  40                  45

Ala Glu Phe Asp Ala Ile Arg Gln Asp Asp Lys Asp Lys Leu Asn Glu
    50                  55                  60

His Ala Phe Glu Glu Leu Leu Lys Ser Thr Gln Glu Ala Ile Val Leu
65                  70                  75                  80

Pro Pro Trp Val Ala Leu Ala Ile Arg Leu Arg Pro Gly Val Trp Glu
                85                  90                  95

Tyr Val Arg Val Asn Val Asn Ala Leu Val Val Glu Glu Leu Ser Val
            100                 105                 110

Pro Glu Tyr Leu Gln Phe Lys Glu Glu Leu Val Asp Gly Ala Ser Asn
        115                 120                 125

Gly Asn Phe Val Leu Glu Leu Asp Phe Glu Pro Phe Thr Ala Ser Phe
    130                 135                 140

Pro Lys Pro Thr Leu Thr Lys Ser Ile Gly Asn Gly Val Glu Phe Leu
145                 150                 155                 160

Asn Arg His Leu Ser Ala Lys Met Phe His Asp Lys Glu Ser Met Ala
                165                 170                 175

Pro Leu Leu Glu Phe Leu Arg Ala His His Tyr Lys Gly Lys Thr Met
            180                 185                 190

Met Leu Asn Asp Arg Ile His Asn Ser Asn Thr Leu Gln Asn Val Leu
        195                 200                 205

Arg Lys Ala Glu Glu Tyr Leu Ile Met Leu Pro Pro Glu Thr Pro Phe
    210                 215                 220

Phe Glu Phe Glu His Lys Phe Gln Glu Ile Gly Leu Glu Lys Gly Trp
225                 230                 235                 240

Gly Asp Thr Ala Glu Arg Val Leu Glu Met Val Cys Met Leu Leu Asp
                245                 250                 255

Leu Leu Glu Ala Pro Asp Ser Cys Thr Leu Glu Lys Phe Leu Gly Arg
            260                 265                 270

Ile Pro Met Val Phe Asn Val Val Ile Leu Ser Pro His Gly Tyr Leu
        275                 280                 285

Ala Gln Glu Asn Val Leu Gly Tyr Pro Asp Thr Gly Gly Gln Val Val
    290                 295                 300

Tyr Ile Leu Asp Gln Val Pro Ala Leu Glu Arg Glu Met Leu Lys Arg
305                 310                 315                 320

Ile Lys Glu Gln Gly Leu Asp Ile Ile Pro Arg Ile Leu Ile Val Thr
                325                 330                 335

Arg Leu Leu Pro Asp Ala Val Gly Thr Thr Cys Gly Gln Arg Leu Glu
            340                 345                 350

Lys Val Tyr Gly Thr Glu His Ser His Ile Leu Arg Val Pro Phe Arg
        355                 360                 365

Thr Glu Lys Gly Ile Val Arg Lys Trp Ile Ser Arg Phe Glu Val Trp
    370                 375                 380

Pro Tyr Met Glu Thr Phe Ile Glu Asp Val Ala Lys Glu Ile Ser Ala
385                 390                 395                 400

Glu Leu Gln Ala Lys Pro Asp Leu Ile Ile Gly Asn Tyr Ser Glu Gly
                405                 410                 415

Asn Leu Ala Ala Ser Leu Leu Ala His Lys Leu Gly Val Thr Gln Cys
            420                 425                 430

Thr Ile Ala His Ala Leu Glu Lys Thr Lys Tyr Pro Asp Ser Asp Ile
        435                 440                 445

Tyr Trp Lys Lys Phe Asp Glu Lys Tyr His Phe Ser Ser Gln Phe Thr
```

```
    450                 455                 460

Ala Asp Leu Ile Ala Met Asn His Thr Asp Phe Ile Ile Thr Ser Thr
465                 470                 475                 480

Phe Gln Glu Ile Ala Gly Ser Lys Asp Thr Val Gly Gln Tyr Glu Ser
                485                 490                 495

His Met Ala Phe Thr Met Pro Gly Leu Tyr Arg Val Val His Gly Ile
            500                 505                 510

Asn Val Phe Asp Pro Lys Phe Asn Ile Val Ser Pro Gly Ala Asp Ile
        515                 520                 525

Asn Leu Tyr Phe Pro Tyr Ser Glu Ser Glu Lys Arg Leu Thr Ala Phe
    530                 535                 540

His Pro Glu Ile Asp Glu Leu Leu Tyr Ser Asp Val Glu Asn Asp Asp
545                 550                 555                 560

His Leu Cys Val Leu Lys Asp Arg Thr Lys Pro Ile Leu Phe Thr Met
                565                 570                 575

Ala Arg Leu Asp Arg Val Lys Asn Leu Thr Gly Leu Val Glu Trp Tyr
            580                 585                 590

Ala Lys Asn Pro Arg Leu Arg Gly Leu Val Asn Leu Val Val Val Gly
        595                 600                 605

Gly Asp Arg Arg Lys Glu Ser Lys Asp Leu Glu Glu Gln Ala Glu Met
    610                 615                 620

Lys Lys Met Tyr Glu Leu Ile Glu Thr His Asn Leu Asn Gly Gln Phe
625                 630                 635                 640

Arg Trp Ile Ser Ser Gln Met Asn Arg Val Arg Asn Gly Glu Leu Tyr
                645                 650                 655

Arg Tyr Ile Ala Asp Thr Lys Gly Ala Phe Val Gln Pro Ala Phe Tyr
            660                 665                 670

Glu Ala Phe Gly Leu Thr Val Val Glu Ala Met Thr Cys Gly Leu Pro
        675                 680                 685

Thr Phe Ala Thr Asn His Gly Gly Pro Ala Glu Ile Ile Val His Gly
    690                 695                 700

Lys Ser Gly Phe His Ile Asp Pro Tyr His Gly Glu Gln Ala Ala Asp
705                 710                 715                 720

Leu Leu Ala Asp Phe Phe Glu Lys Cys Lys Lys Glu Pro Ser His Trp
                725                 730                 735

Glu Thr Ile Ser Thr Gly Gly Leu Lys Arg Ile Gln Glu Lys Tyr Thr
            740                 745                 750

Trp Gln Ile Tyr Ser Glu Arg Leu Leu Thr Leu Ala Ala Val Tyr Gly
        755                 760                 765

Phe Trp Lys His Val Ser Lys Leu Asp Arg Leu Glu Ile Arg Arg Tyr
    770                 775                 780

Leu Glu Met Phe Tyr Ala Leu Lys Tyr Arg Lys Met Ala Glu Ala Val
785                 790                 795                 800

Pro Leu Ala Ala Glu
                805


<210> SEQ ID NO 7
<211> LENGTH: 805
<212> TYPE: PRT
<213> ORGANISM: Solanum lycopersicum
<300> PUBLICATION INFORMATION:
<308> DATABASE ACCESSION NUMBER: O82691
<309> DATABASE ENTRY DATE: 1998-11-01
<313> RELEVANT RESIDUES IN SEQ ID NO: (1)..(805)

<400> SEQUENCE: 7
```

-continued

```
Met Ala Gln Arg Val Leu Thr Arg Val His Ser Leu Arg Glu Arg Leu
1               5                   10                  15

Asp Ala Thr Leu Asp Ala His Arg Asn Glu Ile Leu Leu Phe Leu Ser
            20                  25                  30

Arg Ile Glu Ser His Gly Lys Gly Ile Leu Lys Pro His Gln Leu Leu
        35                  40                  45

Ala Glu Phe Glu Ser Ile Gln Lys Glu Asp Lys Asp Lys Leu Asn Asp
    50                  55                  60

His Ala Phe Glu Glu Val Leu Lys Ser Thr Gln Glu Ala Ile Val Leu
65                  70                  75                  80

Pro Pro Trp Val Ala Leu Ala Ile Arg Leu Arg Pro Gly Val Trp Glu
                85                  90                  95

Tyr Val Arg Val Asn Val Asn Ala Leu Ser Val Glu Glu Leu Thr Val
            100                 105                 110

Pro Glu Phe Leu Gln Phe Lys Glu Glu Leu Val Asn Gly Thr Ser Ser
        115                 120                 125

Asp Asn Phe Val Leu Glu Leu Asp Phe Glu Pro Phe Thr Ala Ser Phe
    130                 135                 140

Pro Lys Pro Thr Leu Thr Lys Ser Ile Gly Asn Gly Val Glu Phe Leu
145                 150                 155                 160

Asn Arg His Leu Ser Ala Lys Met Phe His Asp Lys Glu Ser Met Thr
                165                 170                 175

Pro Leu Leu Glu Phe Leu Arg Val His His Tyr Asn Gly Lys Ser Met
            180                 185                 190

Met Leu Asn Asp Arg Ile Gln Asn Leu Tyr Thr Leu Gln Lys Val Leu
        195                 200                 205

Arg Lys Ala Glu Glu Tyr Leu Thr Thr Leu Ser Pro Glu Thr Ser Tyr
    210                 215                 220

Ser Ser Phe Glu His Lys Phe Gln Glu Ile Gly Leu Glu Arg Gly Trp
225                 230                 235                 240

Gly Asp Thr Ala Glu Arg Val Leu Glu Met Ile Cys Met Leu Leu Asp
                245                 250                 255

Leu Leu Glu Ala Pro Asp Ser Cys Thr Leu Glu Lys Phe Leu Ser Arg
            260                 265                 270

Ile Pro Met Val Phe Asn Val Val Ile Pro Ser Pro His Gly Tyr Phe
        275                 280                 285

Ala Gln Glu Asn Val Leu Gly Tyr Pro Asp Thr Gly Gly Gln Val Val
    290                 295                 300

Tyr Ile Leu Asp Gln Val Pro Ala Leu Glu Arg Glu Met Leu Lys Arg
305                 310                 315                 320

Ile Lys Glu Gln Gly Leu Asp Ile Lys Pro Arg Ile Leu Ile Val Thr
                325                 330                 335

Arg Leu Leu Pro Asp Ala Val Gly Thr Thr Cys Gly Gln Arg Leu Glu
            340                 345                 350

Lys Val Phe Gly Thr Glu His Ser His Ile Leu Arg Val Pro Phe Arg
        355                 360                 365

Thr Glu Lys Gly Ile Val Arg Lys Trp Ile Ser Arg Phe Glu Val Trp
    370                 375                 380

Pro Tyr Met Glu Thr Phe Ile Glu Asp Val Gly Lys Glu Ile Thr Ala
385                 390                 395                 400

Glu Leu Gln Ala Lys Pro Asp Leu Ile Ile Gly Asn Tyr Ser Glu Gly
                405                 410                 415
```

-continued

```
Asn Leu Ala Ala Ser Leu Leu Ala His Lys Leu Gly Val Thr Gln Cys
            420                 425                 430

Thr Ile Ala His Ala Leu Glu Lys Thr Lys Tyr Pro Asp Ser Asp Ile
        435                 440                 445

Tyr Leu Asn Lys Phe Asp Glu Lys Tyr His Phe Ser Ala Gln Phe Thr
    450                 455                 460

Ala Asp Leu Ile Ala Met Asn His Thr Asp Phe Ile Ile Thr Ser Thr
465                 470                 475                 480

Phe Gln Glu Ile Ala Gly Ser Lys Asp Thr Val Gly Gln Tyr Glu Ser
                485                 490                 495

His Met Ala Phe Thr Met Pro Gly Leu Tyr Arg Val Val His Gly Ile
            500                 505                 510

Asp Val Phe Asp Pro Lys Phe Asn Ile Val Ser Pro Gly Ala Asp Val
        515                 520                 525

Asn Leu Tyr Phe Pro Tyr Ser Glu Lys Glu Lys Arg Leu Thr Thr Phe
    530                 535                 540

His Pro Glu Ile Glu Asp Leu Leu Phe Ser Asp Val Glu Asn Glu Glu
545                 550                 555                 560

His Leu Cys Val Leu Lys Asp Arg Asn Lys Pro Ile Ile Phe Thr Met
                565                 570                 575

Ala Arg Leu Asp Arg Val Lys Asn Leu Thr Gly Leu Val Glu Trp Tyr
            580                 585                 590

Ala Lys Asn Pro Arg Leu Arg Glu Leu Val Asn Leu Val Val Val Gly
        595                 600                 605

Gly Asp Arg Arg Lys Glu Ser Lys Asp Leu Glu Glu Gln Ala Glu Met
    610                 615                 620

Lys Lys Met Tyr Glu Leu Ile Lys Thr His Asn Leu Asn Gly Gln Phe
625                 630                 635                 640

Arg Trp Ile Ser Ser Gln Met Asn Arg Val Arg Asn Gly Glu Leu Tyr
                645                 650                 655

Arg Tyr Ile Ala Asp Thr Arg Gly Ala Phe Val Gln Pro Ala Phe Tyr
            660                 665                 670

Glu Ala Phe Gly Leu Thr Val Val Glu Ala Met Ser Cys Gly Leu Pro
        675                 680                 685

Thr Phe Ala Thr Asn Gln Gly Gly Pro Ala Glu Ile Ile Val His Gly
    690                 695                 700

Lys Ser Gly Phe Gln Ile Asp Pro Tyr His Gly Glu Gln Ala Ala Asp
705                 710                 715                 720

Leu Leu Ala Glu Phe Phe Glu Lys Cys Lys Val Asp Pro Ser His Trp
                725                 730                 735

Glu Ala Ile Ser Lys Gly Gly Leu Lys Arg Ile Gln Glu Lys Tyr Thr
            740                 745                 750

Trp Gln Ile Tyr Ser Asp Arg Leu Leu Thr Leu Ala Ala Val Tyr Gly
        755                 760                 765

Phe Trp Lys His Val Ser Lys Leu Asp Arg Leu Glu Ile Arg Arg Tyr
    770                 775                 780

Leu Glu Met Phe Tyr Ala Leu Lys Phe Arg Lys Leu Ala Glu Leu Val
785                 790                 795                 800

Pro Leu Ala Val Glu
                805
```

<210> SEQ ID NO 8
<211> LENGTH: 812
<212> TYPE: PRT

```
<213> ORGANISM: Solanum lycopersicum
<300> PUBLICATION INFORMATION:
<308> DATABASE ACCESSION NUMBER: ADM47609.1
<309> DATABASE ENTRY DATE: 2010-09-01
<313> RELEVANT RESIDUES IN SEQ ID NO: (1)..(812)

<400> SEQUENCE: 8

Met Ser Asn Pro Lys Leu Ser Arg Ile Pro Ser Met Arg Glu Arg Val
1               5                   10                  15

Glu Asp Thr Leu Ser Ala His Arg Asn Gln Leu Val Ala Leu Leu Ser
            20                  25                  30

Arg Tyr Val Ala Gln Gly Lys Gly Ile Leu Gln Pro His His Leu Ile
        35                  40                  45

Asp Glu Leu Asn Asn Ala Val Cys Asp Asp Thr Ala Cys Glu Lys Leu
    50                  55                  60

Lys Glu Gly Pro Phe Cys Glu Ile Leu Lys Ser Thr Gln Glu Ala Ile
65                  70                  75                  80

Val Leu Pro Pro Phe Val Ala Ile Ala Val Arg Pro Arg Pro Gly Val
                85                  90                  95

Trp Glu Tyr Val Arg Val Asn Val Tyr Asp Leu Ser Val Glu Gln Leu
            100                 105                 110

Thr Val Pro Glu Tyr Leu Arg Phe Lys Glu Glu Leu Val Asp Gly Glu
        115                 120                 125

Asp His Asn His Leu Phe Val Leu Glu Leu Asp Phe Glu Pro Phe Asn
    130                 135                 140

Ala Ser Val Pro Arg Pro Ser Arg Ser Ser Ser Ile Gly Asn Gly Val
145                 150                 155                 160

Gln Phe Leu Asn Arg His Leu Ser Ser Asn Met Phe Arg Ser Asn Glu
                165                 170                 175

Ser Leu Asp Pro Leu Leu Asp Phe Leu Arg Gly His Asn His Lys Gly
            180                 185                 190

Asn Val Leu Met Leu Asn Glu Arg Ile Gln Arg Ile Ser Arg Leu Glu
        195                 200                 205

Ser Ser Leu Asn Lys Ala Asp Asp Tyr Leu Ser Lys Leu Pro Pro Asp
    210                 215                 220

Thr Pro Tyr Thr Asp Phe Glu Tyr Ala Leu Gln Glu Met Gly Phe Glu
225                 230                 235                 240

Lys Gly Trp Gly Asp Thr Ala Asn Arg Val Leu Glu Thr Met His Leu
                245                 250                 255

Leu Ser Asp Ile Leu Gln Ala Pro Asp Pro Ser Thr Leu Glu Thr Phe
            260                 265                 270

Leu Gly Arg Leu Pro Met Val Phe Asn Val Val Ile Leu Ser Pro His
        275                 280                 285

Gly Tyr Phe Gly Gln Ala Asn Val Leu Gly Leu Pro Asp Thr Gly Gly
    290                 295                 300

Gln Val Val Tyr Ile Leu Asp Gln Val Arg Ala Leu Glu Ala Glu Met
305                 310                 315                 320

Leu Leu Arg Ile Lys Gln Gln Gly Leu Asn Phe Lys Pro Arg Ile Leu
                325                 330                 335

Val Val Thr Arg Leu Ile Pro Asp Ala Lys Gly Thr Thr Cys Asn Gln
            340                 345                 350

Arg Leu Glu Arg Ile Ser Gly Thr Glu Tyr Ser His Ile Leu Arg Val
        355                 360                 365

Pro Phe Arg Thr Glu Asn Gly Ile Leu His Lys Trp Ile Ser Arg Phe
    370                 375                 380
```

-continued

```
Asp Val Trp Pro Tyr Leu Glu Lys Phe Thr Glu Asp Val Ala Gly Glu
385                 390                 395                 400

Met Ser Ala Glu Leu Gln Gly Val Pro Asp Leu Ile Ile Gly Asn Tyr
                405                 410                 415

Ser Asp Gly Asn Leu Val Ala Ser Leu Leu Ala Tyr Lys Met Gly Ile
            420                 425                 430

Thr Gln Cys Thr Ile Ala His Ala Leu Glu Lys Thr Lys Tyr Pro Asp
        435                 440                 445

Ser Asp Ile Tyr Trp Lys Lys Phe Glu Glu Lys Tyr His Phe Ser Cys
    450                 455                 460

Gln Phe Thr Ala Asp Leu Leu Ser Met Asn His Ser Asp Phe Ile Ile
465                 470                 475                 480

Thr Ser Thr Tyr Gln Glu Ile Ala Gly Thr Lys Asn Thr Val Gly Gln
                485                 490                 495

Tyr Glu Ser His Thr Ala Phe Thr Leu Pro Gly Leu Tyr Arg Val Val
            500                 505                 510

His Gly Ile Asp Val Phe Asp Pro Lys Phe Asn Ile Val Ser Pro Gly
        515                 520                 525

Ala Asp Met Thr Ile Tyr Phe Pro Tyr Phe Asp Lys Glu Lys Arg Leu
    530                 535                 540

Thr Ser Leu His Pro Ser Ile Glu Lys Leu Leu Phe Asp Pro Glu Gln
545                 550                 555                 560

Asn Glu Val His Ile Gly Ser Leu Asn Asp Gln Ser Lys Pro Ile Ile
                565                 570                 575

Phe Ser Met Ala Arg Leu Asp Arg Val Lys Asn Ile Thr Gly Leu Val
            580                 585                 590

Glu Cys Tyr Ala Lys Asn Ala Thr Leu Arg Glu Leu Ala Asn Leu Val
        595                 600                 605

Val Val Ala Gly Tyr Asn Asp Val Lys Lys Ser Asn Asp Arg Glu Glu
    610                 615                 620

Ile Ala Glu Ile Glu Lys Met His Ala Leu Met Lys Glu His Asn Leu
625                 630                 635                 640

Asp Gly Gln Phe Arg Trp Ile Ser Ala Gln Met Asn Arg Ala Arg Asn
                645                 650                 655

Gly Glu Leu Tyr Arg Tyr Ile Ala Asp Lys Arg Gly Ile Phe Val Gln
            660                 665                 670

Pro Ala Tyr Tyr Glu Ala Phe Gly Leu Thr Val Val Glu Ala Met Thr
        675                 680                 685

Cys Gly Leu Pro Thr Phe Ala Thr Cys His Gly Gly Pro Met Glu Ile
    690                 695                 700

Ile Gln Asp Gly Val Ser Gly Tyr His Ile Asp Pro Tyr His Pro Asn
705                 710                 715                 720

Lys Ala Ala Glu Leu Met Val Glu Phe Phe Gln Arg Cys Glu Gln Asn
                725                 730                 735

Pro Thr His Trp Glu Asn Ile Ser Ala Ser Gly Leu Gln Arg Ile Leu
            740                 745                 750

Asp Arg Tyr Thr Trp Lys Ile Tyr Ser Glu Arg Leu Met Thr Leu Ala
        755                 760                 765

Gly Val Tyr Gly Phe Trp Lys Leu Val Ser Lys Leu Glu Arg Arg Glu
    770                 775                 780

Thr Arg Arg Tyr Leu Glu Met Phe Tyr Ile Leu Lys Phe Arg Glu Leu
785                 790                 795                 800
```

Val Lys Ser Val Pro Leu Ala Val Asp Glu Lys Gln
805 810

<210> SEQ ID NO 9
<211> LENGTH: 973
<212> TYPE: DNA
<213> ORGANISM: Arabidopsis thaliana

<400> SEQUENCE: 9
tagtgtagtc taatttagtt gtataactat aaaattgttg tttgtttccg aatcataagt 60 ttttttttt tttggttttg tattgatagg tgcaagagac tcaaaattct ggtttcgatg 120
ttaacagaat tcaagtagct gcccacttga ttcgatttgt tttgtatttg gaaacaacca 180
tggctggtca aggcccagcc cgttgtgctt ctgaacctgc ctagtcccat ggactagatc 240
tttatccgca gactccaaaa gaaaaaggat tggcgcagag gaattgtcat ggaaacagaa 300
tgaacaagaa agggtgaaga agatcaaagg catatatgat ctttacattc tctttagctt 360
atgtatgcag aaaattcacc taattaagga cagggaacgt aacttggctt gcactcctct 420
caccaaacct taccccctaa ctaattttaa ttcaaaatta ctagtatttt ggccgatcac 480
tttatataat aagataccag atttattata tttacgaatt atcagcatgc atatactgta 540
tatagttttt tttttgttaa agggtaaaat aataggatcc ttttgaataa aatgaacata 600
tataattagt ataatgaaaa cagaaggaaa tgagattagg acagtaagta aaatgagaga 660
gacctgcaaa ggataaaaaa gagaagctta aggaaaccgc gacgatgaaa gaaagacatg 720
tcatcagctg atggatgtga gtgatgagtt tgttgcagtt gtgtagaaat ttttactaaa 780
acagttgttt ttacaaaaaa gaaataatat aaaacgaaag cttagcttga aggcaatgga 840
gactctacaa caaactatgt accatacaga gagagaaact aaaagctttt cacacataaa 900
aaccaaactt attcgtctct cattgatcac cgttttgttc tctcaagatc gctgctaatc 960
tccggccgtc cct 973

<210> SEQ ID NO 10
<211> LENGTH: 1342
<212> TYPE: DNA
<213> ORGANISM: Arabidopsis thaliana

<400> SEQUENCE: 10
aatttgcatg ttattctaca tctatagtcc aaagatagca aaccaaagaa aaaaattgtc 60
acagagggtt caatgttact tagatagaaa tggttcttta caataataaa tttatgttcc 120
attcttcatg gaccgatggt atatatatga ctatatatat gttacaagaa aaacaaaaac 180
ttatattttc taaatatgtc ttcatccatg tcactagctc attgtgtata catttacttg 240
cttctttttg ttctatttca tttcctctaa caaattattc cttatatttt gtgatgtact 300
gaattattat gaaaaaaaac ctttacactt gatagagaag catatttgga aacgtatata 360
atttgtttaa ttggagtcac caaaattata caaatcttgt aatatcatta acataatagc 420
aaactaatta aatatatgtt ttgaggtcaa atgttcggtt tagtgttgaa actgaaaaaa 480
attattggtt aataaaattt caaataaaag gacaggtctt tctcaccaaa acaaatttca 540
agtatagata agaaaaatat aataagataa acaattcatg ctggtttggt tcgacttcaa 600
ctagttagtt gtataagaat atattttttt aatacatttt tttagcaact tttgtttttg 660
atacatataa acaaatattc acaataaaac caaactacaa atagcaacta aaataatttt 720
ttgaaaacga aattagtggg gacgaccttg aattgactga actacattcc tacgttccac 780

-continued aactactccc atttcattcc caaaccataa tcaatcactc gtataaacat ttttgtctcc 840
aaaaagtctc accaaccgca aaacgcttat tagttattac cttctcaatt cctcagccac 900
cagccacgac tacctttttcg atgcttgagg ttgatatttg acggaacaca caaatttaac 960
caaaccaaac caaaaccaaa cgcgttttaa atctaaaaac taattgacaa actctttttg 1020
cgactcaaac caaattcacg ttttccatta tccaccatta gatcaccaat cttcatccaa 1080
cggtcatcat taaactctca cccacccctc atacttcact ttttttctcc aaaaaatcaa 1140
aacttgtgtt ctctcttctc tcttctcttg tccttaccta acaacaacac taacattgtc 1200
cttcttattt aaacgtctct tctctcttct tcctcctcag aaaaccaaaa accaccaaca 1260
attcaaactc tctctttctc ctttcaccaa acaatacaag agatctgatc tcattcacct 1320
aaacacaact tcttgaaaac ca 1342

<210> SEQ ID NO 11
<211> LENGTH: 601
<212> TYPE: DNA
<213> ORGANISM: Petroselinum crispum

<400> SEQUENCE: 11
gatatacttt agcataccaa gatttcaaaa agttttccaa tttctttatc aaatactcac 60
agatttttac aaatttcaga ttcttcaaaa tatagaaata aaagaattag ataaaatatg 120
atgctattta atattactaa ttttgttttt tttaatctag cttggtttat cagaatcaaa 180
taagccagac tcttaaggat aattcaaaat attaatgtga tataccaaga ttcaaaaaag 240
ttttcgaaat ccatatcaaa tacttacaga tattataaat tttgaaaaat ctatattaaa 300
tatgtcagat tttcaaaata aataaaatcc gaaatgaatt taaagaaaat gccgtcctat 360
atatttgtga gttggtaaat ctcgccatca catgctgctt catcttagtc aactttttcc 420
cttcatcacc taacacacaa tatttttctc accaacccca ctcataattt aattccccat 480
tttaccccta accaaacctc atattccgat aaactccccc tttaccaacc cccatcccct 540
taccaaaccc tccacattta tatgttgaat tgttcatcat ctaacatgta agaaacctct 600
c 601

<210> SEQ ID NO 12
<211> LENGTH: 1663
<212> TYPE: DNA
<213> ORGANISM: Arabidopsis thaliana

<400> SEQUENCE: 12
aacttgttgt ttcataagtt ttaaaattta ttatctaatt atctactttt atgtgttcta 60
gagcaaagtg ctaaatgtat atatacttag atgttgtgtt gtaatccaat gtcaatataa 120
tcaatgattt agctatttgt aaacatacta aatagtattc caccaaaaaa aaaacatact 180
aaacagtaaa caaacagcaa aaacaaaatc cacatgtcct aaaagatagt ctgattttcg 240
ttcataatgc tctggttttt gaaagataat aattgtgttg tatgagtgta tgacaaatat 300
tcattggttt gagaagttaa caaaatttgg tggctacaaa tggtttccta ttcgagttgg 360
gtccattatc ccttggcgtg tacggaaata atacctaccc atcataatct gatcaaagat 420
gaggtagtct ttaaataaat tttgcggctt atatcaatct ttatgtacta taaactgtga 480
actttttgtt cttcaggact tccacatcat tgcccaatcc ggttatacct tcgctagtta 540
atatgttaat taacattaaa ttaaagagct aacatttctt aggtagtaaa atagaagttt 600
tgaactacta tactactaac atgtgaaaat actttagtca caaatatgac aatatacaaa 660

```
tttattggaa tgcaaattct tgaatttcaa ttgtttgaaa attatatatt tctacataac     720
aattctttat aaactaaaaa tattaatttt ccatggctat gcgttatacg tatatgtcaa     780
atatttttat tatttatata attttacgat aaattagtac tccactttac tatattactc     840
aacactaaaa gacctcttta actccgccta acatagatat gttttctttt gaatgtttcg     900
gttaaacatg acagagattt gttttcttgc tttcgctcaa tacatatttg tgctccttta     960
gaaaagtagt atttcctaac aatccaacat tttcatattt attatatctt ttaaatatta    1020
tcatggttct ttttctttcg tcatgtttgg cctctttaaa ataattcttg aattgtatga    1080
gcattaatcc aataacgtcc tgatcccaaa aacctcatat taggtttgag agtccgaaaa    1140
tatacttttc acataaagca cctaaggtgt catactttaa caacttcaca aaatatgcaa    1200
aatttgtcat tgtcactttg agatgtaagt tttttttac atgcaaatag attgagtctc     1260
tttacgtgta aattcattta ataaaattgt atggaatatc tatttatatc atatatttct    1320
aacatatata taaatatcta tacaaaaata cgactttttg gcacatgtaa ttagaaaaat    1380
ccacaagaaa cagaaaaaag aaacaccaaa tacaacgaaa tgaagaaatt attataaatt    1440
tgaatggctt aacatctctt aagagtcaac aaggtaaagg attaattagt agtcttcatc    1500
aatctttctc caccttcttc tattccttaa tctccacttt atctcccaaa cccgaaaact    1560
cctcttcacc aacttaaacc ctattaacta atcccaacaa tcagatgttt cgaattcaac    1620
aaccagctca ggccataaga ttcatcccgg agaaacaaga acg                      1663
```

<210> SEQ ID NO 13
<211> LENGTH: 1046
<212> TYPE: DNA
<213> ORGANISM: Arabidopsis thaliana

<400> SEQUENCE: 13

```
aaacaaaagt tgttaggaat tgattttaaa ttctgaaagt tagtgtagac ataggagtga      60
gtcagatatc catagagaac aatatgataa tatgtgaaaa ttaggtctga ttcattatat     120
ttacagtaat tagttgattg aatatgtcat ttatgcaata tgggagacaa ccaaacatac     180
acacacaagt ggctacttag tgattagtga tctgaaatta gtagtgaatt cgtatgtttt     240
atattcaatc acgcatatat atacgtgata cagtagtaaa accccataaa ccatatatgt     300
ggataaacgg gaagtactgt tgttaactag tggtcgatat cttattcaaa cttcgtaaga     360
ctttaactca cggatgattg aatatgttca tattgtagct tactagctta gtatctcact     420
catgcaccat tccataattt ttgttttctt tgtaaccatc tcattacaac tctaagctga     480
tcaaaactcg tttttaatta aaaatataca tgaatacaaa ttcagtctag tgatttatgt     540
tagtgtcgtc catgtgttac caattgtata taaatctcat ataatacatt cttttaaaag     600
aaaaattgta ctatcatata tatataaacg aaatgatatt ttgtagttaa aataccattt     660
catttcaaat ttagcaaaaa aaaaaaaaaa aaccatttca gaggaaaacg tcccaagaac     720
ataaatattt agcactaaca cacaaaccac aaacaactta ttgttgttcc accgtgttgt     780
gatttatcca ccaaaaagtt taaaaccaat acctataaca gtgtttgtag ttgtatatta     840
cctataatca tgacattcct atagataaaa acacataaga taaacaaatg aaattgatag     900
gttaggtgtg ggcctcaacg tgtgaaattt tggacatcca tcctatttgc tacaaacgcg     960
gttgggtctc atgaaatgcc tataaatacg gacacattct caagcaaact catctcacaa    1020
ctaaatctta agtagaaaga gtgaaa                                         1046
```

<210> SEQ ID NO 14
<211> LENGTH: 328
<212> TYPE: DNA
<213> ORGANISM: Strawberry vein banding virus

<400> SEQUENCE: 14
gctagctatc actgaaaaga cagcaagaca atggtgtctc gatgcaccag aaccacatct 60
ttgcagcaga tgtgaagcag ccagagtggt ccacaagacg cactcagaaa aggcatcttc 120
taccgacaca gaaaaagaca accacagctc atcatccaac atgtagactg tcgttatgcg 180
tcggctgaag ataagactga ccccaggcca gcactaaaga agaaataatg caagtggtcc 240
tagctccact ttagctttaa taattatgtt tcattattat tctctgcttt tgctctctat 300
ataaagagct tgtattttca tttgaagg 328

<210> SEQ ID NO 15
<211> LENGTH: 342
<212> TYPE: DNA
<213> ORGANISM: Cauliflower mosaic virus

<400> SEQUENCE: 15
tgagactttt caacaaaggg taatatccgg aaacctcctc ggattccatt gcccagctat 60
ctgtcacttt attgtgaaga tagtggaaaa ggaaggtggc tcctacaaat gccatcattg 120
cgataaagga aaggccatcg ttgaagatgc ctctgccgac agtggtccca aagatggacc 180
cccacccacg aggagcatcg tggaaaaaga agacgttcca accacgtctt caaagcaagt 240
ggattgatgt gatatctcca ctgacgtaag ggatgacgca caatcccact atccttcgca 300
agacccttcc tctatataag gaagttcatt tcatttggag ag 342

<210> SEQ ID NO 16
<211> LENGTH: 1047
<212> TYPE: DNA
<213> ORGANISM: Gossypium hirsutum

<400> SEQUENCE: 16
atggctgggg aatcaatttc cggaaacttg aaagatctga gcctgaatag aaatggtgct 60
gtctccaaaa agagccatct ggtggtgtgt tttggggaaa tgctcatcga tttcattcct 120
accgttgctg gtgtctccct tgctgaagct cccgcttttg aaaaggcacc aggaggtgct 180
cccgctaatg tggctgtttg cattagcaaa ctcggaggtt cctctgcatt catcggcaag 240
gttggagacg atgagtttgg aagaatgctc gccgacatac tgaaacagaa caacgttgac 300
aattccggaa tgagatttga tcatgacgcc cgtacagctc ttgcattcat aacccttaca 360
gcagagggag aaagagagtt cgtcttcttc agaaacccat ctgctgacat gctgttgagg 420
gaatctgaac ttgacgttga tctgattaag aaagcaacta tcttccatta cggaagcatc 480
tcactcattg atgagccttg ccgaagtaca caccttgctg caatggatat tgcaaaaaga 540
tctgggagta tactctccta tgatcctaac ttgaggctgc ctctctggcc ttctgaggat 600
gccgcaagga gtggaattat gagcgtctgg aatctcgctg acatcattaa gatttccgaa 660
gatgagatat cattccttac tggagctgac gatcctaacg atgacgaggt cgtgctgaaa 720
cgtctctttc acccaaatct taagctcctg ttggttaccg aaggctcagc aggctgtagg 780
tactacacta aggagtttaa gggacgtgtg aactcaatca aagtgaaggc agtggacaca 840
actggcgccg gggatgcatt cactgggggt gttttgaaat gcctcgcttc tgatgcctca 900
ctgtatcagg atgagaagag actgagggaa gctatcttct ttgcaaacgt ttgtgccgcc 960

-continued

```
ttgactgtca ctggacgagg aggaatacct tcattgccta cccaggatgc tgttcgccag   1020

actctggccg aagtgactgc atgataa                                       1047


<210> SEQ ID NO 17
<211> LENGTH: 2424
<212> TYPE: DNA
<213> ORGANISM: Gossypium hirsutum

<400> SEQUENCE: 17

atggccgagc gtgctcttac ccgcgtccat agtcttaggg aaaggctcga tgaaactctc     60

cttgcccatc gtaacgaaat cttggccttg cttagtagaa tagagggcaa gggaaaaggt    120

atccttcaac atcaccagat aattctggag tttgaagcta ttccagagga gaacagaaaa    180

aaactcgcca acggtgcctt ctttgaagtt cttaaggctt ctcaagaggc tatagtcttg    240

ccaccttggg ttgcattggc cgtgaggccc agaccagggg tttgggagta tatcagagtc    300

aatgttcacg cactcgttgt tgaagaactc acagtggctg aatacctcca tttcaaggag    360

gaattggttg atggtagttc caatgggaac ttcgtgctgg aactggactt tgaacccttt    420

aattctagct ttccaaggcc aacactttct aagagtattg gaaacggtgt cgagtttctc    480

aatcgtcacc tgtctgctaa acttttccac gacaaagagt ctatgcatcc acttctggag    540

ttccttagag tgcattgcca taaagggaag aacatgatgc tgaacgatag gatacagaac    600

ctcaatgcct tgcaacacgt gctgagaaaa gctgaagagt acttgggaac tctgccacct    660

gaaacccctt gtgccgagtt tgagcatagg tttcaagaga ttggattgga acgcggctgg    720

ggagataccg cagagcgtgt tcttgagatg atacaactcc tgcttgatct tctggaagcc    780

actgacccat gcacattgga aaagttcctc ggccgaatac ccatggtttt caacgtggtc    840

attttgaccc cccatggata tttcgctcaa gataacgtgt tgggttatcc agataccggg    900

ggacaagtgg tttacattct tgatcaagtt agggcacttg aaaacgagat gctcttgagg    960

atcaaacagc aaggacttaa catcacacct cgaatcctga ttatcactag actcttgcct   1020

gacgccgtcg gtacaacatg cgggcaaagg ttggagaaag tttacggcac tgaacatagc   1080

gatattctcc gtgtgccatt tcgaaccgaa aaaggcatag tccgaaaatg gatcagtcga   1140

ttcgaaaagg tctggccata tcttgagacc tatactgagg atgtcgctca tgagatctct   1200

aaggaattgc atggcactcc tgatctcatc ataggaaact actccgatgg caatatagtt   1260

gcttccttgc ttgcacacaa gttgggcgtt acacaatgta ccatcgcaca cgcactggaa   1320

aagaccaagt accctgatag tgatatctat tggaagaaac tcgaagataa gtaccacttc   1380

tcatgtcagt tcaccgctga tctgttcgcc atgaatcata ctgatttcat cattacctca   1440

acttttcaag agatagctgg ctccaaggac actgtgggtc agtatgagtc acataccgcc   1500

tttactttgc ctggactgta tagagtggtc cacggtatag atgttttcga tcccaagttc   1560

aacatagtgt ctccaggggc agatatggaa atctacttcc cttacaccga ggaaaagcgc   1620

cgtttgaagc actttcaccc agaaattgag gacttgctgt acaccaaagt tgaaaatgag   1680

gagcacttgt gcgttcttaa cgaccgaaac aaaccaatcc tgtttacaat gccacgattg   1740

gatagagtca agaatctcac agggttggtg gagtggtgtg gcaaaaatcc caagttgaga   1800

gagctggcta acctggtcgt ggttggtggg gatcgtagaa aggagagtaa ggatctcgaa   1860

gagaaagctg agatgaagaa gatgtttgaa ctcattgaca agtacaacct taatggacaa   1920

ttcagatgga tttcttctca gatgaatcgc atcaggaatg ttgagttgta tagatatatt   1980
```

-continued

```
tgcgacacta aaggtgcttt cgtgcaacct gctctctatg aagccttcgg cctcacagtg   2040

gtcgaggcta tgacatgcgg ccttcctaca tttgcaactt gtaatggtgg tcccgctgaa   2100

attatcgtgc acgggaagag cggattcaat atcgacccct atcatggaga ccaggccgca   2160

gacatacttg ttgatttctt cgaaaagtgt aagaaagacc cttctcactg ggacaagata   2220

agtcaaggtg gcctgaagag gattgaggaa aagtacacat ggaagatcta ctccgaacgc   2280

cttcttacat tgactggtgt ctatggtttc tggaagcatg tgagcaatct tgagaggaga   2340

gagtcccgac gttacttgga gatgttctat gccctgaaat accgcaaatt ggccgagtcc   2400

gtgcctcttg ccgaagaatg ataa                                          2424
```

<210> SEQ ID NO 18
<211> LENGTH: 4683
<212> TYPE: DNA
<213> ORGANISM: Artificial sequence
<220> FEATURE:
<223> OTHER INFORMATION: Double transgene: tomato fructokinase 1 is under 35S promoter and cotton SuSy under SvBv promoter. AGS terminator is used for fructokinase and NOS terminator for SuSy.

<400> SEQUENCE: 18

```
tgagactttt caacaaaggg taatatccgg aaacctcctc ggattccatt gcccagctat     60

ctgtcacttt attgtgaaga tagtggaaaa ggaaggtggc tcctacaaat gccatcattg    120

cgataaagga aaggccatcg ttgaagatgc ctctgccgac agtggtccca aagatggacc    180

cccacccacg aggagcatcg tggaaaaaga agacgttcca accacgtctt caaagcaagt    240

ggattgatgt gatatctcca ctgacgtaag ggatgacgca caatcccact atccttcgca    300

agacccttcc tctatataag gaagttcatt tcatttggag agatggctgg ggaatcaatt    360

tccggaaact tgaaagatct gagcctgaat agaaatggtg ctgtctccaa aaagagccat    420

ctggtggtgt gttttgggga aatgctcatc gatttcattc ctaccgttgc tggtgtctcc    480

cttgctgaag ctcccgcttt tgaaaaggca ccaggaggtg ctcccgctaa tgtggctgtt    540

tgcattagca aactcggagg ttcctctgca ttcatcggca aggttggaga cgatgagttt    600

ggaagaatgc tcgccgacat actgaaacag aacaacgttg acaattccgg aatgagattt    660

gatcatgacg cccgtacagc tcttgcattc ataaccctta cagcagaggg agaaagagag    720

ttcgtcttct tcagaaaccc atctgctgac atgctgttga gggaatctga acttgacgtt    780

gatctgatta agaaagcaac tatcttccat tacggaagca tctcactcat tgatgagcct    840

tgccgaagta cacaccttgc tgcaatggat attgcaaaaa gatctgggag tatactctcc    900

tatgatccta acttgaggct gcctctctgg ccttctgagg atgccgcaag gagtggaatt    960

atgagcgtct ggaatctcgc tgacatcatt aagatttccg aagatgagat atcattcctt   1020

actggagctg acgatcctaa cgatgacgag gtcgtgctga aacgtctctt tcacccaaat   1080

cttaagctcc tgttggttac cgaaggctca gcaggctgta ggtactacac taaggagttt   1140

aagggacgtg tgaactcaat caaagtgaag gcagtggaca caactggcgc cggggatgca   1200

ttcactgggg gtgttttgaa atgcctcgct tctgatgcct cactgtatca ggatgagaag   1260

agactgaggg aagctatctt ctttgcaaac gtttgtgccg ccttgactgt cactggacga   1320

ggaggaatac cttcattgcc tacccaggat gctgttcgcc agactctggc cgaagtgact   1380

gcatgataat gcatttgatt agtgaaaatt aattttcagt gcagtatttt ctattcgatc   1440

tttatgtaat ccgtttcaat gaataaattt aaatccgatg attagctgtt gtttatatta   1500

attcgtattt catccatatt tttattagaa tcttgagatg ttaaaaaatt tcagtcaaaa   1560
```

```
tttaaacagt gaaactttat tcaatatttc tgtatcgcac aatgcaaatc tatgtgagat   1620
tacaagatac cgacactgtt atttaacata acatagacat gctagctatc actgaaaaga   1680
cagcaagaca atggtgtctc gatgcaccag aaccacatct ttgcagcaga tgtgaagcag   1740
ccagagtggt ccacaagacg cactcagaaa aggcatcttc taccgacaca gaaaaagaca   1800
accacagctc atcatccaac atgtagactg tcgttatgcg tcggctgaag ataagactga   1860
ccccaggcca gcactaaaga agaaataatg caagtggtcc tagctccact ttagctttaa   1920
taattatgtt tcattattat tctctgcttt tgctctctat ataaagagct tgtattttca   1980
tttgaaggat ggccgagcgt gctcttaccc gcgtccatag tcttagggaa aggctcgatg   2040
aaactctcct tgcccatcgt aacgaaatct tggccttgct tagtagaata gagggcaagg   2100
gaaaaggtat ccttcaacat caccagataa ttctggagtt tgaagctatt ccagaggaga   2160
acagaaaaaa actcgccaac ggtgccttct ttgaagttct taaggcttct caagaggcta   2220
tagtcttgcc accttgggtt gcattggccg tgaggcccag accaggggtt tgggagtata   2280
tcagagtcaa tgttcacgca ctcgttgttg aagaactcac agtggctgaa tacctccatt   2340
tcaaggagga attggttgat ggtagttcca atgggaactt cgtgctggaa ctggactttg   2400
aaccctttaa ttctagcttt ccaaggccaa cactttctaa gagtattgga aacggtgtcg   2460
agtttctcaa tcgtcacctg tctgctaaac ttttccacga caaagagtct atgcatccac   2520
ttctggagtt ccttagagtg cattgccata aagggaagaa catgatgctg aacgatagga   2580
tacagaacct caatgccttg caacacgtgc tgagaaaagc tgaagagtac ttgggaactc   2640
tgccacctga aacccccttgt gccgagtttg agcataggtt tcaagagatt ggattggaac   2700
gcggctgggg agataccgca gagcgtgttc ttgagatgat acaactcctg cttgatcttc   2760
tggaagccac tgacccatgc acattggaaa agttcctcgg ccgaataccc atggttttca   2820
acgtggtcat tttgaccccc catggatatt tcgctcaaga taacgtgttg ggttatccag   2880
ataccggggg acaagtggtt tacattcttg atcaagttag ggcacttgaa aacgagatgc   2940
tcttgaggat caaacagcaa ggacttaaca tcacacctcg aatcctgatt atcactagac   3000
tcttgcctga cgccgtcggt acaacatgcg ggcaaaggtt ggagaaagtt tacggcactg   3060
aacatagcga tattctccgt gtgccatttc gaaccgaaaa aggcatagtc cgaaaatgga   3120
tcagtcgatt cgaaaaggtc tggccatatc ttgagaccta tactgaggat gtcgctcatg   3180
agatctctaa ggaattgcat ggcactcctg atctcatcat aggaaactac tccgatggca   3240
atatagttgc ttccttgctt gcacacaagt tgggcgttac acaatgtacc atcgcacacg   3300
cactggaaaa gaccaagtac cctgatagtg atatctattg gaagaaactc gaagataagt   3360
accacttctc atgtcagttc accgctgatc tgttcgccat gaatcatact gatttcatca   3420
ttacctcaac ttttcaagag atagctggct ccaaggacac tgtgggtcag tatgagtcac   3480
ataccgcctt tactttgcct ggactgtata gagtggtcca cggtatagat gttttcgatc   3540
ccaagttcaa catagtgtct ccaggggcag atatggaaat ctacttccct tacaccgagg   3600
aaaagcgccg tttgaagcac tttcacccag aaattgagga cttgctgtac accaaagttg   3660
aaaatgagga gcacttgtgc gttcttaacg accgaaacaa accaatcctg tttacaatgc   3720
cacgattgga tagagtcaag aatctcacag ggttggtgga gtggtgtggc aaaaatccca   3780
agttgagaga gctggctaac ctggtcgtgg ttggtgggga tcgtagaaag gagagtaagg   3840
atctcgaaga gaaagctgag atgaagaaga tgtttgaact cattgacaag tacaacctta   3900
```

```
atggacaatt cagatggatt tcttctcaga tgaatcgcat caggaatgtt gagttgtata   3960

gatatatttg cgacactaaa ggtgctttcg tgcaacctgc tctctatgaa gccttcggcc   4020

tcacagtggt cgaggctatg acatgcggcc ttcctacatt tgcaacttgt aatggtggtc   4080

ccgctgaaat tatcgtgcac gggaagagcg gattcaatat cgacccctat catggagacc   4140

aggccgcaga catacttgtt gatttcttcg aaaagtgtaa gaaagaccct tctcactggg   4200

acaagataag tcaaggtggc ctgaagagga ttgaggaaaa gtacacatgg aagatctact   4260

ccgaacgcct tcttacattg actggtgtct atggtttctg gaagcatgtg agcaatcttg   4320

agaggagaga gtcccgacgt tacttggaga tgttctatgc cctgaaatac cgcaaattgg   4380

ccgagtccgt gcctcttgcc gaagaatgat aagaatttcc ccgatcgttc aaacatttgg   4440

caataaagtt tcttaagatt gaatcctgtt gccggtcttg cgatgattat catataattt   4500

ctgttgaatt acgttaagca tgtaataatt aacatgtaat gcatgacgtt atttatgaga   4560

tgggttttta tgattagagt cccgcaatta tacatttaat acgcgataga aaacaaaata   4620

tagcgcgcaa actaggataa attatcgcgc gcggtgtcat ctatgttact agatcgggaa   4680

ttc                                                                 4683
```

<210> SEQ ID NO 19
<211> LENGTH: 5956
<212> TYPE: DNA
<213> ORGANISM: Artificial sequence
<220> FEATURE:
<223> OTHER INFORMATION: Double transgene: tomato fructokinase 1 is under 4CL-1 promoter and cotton SuSy is under PAL2 promoter.

<400> SEQUENCE: 19

```
gatatacttt agcataccaa gatttcaaaa agttttccaa tttctttatc aaatactcac     60

agatttttac aaatttcaga ttcttcaaaa tatagaaata aaagaattag ataaaatatg    120

atgctattta atattactaa ttttgttttt tttaatctag cttggtttat cagaatcaaa    180

taagccagac tcttaaggat aattcaaaat attaatgtga tataccaaga ttcaaaaaag    240

ttttcgaaat ccatatcaaa tacttacaga tattataaat tttgaaaaat ctatattaaa    300

tatgtcagat tttcaaaata aataaaatcc gaaatgaatt taaagaaaat gccgtcctat    360

atatttgtga gttggtaaat ctcgccatca catgctgctt catcttagtc aactttttcc    420

cttcatcacc taacacacaa tatttttctc accaacccca ctcataattt aattccccat    480

tttaccccta accaaacctc atattccgat aaactccccc tttaccaacc cccatcccct    540

taccaaaccc tccacattta tatgttgaat tgttcatcat ctaacatgta agaaacctct    600

catggctggg gaatcaattt ccggaaactt gaaagatctg agcctgaata gaaatggtgc    660

tgtctccaaa aagagccatc tggtggtgtg ttttggggaa atgctcatcg atttcattcc    720

taccgttgct ggtgtctccc ttgctgaagc tcccgctttt gaaaaggcac caggaggtgc    780

tcccgctaat gtggctgttt gcattagcaa actcggaggt tcctctgcat tcatcggcaa    840

ggttggagac gatgagtttg gaagaatgct cgccgacata ctgaaacaga acaacgttga    900

caattccgga atgagatttg atcatgacgc ccgtacagct cttgcattca taaccettac    960

agcagaggga gaaagagagt tcgtcttctt cagaaaccca tctgctgaca tgctgttgag   1020

ggaatctgaa cttgacgttg atctgattaa gaaagcaact atcttccatt acggaagcat   1080

ctcactcatt gatgagcctt gccgaagtac acaccttgct gcaatggata ttgcaaaaag   1140

atctgggagt atactctcct atgatcctaa cttgaggctg cctctctggc cttctgagga   1200
```

-continued

```
tgccgcaagg agtggaatta tgagcgtctg gaatctcgct gacatcatta agatttccga   1260
agatgagata tcattcctta ctggagctga cgatcctaac gatgacgagg tcgtgctgaa   1320
acgtctcttt cacccaaatc ttaagctcct gttggttacc gaaggctcag caggctgtag   1380
gtactacact aaggagttta agggacgtgt gaactcaatc aaagtgaagg cagtggacac   1440
aactggcgcc ggggatgcat tcactggggg tgttttgaaa tgcctcgctt ctgatgcctc   1500
actgtatcag gatgagaaga gactgaggga agctatcttc tttgcaaacg tttgtgccgc   1560
cttgactgtc actggacgag gaggaatacc ttcattgcct acccaggatg ctgttcgcca   1620
gactctggcc gaagtgactg catgataatg catttgatta gtgaaaatta attttcagtg   1680
cagtattttc tattcgatct ttatgtaatc cgtttcaatg aataaattta aatccgatga   1740
ttagctgttg tttatattaa ttcgtatttc atccatattt ttattagaat cttgagatgt   1800
taaaaaattt cagtcaaaat ttaaacagtg aaactttatt caatatttct gtatcgcaca   1860
atgcaaatct atgtgagatt acaagatacc gacactgtta tttaacataa catagacata   1920
atttgcatgt tattctacat ctatagtcca aagatagcaa accaaagaaa aaaattgtca   1980
cagagggttc aatgttactt agatagaaat ggttctttac aataataaat ttatgttcca   2040
ttcttcatgg accgatggta tatatatgac tatatatatg ttacaagaaa aacaaaaact   2100
tatattttct aaatatgtct tcatccatgt cactagctca ttgtgtatac atttacttgc   2160
ttctttttgt tctatttcat ttcctctaac aaattattcc ttatattttg tgatgtactg   2220
aattattatg aaaaaaaacc tttacacttg atagagaagc atatttggaa acgtatataa   2280
tttgtttaat tggagtcacc aaaattatac aaatcttgta atatcattaa cataatagca   2340
aactaattaa atatatgttt tgaggtcaaa tgttcggttt agtgttgaaa ctgaaaaaaa   2400
ttattggtta ataaaatttc aaataaaagg acaggtcttt ctcaccaaaa caaatttcaa   2460
gtatagataa gaaaaatata ataagataaa caattcatgc tggtttggtt cgacttcaac   2520
tagttagttg tataagaata tatttttta atacattttt ttagcaactt ttgtttttga   2580
tacatataaa caaatattca caataaaacc aaactacaaa tagcaactaa aataattttt   2640
tgaaaacgaa attagtgggg acgaccttga attgactgaa ctacattcct acgttccaca   2700
actactccca tttcattccc aaaccataat caatcactcg tataaacatt tttgtctcca   2760
aaaagtctca ccaaccgcaa aacgcttatt agttattacc ttctcaattc ctcagccacc   2820
agccacgact accttttcga tgcttgaggt tgatatttga cggaacacac aaatttaacc   2880
aaaccaaacc aaaaccaaac gcgttttaaa tctaaaaact aattgacaaa ctctttttgc   2940
gactcaaacc aaattcacgt tttccattat ccaccattag atcaccaatc ttcatccaac   3000
ggtcatcatt aaactctcac ccacccctca tacttcactt tttttctcca aaaaatcaaa   3060
acttgtgttc tctcttctct cttctcttgt ccttacctaa caacaacact aacattgtcc   3120
ttcttattta aacgtctctt ctctcttctt cctcctcaga aaaccaaaaa ccaccaacaa   3180
ttcaaactct ctctttctcc tttcaccaaa caatacaaga gatctgatct cattcaccta   3240
aacacaactt cttgaaaacc aatggccgag cgtgctctta cccgcgtcca tagtcttagg   3300
gaaaggctcg atgaaactct ccttgcccat cgtaacgaaa tcttggcctt gcttagtaga   3360
atagagggca agggaaaagg tatccttcaa catcaccaga taattctgga gtttgaagct   3420
attccagagg agaacagaaa aaaactcgcc aacggtgcct tctttgaagt tcttaaggct   3480
tctcaagagg ctatagtctt gccaccttgg gttgcattgg ccgtgaggcc cagaccaggg   3540
gtttgggagt atatcagagt caatgttcac gcactcgttg ttgaagaact cacagtggct   3600
```

-continued

```
gaatacctcc atttcaagga ggaattggtt gatggtagtt ccaatgggaa cttcgtgctg   3660
gaactggact ttgaaccctt taattctagc tttccaaggc caacactttc taagagtatt   3720
ggaaacggtg tcgagtttct caatcgtcac ctgtctgcta aacttttcca cgacaaagag   3780
tctatgcatc cacttctgga gttccttaga gtgcattgcc ataaagggaa gaacatgatg   3840
ctgaacgata ggatacagaa cctcaatgcc ttgcaacacg tgctgagaaa agctgaagag   3900
tacttgggaa ctctgccacc tgaaacccct tgtgccgagt ttgagcatag gtttcaagag   3960
attggattgg aacgcggctg gggagatacc gcagagcgtg ttcttgagat gatacaactc   4020
ctgcttgatc ttctggaagc cactgaccca tgcacattgg aaaagttcct cggccgaata   4080
cccatggttt tcaacgtggt cattttgacc ccccatggat atttcgctca agataacgtg   4140
ttgggttatc cagataccgg gggacaagtg gtttacattc ttgatcaagt tagggcactt   4200
gaaaacgaga tgctcttgag gatcaaacag caaggactta acatcacacc tcgaatcctg   4260
attatcacta gactcttgcc tgacgccgtc ggtacaacat gcgggcaaag gttggagaaa   4320
gtttacggca ctgaacatag cgatattctc cgtgtgccat ttcgaaccga aaaaggcata   4380
gtccgaaaat ggatcagtcg attcgaaaag gtctggccat atcttgagac ctatactgag   4440
gatgtcgctc atgagatctc taaggaattg catggcactc ctgatctcat cataggaaac   4500
tactccgatg gcaatatagt tgcttccttg cttgcacaca agttgggcgt tacacaatgt   4560
accatcgcac acgcactgga aaagaccaag taccctgata gtgatatcta ttggaagaaa   4620
ctcgaagata agtaccactt ctcatgtcag ttcaccgctg atctgttcgc catgaatcat   4680
actgatttca tcattacctc aacttttcaa gagatagctg gctccaagga cactgtgggt   4740
cagtatgagt cacataccgc ctttactttg cctggactgt atagagtggt ccacggtata   4800
gatgttttcg atcccaagtt caacatagtg tctccagggg cagatatgga aatctacttc   4860
ccttacaccg aggaaaagcg ccgtttgaag cactttcacc cagaaattga ggacttgctg   4920
tacaccaaag ttgaaaatga ggagcacttg tgcgttctta acgaccgaaa caaaccaatc   4980
ctgtttacaa tgccacgatt ggatagagtc aagaatctca cagggttggt ggagtggtgt   5040
ggcaaaaatc ccaagttgag agagctggct aacctggtcg tggttggtgg ggatcgtaga   5100
aaggagagta aggatctcga agagaaagct gagatgaaga agatgtttga actcattgac   5160
aagtacaacc ttaatggaca attcagatgg atttcttctc agatgaatcg catcaggaat   5220
gttgagttgt atagatatat ttgcgacact aaaggtgctt tcgtgcaacc tgctctctat   5280
gaagccttcg gcctcacagt ggtcgaggct atgacatgcg gccttcctac atttgcaact   5340
tgtaatggtg gtcccgctga aattatcgtg cacgggaaga gcggattcaa tatcgacccc   5400
tatcatggag accaggccgc agacatactt gttgatttct tcgaaaagtg taagaaagac   5460
ccttctcact gggacaagat aagtcaaggt ggcctgaaga ggattgagga aaagtacaca   5520
tggaagatct actccgaacg ccttcttaca ttgactggtg tctatggttt ctggaagcat   5580
gtgagcaatc ttgagaggag agagtcccga cgttacttgg agatgttcta tgccctgaaa   5640
taccgcaaat tggccgagtc cgtgcctctt gccgaagaat gataagaatt tccccgatcg   5700
ttcaaacatt tggcaataaa gtttcttaag attgaatcct gttgccggtc ttgcgatgat   5760
tatcatataa tttctgttga attacgttaa gcatgtaata attaacatgt aatgcatgac   5820
gttatttatg agatgggttt ttatgattag agtcccgcaa ttatacattt aatacgcgat   5880
agaaaacaaa atatagcgcg caaactagga taaattatcg cgcgcggtgt catctatgtt   5940
```

actagatcgg gaattc 5956

<210> SEQ ID NO 20
<211> LENGTH: 1887
<212> TYPE: DNA
<213> ORGANISM: Solanum lycopersicum
<300> PUBLICATION INFORMATION:
<308> DATABASE ACCESSION NUMBER: U64817
<309> DATABASE ENTRY DATE: 1997-05-15
<313> RELEVANT RESIDUES IN SEQ ID NO: (1)..(1887)

<400> SEQUENCE: 20
ggcacgagat tgatcctcat tctgcataag aaaattccgg tacatttcat gccgtgtcgg 60
tgtcagcaag gtacaccaaa agtagtaaac agggtggcaa aaaagaggag gatttagcaa 120
tttgttgatt tttccttctt tctttctttc ttgtcaactt caaaacccca tcggctctct 180
ttcaaggttc ccctttcttt ctctattaac gcctctctct gagttcttgt tgatatttcc 240
aaagacccca tttttaacac tgctcacaat atggctggcg aatccatttc aggcaattta 300
aaagaccttt ccttgaatag aaatggtgcg gtgtcaaaga agtctcattt agttgtttgc 360
tttggggaga tgctcattga cttcatccca actgttgctg gagtttcact tgcggaagct 420
cctgcctttg aaaaagctcc cggtggtgca cctgctaatg ttgctgtgtg catctcaaag 480
ttagggggtt catctgcttt tattggaaag gttggtgacg atgagttcgg ccgtatgttg 540
gctgacattt tgaagcaaaa caatgttgac aattccggca tgcggtttga tcatgatgca 600
aggactgcac tggccttcat tacactcaca gctgaaggtg agcgggagtt cgtgtttttc 660
cgtaatccta gtgctgatat gcttcttcgg gagtcagaac tcgatgtaga tcttattaaa 720
aaggccacca tcttccatta tggttcaatt agtttgatcg acgaaccttg taggtcaaca 780
caccttgctg caatggacat tgccaaaaga tcaggtagca tactgtcgta tgatccaaac 840
ctgagattgc ctttatggcc ttcagaagat gctgctcgaa gtggaataat gagtgtatgg 900
aacctagcag atattattaa gataagtgag gatgaaattt cattcttgac tggagccgac 960
gatccaaatg atgacgaggt ggtgttgaag aggcttttcc atcctaatct gaagcttttg 1020
cttgtaactg aaggttcagc tggttgcaga tattacacca aggaattcaa gggaagagta 1080
aattcgatca aggtaaaagc tgttgataca actggtgctg gtgatgcatt tactggtgga 1140
gttctcaagt gtctagcttc tgatgctagt ctttatcagg atgaaaagcg gttaagggag 1200
gctatctttt ttgccaatgt ttgtgctgcc ctgacagtga caggaagagg tggaatccct 1260
tcccttccta cacaagatgc agttcgacaa actcttgccg aggtcactgc atgagaaggc 1320
agaacaaagt tttgttctct tcacactgta tctgcattat tctagattta ttttcacaat 1380
gatcgattta ttttgttttc gtctctggca tctgttggtc ggttcctctc tttggaaaga 1440
agttgcagcc aacgagacat gcagggaaaa atagggtagc gcgtcttctg tcagtcatgc 1500
aaggaaatgc tggaaagcct ttttcgctaa gtcaaaatac aagctgttat gtctccgtta 1560
catatctgat ccttgttacg gatccatcag aagccaagat agtgaaggtt gttaacattg 1620
gttattgaga tttactgcgt gtagagagaa gaacaaaagg tggacatgca tttaacgact 1680
atcagctttt gtttgtttta atatgtttcc ttttcaagaa cctttctgtt tttgtttcct 1740
ttaaagtgtc tgtattataa ggtgacttca atgctgtctt gattagaaat cagcagaaca 1800
aaaaatatta cttatgcagt tatgtggttt gatgtactac tcagaaatca gaataatatg 1860
agtctcatac tgttgatctc ttccatc 1887

<210> SEQ ID NO 21
<211> LENGTH: 1261
<212> TYPE: DNA
<213> ORGANISM: Solanum lycopersicum
<300> PUBLICATION INFORMATION:
<308> DATABASE ACCESSION NUMBER: U64818
<309> DATABASE ENTRY DATE: 1997-05-13
<313> RELEVANT RESIDUES IN SEQ ID NO: (1)..(1261)

<400> SEQUENCE: 21
ggcacgagaa aatctataga tacacctata gatacatata ttttctctat tcatcgtagc 60
catggcagtt aacggtgctt cttcttctgg tttgatcgtc agtttcggtg agatgttgat 120
cgatttcgtt ccgacagtct ccggcgtatc ccttgccgag gctcccggat ttttgaaagc 180
tcccggcggt gcaccggcga acgtcgctat cgcggtgacg aggctcggag ggaagtcggc 240
gttcgtcggg aaactcggcg acgatgagtt cggtcacatg ctcgccggga ttctgaaaac 300
gaacggcgta caagccgaag gaattaattt tgacaagggc gccaggacgg ctttggcgtt 360
cgtgacgcta cgcgccgacg gagagcgtga gtttatgttt tacagaaatc ccagtgccga 420
tatgttgctc acgcccgctg agttgaatct tgatcttatt agatctgcta aggtgttcca 480
ctatggatca attagtttga tcgtggagcc atgtagagca gcacatatga aggcaatgga 540
agtagcaaag gaggcagggg cattgctctc ttatgaccca aaccttcgtt tgccgttgtg 600
gccttcagca gaagaggcca agaagcaaat caagagcata tgggactctg ctgatgtgat 660
caaggtcagc gatgtggagc tcgaattcct cactggaagc aacaagattg atgatgaatc 720
cgccatgtcc ttgtggcatc ctaacttgaa gctactcttg gtcactcttg gtgaaaaggg 780
ttgcaattac tacaccaaga aattccatgg aaccgttgga ggattccatg tgaagactgt 840
tgacaccact ggagctggtg attcttttgt tggtgccctt ctaaccaaga ttgttgatga 900
tcaaaccatt ctcgaggatg aagcaaggtt gaaggaagta cttaggtttt catgtgcatg 960
tggagccatc actacaacca agaaaggagc aatcccagct ttgcctactg catctgaagc 1020
cctcactttg ctcaagggag gagcatagaa acatcgtgtt atcttttttc tttttccat 1080 cttcatatat ttcccccccct ttatgagttt ttttgaagct agtaggaagc cttttcagtt 1140
ttggatttta atgttttgtt gtgatgaatg tccatcaaga cacttaataa actaagcttt 1200
cttcatatgc agcttccttg taacttctcc tttacatcat catactagta tttcattatc 1260
c 1261

<210> SEQ ID NO 22
<211> LENGTH: 1470
<212> TYPE: DNA
<213> ORGANISM: Solanum lycopersicum
<300> PUBLICATION INFORMATION:
<308> DATABASE ACCESSION NUMBER: AY323226
<309> DATABASE ENTRY DATE: 2004-03-26
<313> RELEVANT RESIDUES IN SEQ ID NO: (1)..(1470)

<400> SEQUENCE: 22
ttcattgatt tctccgctgc tactatcttc cccaacagaa agaattgctt caaaattagg 60
gtttattgcc tgaaaattac tagttttaca acgattgctc caataccttc tcctaatttc 120
cattttagtt gctgaaattt tgacgcctga tgtaactgta ttttaggttt taattgtgaa 180
atacgagttt ctcagatcag atcagttcct ctgttttttt tactttctaa taaatggctc 240
ttcatgctac tgctttctcc ttcactggag tttctacttc aagtaaatct tccagaagcg 300
ctttgctttc tcttcctaga agatgcgctg tcaaagcaac ttcccagtat ccgcacagct 360

-continued

```
ttcctcgatg taaaatccaa ggaagagcat tgccaagtga caatgggcta gtggagaagg    420

atgaatcttc tcttgttgtg tgctttggag aaatgctcat tgattttgtt ccgactacaa    480

gtgggctttc attggctgaa gctcctgcat ttaaaaaggc tcctggtggt gcaccagcta    540

atgttgctgt tggtatttcc cgtcttggtg gttcatcagc tttcattggc aaggttggtg    600

aagacgaatt tggttacatg cttgctgaga ttttgaagga gaacaatgtc aacagtgatg    660

gtatgcgatt tgatccaggt gctcgcactg ctttagcatt tgtaacactg agaaaggatg    720

gagaacgtga atttatgttc tatcgtaacc caagtgctga tatgttgctt caagaggatg    780

aacttgattt agagttgatc aggaaggcaa aagtttttca ttatggttcc ataagtctga    840

ttacggagcc atgcaaatca gcccatattg cagctgcaaa agctgcaaag gatgctggtg    900

tgatcttatc ctatgatccc aatttgaggc ttccattgtg gccatctgca gaaagtgcta    960

gagaaggaat ccttagcata tggaatactg ctgatataat taagataagt gaagaagaga   1020

tttcgttttt gacacaagga gaagatcctt atgatgataa tgttgtccgt aagttgtacc   1080

atccaaacct caagttactc ctcgtcacag aaggtccaga aggttgccga tattacacca   1140

aggatttcag tggacgagtt aagggtataa aggtggacgc tgtggacacc acaggtgctg   1200

gagatgcttt tgtagccgga atattgtcac agctagcatc tgatgtctct ctgcttcagg   1260

atgagggcaa gcttcgagat gcccttagtt ttgctaatgc ctgtggtgca ttgaccgtga   1320

tggagagagg agcaattcca gctttgccta caaaagaagt agtgttgaac accttgctca   1380

agtcagttgc ataatatcca tccgacctat taatcggttg ccatttaaat gcacttgcaa   1440

aaagatctcc atgtgctgcc ttgcatagtt                                    1470


<210> SEQ ID NO 23
<211> LENGTH: 1304
<212> TYPE: DNA
<213> ORGANISM: Solanum lycopersicum
<300> PUBLICATION INFORMATION:
<308> DATABASE ACCESSION NUMBER: AY099454
<309> DATABASE ENTRY DATE: 2002-10-02
<313> RELEVANT RESIDUES IN SEQ ID NO: (1)..(1304)

<400> SEQUENCE: 23

aaaaaagagt ggaaaatggc ctgttgtttc cctgttattc ttgaccgatc catgagaagc     60

agcttcaagc tatctaagag ctcctcttct agtaaactcg ataaaagcaa gagctctata    120

tgttcaccaa catccttatc gacgaagaag aagtcgatcc aggaaaatga taacctggtt    180

gtatgttttg gggagctgtt gatagatttt gtgcctacag tatctggagt ttcacttgca    240

gaagcacctg gttttaaaaa ggctcctggt ggggctccag ctaatgttgc agttggtatt    300

gcaagattag gtggatcttc cgcttttatt ggcaaggtgg gtgcagatga atttggttac    360

atgttagctg atatattaaa acagaacaat gtcgacaatt ctggtatgcg ttttgatact    420

catgctagaa cagcgttggc gtttgttaca ttgaaatcag acggtgagag agaattcatg    480

tttttccgca atccaagtgc tgatatgctt ctaactgagg cagagctcga caagaatctc    540

attcaaaagg caagaatctt tcactatggt tcaatctctt tgattgctga accatgtagg    600

tcagctcatc ttgctgccat ggaaactgct aaaaatgcag gctgcattct ttcttatgac    660

ccaaatctaa ggttgccttt atggccatcc gaagaggctg ctcgtgaagg aattttaagc    720

atttgggacc aagctgacat tattaaggta agtgaagatg aaatcacatt tttgacaaat    780

ggtgaagatg cttatgatga caatgtcgtc atgactaagc ttttccactc caaccttaaa    840

cttttgctcg taactgaagg cggagacggt tgcagatact atactaataa ttttcatgga    900
```

agagtgagtg gcgttaaagt tgcagcagtt gacaccacag gagcaggtga tgcatttgtt 960
ggtggacttc tcaacagtat ggcctcagat ccagacattt acatggatga gaagaaatta 1020
agggatgcac tcctatttgc taatggatgt ggagcaataa ctgtaacaga aaaaggagca 1080
atacctgcat tgcctacaaa agaagcagta cttaaaatat tggatggtgc cacagctaat 1140
tgatcaaatt atacatgccc tcataaaaat atgatacatt gcaccactta tgtaaaataa 1200
attttgtgga atattttagt ctataatatt attgctatcc cctgtacaaa atcatgtgga 1260
tataattcct ttttaaacat tttattttat ataatatata atat 1304

<210> SEQ ID NO 24
<211> LENGTH: 2725
<212> TYPE: DNA
<213> ORGANISM: Solanum lycopersicum
<300> PUBLICATION INFORMATION:
<308> DATABASE ACCESSION NUMBER: L19762
<309> DATABASE ENTRY DATE: 1994-06-20
<313> RELEVANT RESIDUES IN SEQ ID NO: (1)..(2725)

<400> SEQUENCE: 24
catttctttc ctctcaaagt tgaactttgt ctgaggattt cccatctgct gaatcaacta 60
taatggctga acgtgttctg actcgtgttc atagacttcg tgaacgtgtt gatgcaactt 120
tatgcgctca ccgcaatgag atactgctgt ttctttcaag gattgaaagc cacggaaaag 180
ggatcttgaa acctcacgag cttttggctg agttcgatgc aattcgccaa gatgacaaag 240
acaaactgaa tgaacatgcg ttcgaagaac tcctgaaatc cactcaggaa gcgattgttc 300 tgccccccttg ggttgcactt gctattcgtt tgaggcctgg tgtctgggaa tacgtccgtg 360
tgaacgtcaa tgcactagtt gttgaggagc tgtccgtccc tgagtatttg caattcaagg 420
aagaacttgt cgacggagcc tcaaatggaa atttcgttct cgagttggat ttcgagcctt 480
tcactgcatc ctttcctaaa ccaaccctca ccaaatctat tggaaatgga gttgaattcc 540
tcaataggca cctctctgcc aaaatgttcc atgacaagga aagcatggcc ccgcttctcg 600
aatttctccg cgctcaccat tataagggca agacaatgat gctgaatgat aggatacata 660
attcgaatac tcttcaaaat gtcctaagga aggcagagga atacctcatt atgcttcccc 720
cggaaactcc attttttgaa ttcgaacaca agttccaaga aatcggattg gagaagggat 780
ggggggacac ggcggagcgt gtgctagaga tggtgtgcat gcttcttgat ctccttgagg 840
cacctgactc atgtactctt gagaagttct tggggagaat tcctatggtc ttcaatgtgg 900
ttatcctttc ccctcatgga tattttgccc aagaaaatgt cttgggttat cccgacaccg 960
gtggccaggt tgtctacata ttagatcaag ttcccgcctt ggagcgtgaa atgcttaagc 1020
gcataaagga gcaaggactt gatatcatcc cccgtattct tattgttact cggctgctgc 1080
ccgatgcagt tggaaccact tgcggtcaga ggcttgagaa ggtgtatgga acagaacact 1140
cacatattct tagagtcccc tttgggactg agaagggtat cgttcgcaaa tggatctctc 1200
gctttgaagt gtggccatat atggagactt tcattgagga tgttgcaaaa gaaatatctg 1260
cagaattgca ggccaagcca gatttgataa tcggaaacta cagtgagggc aatcttgctg 1320
cttctttgtt agctcacaag ttaggcgtaa cgcagtgcac catcgcccat gccttggaga 1380
aaacgaaata tcctgattcc gacatttact ggaaaaagtt tgatgaaaaa taccatttct 1440
cgtcccagtt tacagctgat ctcattgcaa tgaatcacac tgatttcatc atcaccagca 1500
cattccagga gatagcagga agcaaggaca ctgtaggaca atatgagagc catatggcat 1560

```
ttacaatgcc tggattgtac agagttgttc atggcattaa tgtgttcgac cccaagttca   1620
acatcgtctc acctggagct gatattaacc tctacttccc gtactccgaa tcggaaaaga   1680
gacttacagc atttcaccct gaaattgatg agctgctgta cagtgacgtt gagaatgacg   1740
aacatctgtg tgtgctcaag gacaggacta agccaatttt attcacaatg gcaaggttgg   1800
atcgtgtgaa gaatttaacc ggacttgttg agtggtacgc caagaatcca cgactaaggg   1860
gattggttaa cctggtcgta gttggcggag atcgaaggaa ggaatccaaa gatttggaag   1920
agcaggcaga gatgaagaag atgtatgagc taatagagac tcataacttg aatggccaat   1980
tcagatggat ttcttcccag atgaaccgag tgaggaatgg tgagctctac cgatacattg   2040
ctgacactaa gggagctttt gtgcagcctg cattctacga ggcttttggt ctgactgttg   2100
tcgaagcaat gacttgtggt ctgcctacat ttgcaactaa tcacggtggt ccagctgaaa   2160
tcatcgttca tggaaaatcc ggtttccata ttgatccata tcacggtgag caagctgctg   2220
atctgctagc tgatttcttt gagaaatgca agaaagagcc ttcacattgg gaaaccattt   2280
cgacgggtgg tctgaagcgc atccaagaga agtacacttg gcaaatctac tccgaaagac   2340
tactgacact ggctgctgtt tatgggttct ggaaacatgt ttctaagctt gatcgtctag   2400
aaatccgtcg ctaccttgaa atgttttacg ctctcaagta ccgtaagatg gctgaagctg   2460
ttccattggc tgctgagtga atgaaggtct tcctgttttt tctttgaata aaaatgaagt   2520
ctttgacaag tagaggcttc tgtttagtgt ttcatttcca tttagtatcc cccccccac    2580
cccaccccac cccaccccct ttgctttatg ttgtattttt catttggtca tgtcaatgta   2640
ggttggagaa tttgagctgt tagtagtatg aataagagat caaaatttca atctataagt   2700
tatcaagaaa cattgttttg gtttg                                          2725
```

```
<210> SEQ ID NO 25
<211> LENGTH: 2708
<212> TYPE: DNA
<213> ORGANISM: Solanum lycopersicum
<300> PUBLICATION INFORMATION:
<308> DATABASE ACCESSION NUMBER: NM_001247875
<309> DATABASE ENTRY DATE: 2012-11-02
<313> RELEVANT RESIDUES IN SEQ ID NO: (1)..(2708)

<400> SEQUENCE: 25
```

```
tcctccatcc attacttccc tctatttatt attattcctt tcaatattcc tctctttcca     60
ttttattcat aaaaaataaa aactaaaaaa agttgaaagt catctgagga tttgcaggtg    120
caatggctca acgtgttcta actcgtgttc acagtcttcg tgaacgtctt gatgctactt    180
tggatgctca tcgcaatgaa attttgctct ttctttcaag gatcgaaagc cacgggaaag    240
ggatcttgaa acctcaccag ctactggctg agtttgaatc aattcagaaa gaagacaaag    300
acaaactgaa tgatcatgcc tttgaagaag tcctgaaatc cactcaggaa gcaattgttt    360
tgcccccatg ggttgcactt gctattcgtt tgaggcccgg tgtgtgggaa tatgtccgtg    420
tgaatgttaa tgctcttagt gttgaggagc tgactgtgcc tgagtttttg caattcaagg    480
aagaacttgt taacggaact tccagtgata actttgttct tgaattggat tttgagccct    540
tcactgcatc atttccaaaa ccaaccctca cgaaatcaat tggaaatgga gttgaattcc    600
tcaacaggca cctctctgct aaaatgttcc atgacaagga aagcatgacc cctcttctcg    660
agtttcttcg agttcaccac tacaatggaa agtcaatgat gctgaatgat agaattcaga    720
atttgtatac tctccaaaaa gtcctgagga aggccgagga atacctcacc accctttcgc    780
cagaaacttc atactcctca tttgagcaca agttccaaga aattggcttg gagagaggtt    840
```

```
ggggtgacac cgcagagcgt gttctagaga tgatctgcat gctcctggat ctccttgagg    900

ctcctgactc atgtactctt gagaagttcc ttagtagaat tcctatggtt ttcaatgtag    960

ttataccttc acctcatgga tatttcgccc aggaaaatgt cttgggttac cccgacactg   1020

gtggtcaggt tgtctatatt ttggatcaag ttcctgcctt ggagcgtgag atgctcaagc   1080

gcataaagga gcaaggactt gatatcaaac cgcgtattct tattgttact cggcttctcc   1140

ctgatgcagt tggtaccact tgtggtcagc gactcgagaa ggtatttgga actgagcatt   1200

cacatattct tagggtcccc tttaggactg aaaagggcat tgttcgcaaa tggatctctc   1260

gttttgaagt ctggccatac atggagactt tcattgagga tgtggggaaa gaaataaccg   1320

cagaactgca agctaagcca gatcttatta ttggaaacta tagtgaggga aaccttgcag   1380

cctccttgtt ggctcacaag ttaggtgtaa cacagtgcac cattgctcat gcattggaga   1440

aaaccaaata tcctgattct gacatttact tgaacaaatt tgacgagaaa taccacttct   1500

cagctcagtt cacagctgat cttatagcaa tgaatcatac tgatttcatt atcaccagca   1560

ccttccagga gatagcagga agcaaggaca ctgttggaca gtatgagagc cacatggcct   1620

tcacaatgcc tggattgtat agagttgttc atggcattga tgtgttcgac cccaaattca   1680

acattgtgtc accaggagct gatgtgaatc tctatttccc atactccgaa aaggaaaaga   1740

gattgacaac ttttcaccct gaaattgaag acttgctgtt tagcgatgtt gagaacgaag   1800

aacacctgtg tgtgttgaag gacaggaata agcccatcat attcaccatg gcaagattgg   1860

accgagtgaa gaacttaact ggacttgtcg agtggtatgc taagaatcca cgactaaggg   1920

agttggttaa ccttgtagtg gttggtggag accgaagaaa ggaatccaaa gacttggaag   1980

agcaggcaga gatgaagaag atgtatgaac ttataaagac tcacaatttg aatggccagt   2040

tccgatggat ttcttcccag atgaaccgcg tgaggaatgg ggaactctac aggtacattg   2100

ctgacacaag gggagctttc gtgcagcctg cattctacga ggctttcggt ctgactgttg   2160

ttgaggccat gagctgcggt ttgcctacat ttgcaactaa tcaaggtggt ccagctgaga   2220

tcatcgttca tggaaagtct ggtttccaaa ttgatccata ccatggcgag caggctgctg   2280

atctcctcgc tgagttcttc gagaaatgta aggtagaccc ttcacattgg gaagccattt   2340

ccaagggtgg ccttaagcgt atacaggaga agtacacatg gcaaatctac tccgaccggc   2400

tgttgacact agctgctgtt tacgggttct ggaagcacgt ttccaagctt gatcgtcttg   2460

aaattcgtcg ttatcttgag atgttttacg ctctcaaatt ccgcaagctg gctgaacttg   2520

tcccattggc tgttgagtaa attgacaaag aagagaaggt ttctgtctga ttgttatcca   2580

cattgtcctt tagaaattgt ttgccccaca tttgtatctg tttgagaact tcattgtctt   2640

tttcatttgc catttttccc ttctgtagtc atgaagagga ttgcaaattt gacattatgt   2700

agtgttag                                                            2708
```

<210> SEQ ID NO 26
<211> LENGTH: 2958
<212> TYPE: DNA
<213> ORGANISM: Solanum lycopersicum
<300> PUBLICATION INFORMATION:
<308> DATABASE ACCESSION NUMBER: HM180943
<309> DATABASE ENTRY DATE: 2012-09-01
<313> RELEVANT RESIDUES IN SEQ ID NO: (1)..(2958)

<400> SEQUENCE: 26

```
atatttatat gaatttaaag aagttgaaaa ccatattaac tcttttattt tttttaaaaa     60
```

-continued agaaattcat ttaatatgag aaaacttatt tcatttgagc ttgaattgac atcctccaag 120
gatgaaataa agaaattttt tttattaccc gaaatcgacc gttttggaat ccgttgaatg 180
tattctatct attttgttgt tgtaattgga aaatgtcgaa tccaaagttg tcaagaatac 240
ctagtatgag agagagagtt gaggatactc tctctgctca ccgtaatcag ctagtggctc 300
tcctatccag atatgtggcg caggggaagg ggatattgca gcctcatcat ttaattgatg 360
agctgaataa tgctgtatgt gatgacactg cttgtgaaaa gctgaaagaa ggcccctttt 420
gtgaaatctt gaaatctact caggaagcca ttgtgctccc accatttgtt gctatagcag 480
ttcgtccaag gccaggtgtt tgggaatatg ttcgtgtgaa cgtatatgat ctgagcgttg 540
aacaattgac ggttcctgaa tatctccgtt tcaaagaaga acttgtcgat ggagaggatc 600
ataatcatct ttttgtgctt gagctggatt ttgagccatt taatgcatca gttcctcgtc 660
cctcacgctc ttcatccatt ggaaatggag tacaattcct caatcgtcat ttgtcctcaa 720
atatgtttcg cagcaacgaa tccctcgacc cattacttga tttccttaga ggacacaatc 780
ataaagggaa tgtcttgatg ttgaatgaac gtatacagcg aatctccagg ctggagtcgt 840
ctcttaataa ggcagatgat tatctctcaa agctaccacc agatacaccc tatactgact 900
ttgaatatgc attgcaggaa atgggctttg agaaaggttg gggtgatact gcaaatcgtg 960
ttttggagac tatgcatctg ctttctgaca ttcttcaggc tcctgatccc tcaaccttag 1020
agacttttct tggtagatta ccaatggtgt ttaatgttgt catattatct cctcatggat 1080
actttggtca agcaaatgtc ttgggtttgc cggacactgg tggacaggtt gtctatatac 1140
tggatcaagt gcgtgctttg gaggccgaaa tgcttcttag aataaagcaa caaggactca 1200
acttcaagcc tagaatcctt gttgtcaccc gactgatacc tgatgctaaa ggaaccacgt 1260
gcaaccagcg gttggagaga attagtggaa ctgaatactc gcatatttta cgtgtccctt 1320
ttaggacaga aaatggaatc cttcataaat ggatatctag gtttgatgta tggccttacc 1380
tggagaagtt tactgaggac gtggcaggtg aaatgtctgc tgagctccag ggagtgcctg 1440
atctgattat tggcaactac agtgatggaa atttagttgc ctccctgtta gcatataaaa 1500
tgggcatcac acagtgtacc attgctcatg ctttggagaa aacaaagtat cctgattctg 1560
acatctattg gaaaaagttt gaggagaaat atcatttttc atgtcagttt actgctgacc 1620
tactgtcaat gaatcattca gatttcataa tcactagtac ctatcaagag attgcaggaa 1680
cgaagaatac tgttggtcag tacgagagtc atactgcttt cactctccca ggcctatatc 1740
gtgttgtcca tggcattgat gtcttcgatc ccaaattcaa tatagtgtct cctggagctg 1800
acatgacaat ttacttccca tattttgaca aggaaaagag actgacatct ttgcatccct 1860
cgattgagaa gttgttattt gatcctgagc agaatgaagt gcatataggc agcctgaatg 1920
atcaatcaaa accgataatt ttttcaatgg caaggcttga ccgggtaaag aacattaccg 1980
gattagttga gtgctatgct aaaaatgcca cactcaggga actggctaac cttgttgtag 2040
tagctggata caacgatgta aagaaatcca atgatagaga agaaatagca gaaattgaga 2100
agatgcatgc tcttatgaag gaacataact tggatggtca attcagatgg atatcagccc 2160
aaatgaaccg ggcacgtaat ggtgagctct atcgctatat agctgacaag agaggtatat 2220
ttgttcagcc tgcgtattat gaagcgtttg gactgacggt ggttgaagct atgacttgtg 2280
gtcttccaac atttgcaact tgtcatggtg gacctatgga gatcattcag gacggtgtat 2340
ccgggtacca tatagatcct tatcatccca ataaagctgc tgagctcatg gtagaattct 2400
tccaacgatg cgaacaaaat cctactcact gggaaaatat atctgcatct ggcctacaaa 2460
ggattctcga caggtataca tggaaaattt actcggagag gctgatgact ttggctggtg 2520
tatatggttt ctggaagctt gtttcaaaac tcgagaggcg tgaaactaga cgatacctcg 2580
agatgttcta cattctcaag ttccgtgagt tggtaaaatc tgttcctcta gcagttgatg 2640
agaagcagtg aggattttgc aaaggaataa ataacgtgga gcataccact ctatctatga 2700
taattttttt tttgttcttc ttgtttgttg tgtagttaaa ctaattaagt gcactgagtt 2760
tctaatagat ctcaaatagc taaacgttac tatctcctat tttaatagcg ctatacttta 2820
atttgtcaaa tacaaatcag tgatccaata tgctgaattt atttagaatt gaaaaaggat 2880
gtcatcttca tcttgatagt cttaaacagg caagcacggt tgattttcta tcttaactat 2940
ataaccattc tttaatta 2958

<210> SEQ ID NO 27
<211> LENGTH: 22
<212> TYPE: DNA
<213> ORGANISM: Solanum lycopersicum
<300> PUBLICATION INFORMATION:
<308> DATABASE ACCESSION NUMBER: U64817
<309> DATABASE ENTRY DATE: 1996-07-22
<313> RELEVANT RESIDUES IN SEQ ID NO: (1)..(22)

<400> SEQUENCE: 27
ctccgttaca tatctgatcc tt 22

<210> SEQ ID NO 28
<211> LENGTH: 20
<212> TYPE: DNA
<213> ORGANISM: Solanum lycopersicum
<300> PUBLICATION INFORMATION:
<308> DATABASE ACCESSION NUMBER: U64817
<309> DATABASE ENTRY DATE: 1996-07-22
<313> RELEVANT RESIDUES IN SEQ ID NO: (1)..(20)

<400> SEQUENCE: 28
gacagcattg aagtcacctt 20

<210> SEQ ID NO 29
<211> LENGTH: 21
<212> TYPE: DNA
<213> ORGANISM: Solanum lycopersicum
<300> PUBLICATION INFORMATION:
<308> DATABASE ACCESSION NUMBER: U64818
<309> DATABASE ENTRY DATE: 1996-07-22
<313> RELEVANT RESIDUES IN SEQ ID NO: (1)..(21)

<400> SEQUENCE: 29
ttgttggtgc ccttctaacc a 21

<210> SEQ ID NO 30
<211> LENGTH: 23
<212> TYPE: DNA
<213> ORGANISM: Solanum lycopersicum
<300> PUBLICATION INFORMATION:
<308> DATABASE ACCESSION NUMBER: U64818
<309> DATABASE ENTRY DATE: 1996-07-22
<313> RELEVANT RESIDUES IN SEQ ID NO: (1)..(23)

<400> SEQUENCE: 30
acgatgtttc tatgctcctc cct 23

<210> SEQ ID NO 31
<211> LENGTH: 24
<212> TYPE: DNA

<213> ORGANISM: Solanum lycopersicum
<300> PUBLICATION INFORMATION:
<308> DATABASE ACCESSION NUMBER: AY099454
<309> DATABASE ENTRY DATE: 2002-10-02
<313> RELEVANT RESIDUES IN SEQ ID NO: (1)..(24)

<400> SEQUENCE: 31
gacatttaca tggatgagaa gaaa 24

<210> SEQ ID NO 32
<211> LENGTH: 22
<212> TYPE: DNA
<213> ORGANISM: Solanum lycopersicum
<300> PUBLICATION INFORMATION:
<308> DATABASE ACCESSION NUMBER: AY099454
<309> DATABASE ENTRY DATE: 2002-10-02
<313> RELEVANT RESIDUES IN SEQ ID NO: (1)..(22)

<400> SEQUENCE: 32
gctgtggcac catccaatat tt 22

<210> SEQ ID NO 33
<211> LENGTH: 20
<212> TYPE: DNA
<213> ORGANISM: Solanum lycopersicum
<300> PUBLICATION INFORMATION:
<308> DATABASE ACCESSION NUMBER: U60482
<309> DATABASE ENTRY DATE: 1997-01-11
<313> RELEVANT RESIDUES IN SEQ ID NO: (1)..(20)

<400> SEQUENCE: 33
caccattggg tctgagcgat 20

<210> SEQ ID NO 34
<211> LENGTH: 20
<212> TYPE: DNA
<213> ORGANISM: Solanum lycopersicum
<300> PUBLICATION INFORMATION:
<308> DATABASE ACCESSION NUMBER: U60482
<309> DATABASE ENTRY DATE: 1997-01-11
<313> RELEVANT RESIDUES IN SEQ ID NO: (1)..(20)

<400> SEQUENCE: 34
gggcgacaac cttgatcttc 20

<210> SEQ ID NO 35
<211> LENGTH: 20
<212> TYPE: DNA
<213> ORGANISM: Solanum lycopersicum
<300> PUBLICATION INFORMATION:
<308> DATABASE ACCESSION NUMBER: U60482
<309> DATABASE ENTRY DATE: 1997-01-11
<313> RELEVANT RESIDUES IN SEQ ID NO: (1)..(20)

<400> SEQUENCE: 35
gtggtgcatt gaccgtgatg 20

<210> SEQ ID NO 36
<211> LENGTH: 24
<212> TYPE: DNA
<213> ORGANISM: Solanum lycopersicum
<300> PUBLICATION INFORMATION:
<308> DATABASE ACCESSION NUMBER: U60482
<309> DATABASE ENTRY DATE: 1997-01-11
<313> RELEVANT RESIDUES IN SEQ ID NO: (1)..(24)

<400> SEQUENCE: 36
ggtcggatgg atattatgca actg 24

-continued

```
<210> SEQ ID NO 37
<211> LENGTH: 20
<212> TYPE: DNA
<213> ORGANISM: Eucalyptus globulus
<300> PUBLICATION INFORMATION:
<308> DATABASE ACCESSION NUMBER: AY263810
<309> DATABASE ENTRY DATE: 2003-05-12
<313> RELEVANT RESIDUES IN SEQ ID NO: (1)..(20)

<400> SEQUENCE: 37

gaagcggcac agaaaggtcc                                                   20


<210> SEQ ID NO 38
<211> LENGTH: 20
<212> TYPE: DNA
<213> ORGANISM: Eucalyptus globulus
<300> PUBLICATION INFORMATION:
<308> DATABASE ACCESSION NUMBER: AY263810
<309> DATABASE ENTRY DATE: 2003-05-12
<313> RELEVANT RESIDUES IN SEQ ID NO: (1)..(20)

<400> SEQUENCE: 38

ccgaagccat acagggtcct                                                   20


<210> SEQ ID NO 39
<211> LENGTH: 16
<212> TYPE: DNA
<213> ORGANISM: Gossypium hirsutum

<400> SEQUENCE: 39

ttgcattggc cgtgag                                                       16


<210> SEQ ID NO 40
<211> LENGTH: 20
<212> TYPE: DNA
<213> ORGANISM: Gossypium hirsutum

<400> SEQUENCE: 40

gcaagtcctc aatttctggg                                                   20
```

USE OF FRUCTOKINASES AND SUCROSE SYNTHASES FOR INCREASING CELL WALL POLYMERS

DESCRIPTION OF THE STATE OF THE ART

Plant cell walls are the primary constituents of many plant products including wood. Wood is being used for many commercial purposes such as pulp for the paper industry, energy production and construction. Wood is composed primarily from cell walls of the secondary xylem which includes the plant vascular tissues. Cell wall synthesis is entirely dependent on sugar metabolism. Some of the sugar (usually sucrose) transported in the vascular tissues is being used for production and development of the wood.

Most FRKs are expressed in vascular tissues and affect vascular development. Specifically, increased expression of FRK2, the major FRK in vascular tissues of tomato plants, enhanced cellulose and lignin synthesis and increased cell wall content. FRK1, which unlike FRK2, is not inhibited by increasing concentrations of fructose further enhances cell wall synthesis.

Sucrose synthase (SuSy) which cleaves sucrose into UDP-glucose and fructose, is the major sucrose cleaving enzyme in vascular tissues. Applicants found that SuSy and FRK are co-expressed in vascular tissues. Similar to FRK2, SuSy enzymatic activity is feedback inhibited by its end-product, fructose. Fructose released from the cleavage of sucrose by SuSy inhibits and down regulates SuSy activity. As a consequence, the amount of sucrose allocated for vascular and xylem development is restricted by the accumulating fructose. Thus, increased activity of FRK that phosphorylates fructose and lowers fructose concentration would enhance SuSy activity and allocation of sucrose to vascular and xylem development.

Two major components of vascular tissues are xylem and phloem. Xylem transports water and minerals from roots to shoot, while phloem translocates sugars from source (leaves) to sink (non-photosynthetic) tissues. In many plants, the transported sugar is primarily sucrose. Some of the transported sucrose is being cleaved in the vascular tissues to support vascular development.

Cell walls are comprised primarily of polymers of simple sugar monomers linked in a variety of linear or branched polymers known as polysaccharides. The most abundant simple sugar monomer is glucose, and the most abundant polymer is cellulose. Cellulose is a linear, unbranched polymer, comprised of .beta.-1,4 linked glucose monomers. Other polysaccharides found in plant cell walls include hemicelluloses, which comprise a group of polysaccharides composed of .beta.-1,4 linked glucose monomers having side chains which may include sugars other than glucose, including xylose, fucose, arabinose, and galactose. Hemicelluloses are a heterogeneous mixture of polysaccharides, the composition of which varies substantially for different plants. Hemicelluloses are defined, operationally, as that polymer fraction which may be extracted from the cell wall with alkali.

The secondary walls may comprise a considerable amount of lignin in addition to cellulose, pectins and hemicelluloses. Lignin is an insoluble polymer that is primarily responsible for the rigidity of plant stems. Specifically, lignin serves as a matrix around the polysaccharide components of some plant cell walls. In general, the higher the lignin content, the more rigid the plant. For example, tree species synthesize large quantities of lignin, with lignin constituting between 20% to 30% of the dry weight of wood. The lignin content of grasses ranges from 2-8% of dry weight and changes during the growing season. In addition to providing rigidity, lignin aids in water transport within plants by rendering cell walls hydrophobic and water impermeable. Lignin also plays a role in disease resistance of plants by impeding the penetration and propagation of pathogenic agents.

Secondary cell walls form after cessation of cell growth and enlargement. Unlike primary cell walls, secondary cell walls can adopt highly specialized structures and compositions. For example, xylem cells, such as those found in wood, have thickened secondary walls that are strengthened by lignin.

Sucrose, a disaccharide, can be cleaved by either sucrose synthase (SuSy), likely the main sucrose cleaving enzyme in the vascular system, into UDP-glucose and fructose, or by invertase into glucose and fructose (Koch 2004). Consequently, fructose is destined to be one of the most abundant monosaccharides produced through the cleavage of sucrose.

While UDP-glucose is immediately available for cellulose synthesis, free fructose must first be phosphorylated by either hexokinase (HXK) or fructokinase (FRK) for further metabolism. In the absence HXK or FRK the accumulating fructose might cause feedback inhibition of SuSy activity, reducing sucrose cleavage (Schaffer and Petreikov 1997a). HXK and FRK are distinguished by their substrate specificities and affinities (Granot 2007). HXK may phosphorylate both glucose and fructose, but its affinity to fructose is two orders of magnitude lower than its affinity to glucose, as well as two orders of magnitude lower than the affinity of FRK to fructose. Thus fructose is likely to be primarily phosphorylated by FRK (Granot 2007).

FRKs and SuSys exist in all plants examined so far and are probably obligatory in plants. They exist in perennials and annuals, gymnosperm and angiosperm, dicots and monocots, trees, bushes and grasses, as well as all crops studied. For example they exist in aspen, cotton, tomato, sugar beet, potato, soybean, barely, avocado, spinach, lily, camellia, pea, maize, rice, melon and *Arabidopsis*. Goren et al. 2011, shows the existence of sucrose synthase in numerous species (FIG. 2, Table 2 and the supplemental FIG. 1 in Goren et al. 2011).

Tomato is a species in which four FRK genes, FRK1-4, have been cloned and characterized (Dai et aL 2002, Damari-Weissler et aL 2006, Damari-Weissler et aL 2009, German et al. 2004, German et al. 2003, Granot 2007, Odanaka et al. 2002). FRK1, FRK2 and FRK3 are expressed in all plant parts examined (German et al., 2004), while FRK4 is expressed only in stamens (German et al. 2002). FRK2 and FRK3 enzymes, as mentioned above, manifest substrate inhibition. They are inhibited by their own substrate, fructose, when its concentration exceeds 1 mM (Dai et al. 1997, German et al., Granot 2004, Petreikov et al. 2001). FRK1 activity, on the other hand, is not inhibited by fructose.

Sucrose synthase (SuSy), which cleaves sucrose into UDP-glucose and fructose, is the major sucrose cleaving enzyme in vascular tissues. Western blot analysis of tomato SuSy protein showed an increasing SuSy expression gradient along the developmental axis of the tomato stem, with the protein concentrated mainly in the xylem tissue of the stem (Goren et al. 2011). SuSy1, the major SuSy gene in tomato plants, and FRK2 are co-expressed in vascular tissues.

Similar to FRK2, SuSy activity is also inhibited by fructose (a phenomenon of product inhibition or feedback inhibition) and therefore, fructose released from the cleavage of sucrose by SuSy inhibits SuSy activity. As a consequence, the amount of sucrose allocated for vascular and xylem development is restricted by the accumulating fructose.

The tomato FRK2 (LeFRK2) is the major fructokinase gene expressed in most tissues, including stems, roots and leaves (German et al., 2004, German et al., 2002, Kanayama et al. 1997, Kanayama et al. 1998). To study the role of LeFRK2 in tomato plants, Applicants previously generated and analyzed transgenic tomato plants with antisense suppression or co-suppression of LeFRK2 (Dai at al., 2002, German et al., 2003). These antisense plants exhibited growth inhibition and wilting of young leaves during the day. Triple-grafting experiments, in which an antisense interstock replaced a portion of the wild-type stem, demonstrated that an antisense interstock is sufficient to inhibit growth and cause leaf wilting, suggesting that LeFRK2 is required for proper stem functioning. Furthermore, the cumulative area of active xylem in stems of antisense plants was smaller than that of wild-type plants, suggesting that LeFRK2 is required for stem xylem development. Applicants showed that suppression of LeFRK2 results in a significant reduction in the size of vascular cells and slowed fiber maturation. The xylem vessels in stems of LeFRK2-antisense plants were narrower than in WT plants and have thinner secondary cell walls. Although the cambium produces rounded secondary vessels, these vessels become deformed during the early stages of xylem maturation. Water conductance is then reduced in stems, roots and leaves, suggesting that LeFRK2 influences xylem development throughout the entire vascular system. Suppression of LeFRK2 reduced also the length and width of the sieve (phloem) elements.

Applicants have discovered that fructokinases (FRKs) (fructose phosphorylating enzymes) are the major enzymes regulating the amount of sugars directed toward wood development. Plants have several FRK isozymes with different intracellular location and biochemical characteristics. Sucrose metabolism using FRK and SuSy has an end effect on increased cellulose and lignin (cell wall polymers) production through its effect on carbon partitioning, The over-expression of FRK or the simultaneous over-expression of FRK and SuSy results in enhanced cell wall polymer deposition.

There exists a need for efficiently using genes that regulate plant cell wall synthesis and development. FRKs, alone or with SuSy may be used to increase cellulose, cell wall and wood production in commercial plants, especially in trees and plants used for biomass production.

SUMMARY OF THE INVENTION

The invention relates to transgenic plants exhibiting enhanced growth of plant and plant cell wall. It has been found that increased expression of FRK and increased co-expression of both SuSy and FRK further accelerates sucrose cleavage and allocation of sugars to vascular and xylem development resulting in thickened secondary cell wall.

In one embodiment, transgenic plants engineered to over-express fructokinases (FRKs) are provided. The FRK-transgenic plants of the invention consistently exhibit enhanced plant growth rate and increased biomass and cell wall characteristics.

In another embodiment, transgenic plants engineered to over-express both fructokinases (FRKs) and sucrose synthase (SUS) are provided. The FRK+SUS double-transgenic plants of the invention consistently exhibit enhanced plant growth rate and increased biomass and cell wall characteristics. According to the present invention, transgenic plants exhibiting such enhanced cell wall-growth phenotypic characteristics are generated with several individual plant species, using various transformation methodologies, different expression vectors and promoters, and heterologous transgene sequences from a variety of species.

Applicants have identified that increased expression of the enzyme fructokinase (FRK) is directly involved in the increase of the plant's growth rate, biomass and cell wall content. This aspect of the invention is exemplified herein by the overexpression of FRK in several species, including tomato, and *Eucalyptus*, which have been expressed as recombinant FRKs and confirmed as having FRK activity.

The invention further provides transgenic plants which express both a nucleic acid that encodes for FRK (FRK transgene) and a nucleic acid that encodes for sucrose synthase, SuSy (SuSy transgene). The expression of these two transgenes in such "double-transgene" plants results in a growth enhancing effect, as these plants exhibit. Methods for the generation of such growth-enhanced transgenic plants are provided.

By preferentially increasing the concentration of phosphorylated sugar (i.e., in xylem tissues), the transgenic plants of the invention are capable of producing higher overall yields over shorter periods of time, and therefore may provide agricultural industries with enhanced productivity across a wide range of crops. The enhanced growth characteristics of the transgenic plants of the invention is achieved essentially by introducing additional FRK and SuSy capacity into the plant.

In one embodiment, the invention provides a transgenic plant comprising a nucleic acid that encodes for FRK and a nucleic acid that encodes for SuSy, wherein each of said nucleic acids are operably linked to a plant promoter. In a specific embodiment, the FRK is a FRK1. In another specific embodiment, the first nucleic acid (FRK transgene) encodes a polypeptide having an amino acid sequence selected from the group consisting of (a) SEQ ID NO: 2; SEQ ID NO: 4; SEQ ID NO: 3, and (b) an amino acid sequence that is at least 40% identical to any one of SEQ ID NO: 2; SEQ ID NO: 4; SEQ ID NO: 3 and has FRK activity. In yet another specific embodiment, the second nucleic acid (SuSy transgene) encodes a polypeptide having an amino acid sequence selected from the group consisting of (a) SEQ ID NO: 5, SEQ ID NO: 1, SEQ ID NO: 17, SEQ ID NO: 6, SEQ ID NO: 7, and SEQ ID NO: 8 and (b) an amino acid sequence that is at least 40% identical to SEQ ID NO: 5, SEQ ID NO: 1, SEQ ID NO: 17, SEQ ID NO: 6, SEQ ID NO: 7, and SEQ ID NO: 8. In some embodiments, the FRK and SuSy transgenes are incorporated into the genome of the plant. The transgenic plant of the invention may be a monocotyledonous or a dicotyledonous plant. The transgenic plant of the invention may be a tree.

The scope of the invention also includes progeny of any generation of the transgenic plants of the invention, wherein said progeny comprises a nucleic acid that encodes for FRK (FRK transgene) and a nucleic acid that encodes for SuSy (SuSy transgene), as well as a seed of any generation of the transgenic plants of the invention, wherein said seed comprises said. FRK transgene and said SuSy transgene. The transgenic plants of the invention may display one or more enhanced growth characteristics rate when compared to an analogous wild-type or untransformed plant, including without limitation increased growth rate, biomass yield, cell wall content, and may also display increased levels of FRK and/or SuSy activity, and/or increased levels of phosphorylated fructose.

Methods for producing the transgenic plants of the invention and seeds thereof are also provided, including methods for producing a plant having enhanced growth properties, increased biomass yield and increased cell wall content.

BRIEF DESCRIPTION OF THE FIGURES

The accompanying drawings, which are incorporated herein and form a part of the specification, illustrate non-limiting embodiments of the present invention, and together with the description, serve to explain the principles of the invention.

In the Figures.

DETAILED DESCRIPTION OF THE INVENTION

Figure 1:
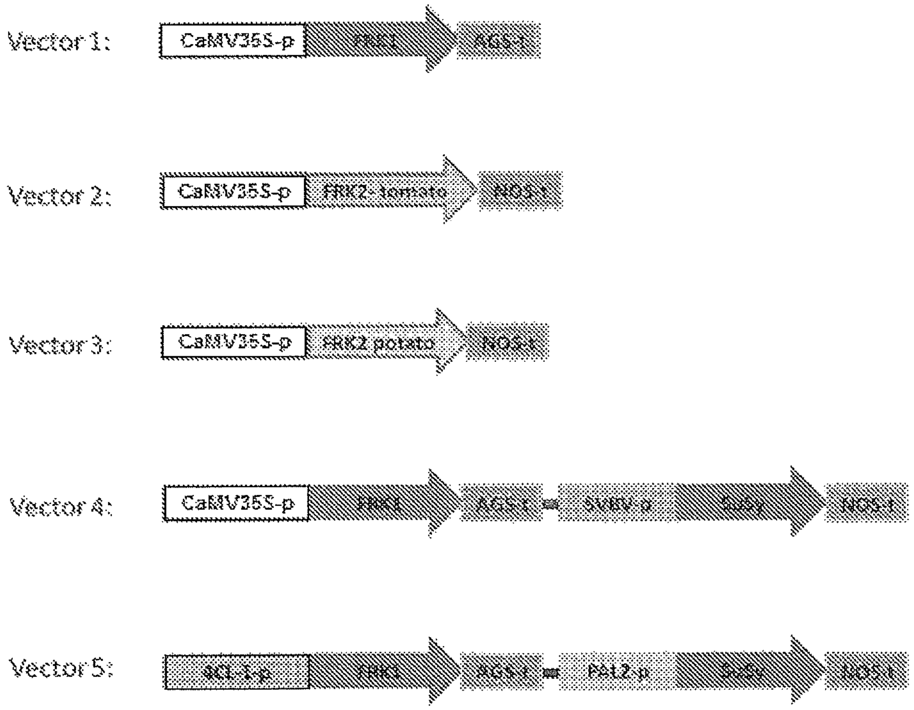
FIG. 1 shows FRK1 & 2 and SuSy vectors used for transformation.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 3rd. edition (2001) Cold Spring Harbor Laboratory Press, Cold Spring Harbor, N.Y.; Current Protocols in Molecular Biology (Ausbel et al., eds., John Wiley & Sons, Inc. 2001; Transgenic Plants: Methods and Protocols (Leandro Penak, ed., Humana Press, 1.sup.st edition, 2004); and, *Agrobacterium* Protocols (Wan, ed., Humana Press, 2.sup.nd edition, 2006). As appropriate, procedures involving the use of commercially available kits and reagents are generally carried out in accordance with manufacturer defined protocols and/or parameters unless otherwise noted.

The terms "FRK polynucleotide" and "FRK nucleic acid" and "nucleic acid that encodes for FRK" are used interchangeably herein, and refer to a full length or partial length polynucleotide sequence of a gene which encodes a fructokinase protein involved in catalyzing the phosphorylation of fructose, and includes polynucleotides containing both translated (coding) and un-translated sequences, as well as the complements thereof. The term "FRK coding sequence" refers to the part of the gene which is transcribed and encodes a FRK protein. A "FRK transgene" is a nucleic acid molecule comprising a FRK polynucleotide which is exogenous to transgenic plant, plant embryo or progeny, organ or seed, harboring the nucleic acid molecule, or which is exogenous to an ancestor plant, plant embryo or progeny, organ or seed thereof, of a transgenic plant harboring the FRK polynucleotide.

The terms "SuSy polynucleotide" and "SuSy nucleic acid" and "nucleic acid that encodes for SuSy" are used interchangeably herein, and refer to a full length or partial length polynucleotide sequence of a gene which encodes a sucrose synthase protein, and includes polynucleotides containing both translated (coding) and un-translated sequences, as well as the complements thereof. The term "SuSy coding sequence" refers to the part of the gene which is transcribed and encodes a SuSy protein.

A "SuSy transgene" is a nucleic acid molecule comprising a SuSy polynucleotide which is exogenous to transgenic plant, or plant embryo, organ or seed, harboring the nucleic acid molecule, or which is exogenous to an ancestor plant, or plant embryo, organ or seed thereof, of a transgenic plant harboring the SuSy polynucleotide.

In employing the FRK or SuSy polynucleotides of the invention in the generation of transformed cells and transgenic plants, one of skill will recognize that the inserted polynucleotide sequence need not be identical, but may be only "substantially identical" to a sequence of the gene from which it was derived, or have the same enzymatic activity, as further defined below. The term FRK or SuSy polynucleotide specifically encompasses such substantially identical variants. Similarly, one of skill will recognize that because of codon degeneracy, a number of polynucleotide sequences will encode the same polypeptide, and all such polynucleotide sequences are meant to be included in the term FRK or SuSy polynucleotide. In addition, the term specifically includes those sequences substantially identical (determined as described below) with an FRK or SuSy polynucleotide sequence disclosed herein and that encode polypeptides that are either mutants of wild type FRK or SuSy polypeptides or retain the function of the FRK or SuSy polypeptide (e.g., resulting from conservative substitutions of amino acids in a FRK SuSy polypeptide). The term "FRK or SuSy polynucleotide" therefore also includes such substantially identical variants.

The term "heterologous" when used with reference to portions of a nucleic acid indicates that the nucleic acid comprises two or more subsequences that are not found in the same relationship to each other in nature. For instance, a nucleic acid is typically recombinantly produced, having two or more sequences from unrelated genes arranged to make a new functional nucleic acid, e.g., a nucleic acid encoding a protein from one source and a nucleic acid encoding a peptide sequence from another source.

"Overexpression" of either FRK or SuSy is any mRNA expression which is higher than the regular expression level of the corresponding endogenous native genes. "Higher" may by any percentage, so far the increase is statistically significant.

The term "functional variant" of a certain FRK protein is a protein having an amino acid sequence with less than 100% sequence identity to that certain FRK protein and that exhibits a fructose phosphorylation activity.

The term "functional variant" of a certain SuSy protein is a protein having an amino acid sequence with less than 100% sequence identity to that certain SuSy protein and that exhibits independent cleavage of sucrose into UDP-glucose and fructose.

"FRK increased activity" of a transformed plant means that fructose phosphorylation activity per protein unit extracted from the transformed plant is higher than that of the control non-transformed plant. "Higher" may by any percentage, so far the increase is statistically significant.

"SuSy increased activity" of a transformed plant means that cleavage of sucrose by SuSy per protein unit extracted from the transformed plant is higher than that of the control non-transformed plant. "Higher" may by any percentage, so far the increase is statistically significant.

The terms "identical" or percent "identity," in the context of two or more nucleic acids or polypeptide sequences, refer to two or more sequences or subsequences that are the same or have a specified percentage of amino acid residues or nucleotides that are the same (i.e., about 40% identity, preferably 50%, 55%, 60%, 65%, 70%, 75%, 80%, 85%, 90%, or 95% identity over a specified region, when compared and aligned for maximum correspondence over a comparison window, or designated region as measured using a sequence comparison algorithms, or by manual alignment and visual inspection. This definition also refers to the complement of a test sequence, which has substantial sequence or subsequence complementarity when the test sequence has substantial identity to a reference sequence. This definition also refers to the complement of a test sequence, which has substantial sequence or subsequence complementarity when the test sequence has substantial identity to a reference sequence.

It is of importance to note that FRKs from different plants may have less than 50% identity and still have a FRK activity.

When percentage of sequence identity is used in reference to polypeptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the polypeptide. Where sequences differ in conservative substitutions, the percent sequence identity may be adjusted upwards to correct for the conservative nature of the substitution.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, 1981, Adv. Appl. Math. 2:482, by the homology alignment algorithm of Needleman & Wunsch, 1970, J. Mol. Biol. 48:443, by the search for similarity method of Pearson & Lipman, 1988, Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

A preferred example of algorithm that is suitable for determining percent sequence identity and sequence similarity are the BLAST and BLAST 2.0 algorithms, which are described in Altschul et al., 1977, Nuc. Acids Res. 25:3389-3402 and Altschul et al., 1990, J. Mol. Biol. 215:403-410, respectively. BLAST and BLAST 2.0 are used, typically with the default parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4 and a comparison of both strands. For amino acid sequences, the BLASTP program uses as defaults a word length of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

Genomic DNA or cDNA comprising FRK polynucleotides may be identified in standard Southern blots under stringent conditions using the FRK polynucleotide sequences disclosed here. For this purpose, suitable stringent conditions for such hybridizations are those which include a hybridization in a buffer of 40% formamide, 1M NaCl, 1% SDS at 37° C., and at least one wash in 0.2×SSC at a temperature of at least about 50° C., usually about 55° C. to about 60° C., for 20 minutes, or equivalent conditions. A positive hybridization is at least twice background. Those of ordinary skill will readily recognize that alternative hybridization and wash conditions may be utilized to provide conditions of similar stringency.

Applicants have demonstrated that over-expression of the fructokinase gene in a transformed heterologous plant results in enhanced fructose phosphorylation rates and increased growth characteristics. Over-expression of a transgene comprising the FRK coding sequence in transgenic *Eucalyptus* plants also results in increased fructose phosphorylation. These transgenic plants also grow faster than wild-type plants. Similarly, in preliminary studies conducted with tomato plants (see Example 4), tomato plants transformed with the potato FRK transgene showed significant enhancement of growth rate, flowering, and seed yield in relation to wild type control plants.

The invention also provides methods of generating a transgenic plant having enhanced growth and other agronomic characteristics. In one embodiment, a method of generating a transgenic plant having enhanced cell wall content and other agronomic characteristics comprises introducing into a plant cell an expression cassette comprising a nucleic acid molecule encoding a FRK transgene, under the control of a suitable promoter capable of driving the expression of the transgene, so as to yield a transformed plant cell, and obtaining a transgenic plant which expresses the encoded FRK. In another embodiment, a method of generating a transgenic plant having enhanced growth and other agronomic characteristics comprises introducing into a plant cell one or more nucleic acid constructs or expression cassettes comprising nucleic acid molecules encoding a FRK transgene and a SuSy transgene, under the control of one or more suitable promoters (and, optionally, other regulatory elements) capable of driving the expression of the transgenes, so as to yield a plant cell transformed thereby, and obtaining a transgenic plant which expresses the FRK and SuSy transgenes.

Transgene Constructs/Expression Vectors

In order to generate the transgenic plants of the invention, the gene coding sequence for the desired transgene(s) must be incorporated into a nucleic acid construct (also interchangeably referred to herein as a/an (transgene) expression vector, expression cassette, expression construct or expressible genetic construct), which can direct the expression of the transgene sequence in transformed plant cells. Such nucleic acid constructs carrying the transgene(s) of interest may be introduced into a plant cell or cells using a number of methods known in the art, including but not limited to *Agrobacterium* mediated transformation, electroporation, DNA bombardment or biolistic approaches, microinjection, and via the use of various DNA-based vectors such as *Agrobacterium tumefaciens* and *Agrobacterium rhizogenes* or other binary vectors vectors. Once introduced into the transformed plant cell, the nucleic acid construct may direct the expression of the incorporated transgene(s) (i.e., FRK), either in a transient or stable fashion. Stable expression is preferred, and is achieved by utilizing plant transformation vectors which are able to direct the chromosomal integration of the transgene construct. Once a plant cell has been successfully transformed, it may be cultivated to regenerate a transgenic plant.

A large number of expression vectors suitable for driving the constitutive or induced expression of inserted genes in transformed plants are known. In addition, various transient expression vectors and systems are known. To a large extent, appropriate expression vectors are selected for use in a particular method of gene transformation. Broadly speaking, a typical plant expression vector for generating transgenic plants will comprise the transgene of interest under the expression regulatory control of a promoter, a selectable marker for assisting in the selection of transformants, and a transcriptional terminator sequence.

More specifically, the basic elements of a nucleic acid construct for use in generating the transgenic plants of the invention are: a suitable promoter capable of directing the functional expression of the transgene(s) in a transformed plant cell, the transgene (s) (i.e., FRK coding sequence) operably linked to the promoter, preferably a suitable transcription termination sequence (i.e., nopaline synthetic enzyme gene terminator) operably linked to the transgene, and sometimes other elements useful for controlling the expression of the transgene, as well as one or more selectable marker genes suitable for selecting the desired transgenic product (i.e., antibiotic resistance genes).

As *Agrobacterium tumefaciens* is the primary transformation system used to generate transgenic plants, there are numerous vectors designed for *Agrobacterium* transformation. For stable transformation, *Agrobacterium* systems utilize "binary" vectors that permit plasmid manipulation in both *E. coli* and *Agrobacterium*, and typically contain one or more selectable markers to recover transformed plants (Hellens et al, 2000, Technical focus: A guide to *Agrobacterium* binary Ti vectors. Trends Plant Sci 5:446-451). Binary vectors for use in *Agrobacterium* transformation systems typically comprise the borders of T-DNA, multiple cloning sites, replication functions for *Escherichia coli* and *A. tumefaciens*, and selectable marker and reporter genes.

Transcription Terminators

In preferred embodiments, a 3' transcription termination sequence is incorporated downstream of the transgene in order to direct the termination of transcription and permit correct polyadenylation of the mRNA transcript. Suitable transcription terminators are those which are known to function in plants, including without limitation, the nopaline synthase (NOS) and octopine synthase (OCS) genes of *Agrobacterium tumefaciens*, the T7 transcript from the octopine synthase gene, the 3' end of the protease inhibitor I or II genes from potato or tomato, the CaMV 35S terminator, the tm1 terminator and the pea rbcS E9 terminator. In addition, a gene's native transcription terminator may be used.

Selectable Markers

Selectable markers are typically included in transgene expression vectors in order to provide a means for selecting transformants. While various types of markers are available, various negative selection markers are typically utilized, including those which confer resistance to a selection agent that inhibits or kills untransformed cells, such as genes which impart resistance to an antibiotic (such as kanamycin, gentamycin, anamycin, hygromycin and hygrornycinB) or resistance to a herbicide (such as sulfonylurea, gulfosinate, phosphinothricin and glyphosate): Screenable markers include, for example, genes encoding .beta.-glucuronidase (Jefferson, 1987, Plant Mol. Biol. Rep 5: 387-405), genes encoding luciferase (Ow et at, 1986, Science 234: 856-859) and various genes encoding proteins involved in the production or control of anthocyanin pigments (See, for example, U.S. Pat. No. 6,573,432). The *E. coli* glucuronidase gene (gus, gusA or uidA) has become a widely used selection marker in plant transgenics, largely because of the glucuronidase enzyme's stability, high sensitivity and ease of detection (e.g., fluorometric, spectrophotometric, various histochemical methods). Moreover, there is essentially no detectable glucuronidase inmost higher plant species.

Methods of regenerating individual plants from transformed plant cells, tissues or organs are known and are described for numerous plant species.

As an illustration, transformed plantlets (derived from transformed cells or tissues) are cultured in a root-permissive growth medium supplemented with the selective agent used in the transformation strategy (i.e., and antibiotic such as kanamycin). Once rooted, transformed plantlets are then transferred to soil and allowed to grow to maturity. Upon flowering, the mature plants are preferably selfed (self-fertilized), and the resultant seeds harvested and used to grow subsequent generations.

T0 transgenic plants may be used to generate subsequent generations (e.g., T1, T2, etc.) by selfing of primary or secondary transformants, or by sexual crossing of primary or secondary transformants with other plants (transformed or untransformed). Reciprocal crosses were made such that each plant served as the male in a set of crosses and each plant served as the female in a second set of crosses. During the mature plant growth stage, the plants are typically examined for growth phenotype, etc. (see following subsection).

Selection of Growth-Enhanced Transgenic Plants

Transgenic plants may be selected, screened and characterized using standard methodologies. The preferred transgenic plants of the invention will exhibit one or more phenotypic characteristics indicative of enhanced growth and/or other desirable agronomic properties. Transgenic plants are typically regenerated under selective pressure in order to select transformants prior to creating subsequent transgenic plant generations. In addition, the selective pressure used may be employed beyond T0 generations in order to ensure the presence of the desired transgene expression construct or cassette.

T0 transformed plant cells, calli, tissues or plants may be identified and isolated by selecting or screening for the genetic composition of and/or the phenotypic characteristics encoded by marker genes contained in the transgene expression construct used for the transformation. For example, selection may be conducted by growing potentially-transformed plants, tissues or cells in a growth medium containing a repressive amount of antibiotic or herbicide to which the transforming genetic construct can impart resistance. Further, the transformed plant cells, tissues and plants can be identified by screening for the activity of marker genes (i.e., .beta.-glucuronidase) which may be present in the transgene expression construct.

Various physical and biochemical methods may be employed for identifying plants containing the desired transgene expression construct, as is well known. Examples of such methods include Southern blot analysis or various nucleic acid amplification methods (i.e., PCR) for identifying the transgene, transgene expression construct or elements thereof, Northern blotting, S1 RNase protection, reverse transcriptase PCR (RT-PCR) amplification for detecting and determining the RNA transcription products, and protein gel electrophoresis, Western blotting, immunoprecipitation, enzyme immunoassay, enzyme activity and the like may be used for identifying the protein encoded and expressed by the transgene.

It is also noted that FRK and SySy enzymatic activity tests are of the routine work of the person skilled in the art. Such tests may be applied in any arbitrary plant in order to examine whether this plant expresses a native FRK or SuSy.

In another approach, expression levels of genes, proteins and/or metabolic compounds that are known to be modulated by transgene expression in the target plant may be used to identify transformants. In one embodiment of the present invention, increased levels of the phosphorylated fructose may be used to screen for desirable transformants, as exemplified in the Examples. Similarly, increased levels of FRK (fructose phosphorylation) and/or SuSy (UDP dependent sucrose cleavage) activity may be assayed, as exemplified in the Examples.

Promoters for Cloning and Transformation of Fructokinase 1& 2 (FRK1 & FRK2) and Alternatively with Sucrose Synthase (SuSy) into Plants Overexpression of FRK1 (Seq ID. #2) and FRK2 (Seq IDs. #3 & 4) may be made alone or together with SuSy (Seq ID. #1) or with any of the four SuSy genes (SUS1-4 Seq IDs #5-8) isolated by the inventors (Goren et al., 2011), or with any other FRK and SuSy gene. Expression patterns can include limiting the expression of these genes to specific developmental stages such as secondary cell wall development or specific tissues such as xylem and vascular or cambium tissues alone or to overexpression of these genes constitutively in all plant parts. Expression of a gene at a specific developmental stage can be done by developmentally specific promoters. Developmental promoters, for example promoters that are expressed only during secondary wall-thickening and xylem tissue development, are CesA7 promoter (Bosca et al. 2006) (Seq ID #9), PAL2 promoter (Hatton et al. 1995) (Seq ID #10), 4CL-1 promoter (Hauffe et aL 1991) (Seq ID #11), FRA8 promoter (Zhong et al. 2005) (Seq ID #12) and DOT1 promoter (Petricka et al. 2008) (Seq ID #13).

To achieve expression at the xylem developmental stage the nucleic acid encoding a SuSy protein and nucleic acid encoding a FRK1 or other FRK protein were fused to the PAL2 promoter and 4CL-1, respectively, to enable developmental stage controlled co-expression of these two proteins in the plant. Alternatively, constitutive overexpression of SuSy and FRK1 is achieved by fusion of the genes to SvBv promoter (Seq ID #14) and CaMV 35S promoter (Seq ID #15), respectively. Alternatively, the expression of FRK or FRK alone or SuSy alone or both is achieved by control under the constitutive promoter CaMV 35S.

The choice of promoter(s) that can be used depends upon several factors, including, but not limited to, efficiency, selectability, inducibility, desired expression level, and/or preferential cell or tissue expression. It is a routine matter for one of skill in the art to modulate the expression of a sequence by appropriately selecting and positioning promoters and other regulatory regions relative to that sequence. Examples of promoters that can be used are known in the art. Some suitable promoters initiate transcription only, or predominantly, in certain cell types. Methods for identifying and characterizing promoter regions in plant genomic DNA include, for example, those described in Jordano, et al., *Plant Cell* 1:855-866, 1989; Bustos, et al., *Plant Cell* 1:839-854, 1989; Green, et al., *EMBO J.* 7:4035-4044, 1988; Meier et al., *Plant Cell* 3:309-316, 1991; and Zhang et al., *Plant Physiology* 110: 1069-1079, 1996.

Promoters that can be used include those present in plant genomes, as well as promoters from other sources. Exemplary promotes include nopaline synthase (NOS) and octopine synthase (OCS) promoters carried on tumor-inducing plasmids of *Agrobacterium tumefaciens* and CaMV35S promoters from the cauliflower mosaic virus, see, e.g., the promoters described in U.S. Pat. Nos. 5,164,316 and 5,322,938 (incorporated herein by reference). Non-limiting exemplary promoters derived from plant genes are described in U.S. Pat. No. 5,641,876, which describes a rice actin promoter, U.S. Pat. No. 7,151,204, which describes a maize chloroplast aldolase promoter and a maize aldolase (FDA) promoter, and U.S. Patent Application Publication. No. 2003/0131377, which describes a maize nicotianamine synthase promoter (each of which is incorporated herein by reference).

Additional examples of promoters that can be used include ribulose-1,5-bisphosphate carboxylase (RbcS) promoters, such as the RbcS promoter from Eastern larch (*Larix laricina*), the pine cab6 promoter (Yamamoto et al., *Plant Cell Physiol.* 35:773-778, 1994), the Cab-1 gene promoter from wheat (Fejes et al., *Plant Mol. Biol.* 15:921-932, 1990), the CAB-1 promoter from spinach (Lubberstedt et al., *Plant Physiol.* 104:997-1006, 1994), the cab1R promoter from rice (Luan et al., *Plant Cell* 4:971-981, 1992), the pyruvate orthophosphate dikinase (PPDK) promoter from maize (Matsuoka et al., *Proc. Natl. Acad. Sci. U.S.A.* 90:9586-9590, 1993), the tobacco Lhcb1*2 promoter (Cerdan et al., *Plant Mol. Biol.* 33:245-255, 1997), the *Arabidopsis thaliana* SUC2 sucrose-$H^+$ symporter promoter (Truemit et al., *Planta* 196:564-570, 1995), and thylakoid membrane protein promoters from spinach (psaD, psaF, psaE, PC, FNR, atpC, atpD, cab, and rbcS). Additional exemplary promoters that can be used to drive gene transcription in stems, leafs, and green tissue are described in U.S. Patent Application Publication No. 2007/0006346, herein incorporated by reference in its entirety. Additional promoters that result in preferential expression in plant green tissues include those from genes such as *Arabidopsis thaliana* ribulose-1,5-bisphosphate carboxylase (Rubisco) small subunit (Fischhoff et al., *Plant Mol. Biol.* 20:81-93, 1992), aldolase and pyruvate orthophosphate dikinase (PPDK) (Taniguchi et al., *Plant Cell Physiol.* 41(1):42-48, 2000).

In some embodiments, the promoters may be altered to contain one or more enhancers to assist in elevating gene expression. Examples of enhancers that can be used to promote gene expression are known in the art. Enhancers are often are found 5' to the start of transcription in a promoter that functions in eukaryotic cells, but can often be inserted upstream (5') or downstream (3') to the coding sequence. In some instances, these 5' enhancing elements are introns. Non-limiting examples of enhancers include the 5' introns of the rice actin 1 and rice actin 2 genes (see, U.S. Pat. No. 5,641,876), the maize alcohol dehydrogenase gene intron, the maize heat shock protein 70 gene intron (U.S. Pat. No. 5,593,874), and the maize shrunken 1 gene intron.

In some embodiments, the DNA construct or vector can also contain a non-translated leader sequence derived from a virus. Non-limiting examples of non-translated leader sequences that can promote transcription include those from Tobacco Mosaic Virus (TMV, the "W-sequence"), Maize Chlorotic Mottle Virus (MCMV), and Alfalfa Mosaic Virus (AMV) (see, e.g. Gallie et al., *Nucl. Acids Res.* 15: 8693-8711, 1987; Skuzeski et al., *Plant Mol. Biol.* 15: 65-79, 1.990). Additional exemplary leader sequences include: picomavirus leaders, for example, EMCV leader (Encephalomyocarditis 5' noncoding region) (Elroy-Stein et al., *Proc. Natl. Acad. Sci. U.S.A.* 86:6126-6130, 1989); potyvirus leaders, for example, TEV leader (Tobacco Etch Virus); MDMV leader (Maize Dwarf Mosaic Virus); human immunoglobulin heavy-chain binding protein (Bis') leader (Macejak et al., *Nature* 353: 90-94, 1991; untranslated leader from the coat protein mRNA of alfalfa mosaic virus (AMV RNA 4) (Jobling et al., *Nature* 325:622-625, 1987); tobacco mosaic virus leader (TMV) (Gallie et al., *Mol. Biol. RNA*, pages 237-256, 1989); and Maize Chlorotic Mottle Virus leader (MCMV) (Lommel et al., *Virology* 81:382-385, 1991). See also, Della-Cioppa et al., *Plant Physiology* 84:965-968, 1987.

In some embodiments, the DNA constructs or vectors can also contain a 3' element that may contain a polyadenylation signal and/or site. Well-known 3' elements include those from *Agrobacterium tumefaciens* genes, such as nos 3', tm1 3', tmr 3', tins 3', ocs 3', tr7 3', see, e.g., the 3' elements described in U.S. Pat. No. 6,090,627, incorporated herein by reference. The 3' elements can also be derived from plant genes, e.g., the 3' elements from a wheat (*Triticum aesevitum*) heat shock protein 17 (Hsp17 3'), a wheat ubiquitin gene, a wheat fructose-1,6-biphosphatase gene, a rice glutelin gene, a rice lactate dehydrogenase gene, and a rice beta-tubulin gene, all of which are described in U.S. Patent Application Publication No. 2002/0192813 (herein incorporated by reference), the pea (*Pisum sativum*) ribulose biphosphate carboxylase gene (rbs 3'), and the 3' elements from the genes within the host plant. In some embodiments, the 3' element can also contain an appropriate transcriptional terminator, such as a CAMV 35S terminator, the tm1 terminator, the nopaline synthase terminator, and the pea rbcs E9 terminator.

In some embodiments, the DNA constructs or vectors include an inducible promoter. Inducible promoters drive transcription in response to external stimuli, such as chemical agents or environmental stimuli. For example, inducible promoters can confer transcription in response to hormones, such as gibberellic acid or ethylene, or in response to light or drought. Non-limiting examples of inducible promoters are described in Guo et al., *Plant J.* 34:383-392, 2003, and Chen et al., *Plant J.* 36:731-40, 2003.

Methods of Transformation

Transformation techniques for plants are well known in the art and include *Agrobacterium*-based techniques (see, e.g., U.S. Pat. Nos. 5,635,055; 5,824,877; 5,591,616; 5,981,840; and 6,384,301) and techniques that do not require *Agrobacterium*. Non-*Agrobacterium* techniques involve the uptake of exogenous genetic material directly by protoplasts or cells. This can be accomplished by polyethylene glycol (PEG)- or electroporation-mediated uptake (see, e.g., U.S. Pat. No. 5,384,253), particle bombardment-mediated delivery (see, e.g., U.S. Pat. Nos. 5,015,580; 5,550,318; 5,538,880; 6,160,208; 6,399,861; and 6,403,865), protoplast transformation (see, e.g., U.S. Pat. No. 5,508,184) or microinjection. Non-limiting examples of these techniques are described by Paszkowski et al., *EMBO J.* 3:2717-2722, 1984; Potrykus et al., *Mol. Gen. Genet.* 199:169-177, 1985; Reich et al., *Biotechnology* 4:1001-1004, 1986; and Klein et al., *Nature* 327:70-73, 1987. All of which are incorporated herein by reference.

Transformation using *Agrobacterium* has also been described (see, e.g., WO 94/00977 and U.S. Pat. No. 5,591,616, each of which is incorporated herein by reference). In each case, the transformed cells are regenerated to whole plants using standard techniques known in the art. Many vectors are available for transformation using *Agrobacterium tumefaciens*. These vectors typically carry at least one T-DNA border sequence and include vectors such as pBIN19 (Bevan, *Nucl. Acies Res.* 11:369, 1984). The binary vector pCIB10 contains a gene encoding kanamycin resistance for selection in plants and T-DNA right and left border sequences and incorporates sequences from the wide host-range plasmid pRK252 allowing it to replicate in both *E. coli* and *Agrobacterium* (Rothstein et al., *Gene* 53:153-161, 1987). Transformation of the target plant species by recombinant *Agrobacterium* usually involves co-cultivation of the *Agrobacterium* with explants from the plant and follows protocols well known in the art. The transformed tissue is regenerated on selectable medium carrying the antibiotic or herbicide resistance marker present between the binary plasmid T-DNA borders.

Another approach to transforming a plant cell with a gene involves propelling inert or biologically active particles at plant tissues and cells. This technique is disclosed in U.S. Pat. Nos. 4,945,050; 5,036,006; and 5,100,792 (each of which is incorporated herein by reference). Generally, this procedure involves propelling inert or biologically active particles at the cells under conditions effective to penetrate the outer surface of the cell. Gordon-Kamm et al., *Plant Cell* 2:603-618, 1990; Fromm et al., *Biotechnology* 8:833-839, 1990; WO 93/07278; and Koziel et al., *Biotechnology* 11:194-200, 1993 describe exemplary methods of particle bombardment to achieve transformation of plant cells. Exemplary methods of transforming plastids using particle bombardment are described in Svab at al., *Proc. Natl. Acad. Sci. U.S.A.* 90:913-917, 1993; Svab et al., *Proc. Natl. Acad. Sci. U.S.A.* 87:8526-8530, 1990; McBride at al., *Proc. Natl. Acad. Sci. U.S.A.* 91:7301-7305, 1994; Day et al., *Plant Biotech. J.* 9:540-553, 2011.

As noted above, plant cells can also be transformed using PEG or electroporation. Non-limiting examples of techniques that utilize PEG or electroporation to transform plant cells are described in EP 0292435, EP 0392225, and WO 93/07278.

Transient transformation can also be used to express a target gene in plant cell or plant. Non-limiting examples of transient transformation of plant tissues include leaf infiltration, vacuum infiltration, infection with *Agrobacterium*, or bombardment of target tissues with DNA-coated particles.

Plants

In some embodiments, the transgenic plant is a monocot or a dicot. Examples of monocot transgenic plants include, e.g., a meadow grass (blue grass, Poa), a forage grass (e.g., *festuca* and *lolium*), a temperate grass (e.g., *Agrostis*), and cereals (e.g., wheat, oats, rye, barley, rice, sorghum, and maize). Examples of dicot transgenic plants include, e.g., tobacco, legumes lupins, potato, sugar beet, pea, bean, and soybean), and cruciferous plants (family Brassicaceae) (e.g., cauliflower and rape seed). Thus, the transgenic plants provided herein include a broad range of plants, including, but not limited to, species from the genera *Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Pannisetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna*, and *Zea.*

In some embodiments, the transgenic plant is a tree or shrub (e.g., a *eucalyptus* tree or shrub). Non-limiting examples of *eucalyptus* include, without limitation, the following species and crosses thereof: *E. botryoides, E. bridgesiana, E. camaldulensis, E. cinerea, E. globule, E. grandis, E. gunii, E. nicholii, E. pulverulenta, E. robusta, E. rudis, E. saligna, E. Tereticornis, E. Urophilla, E. viminalis, E. dunnii* and a cross hybrids of any of the preceding species especially *Eucalyptus grandis* and *Eucalyptus urophylla*. Poplar species: *P. deltoides, P. tremula, P. alba, P. nigra* (*euramericana*), *P. nigra* (*canadensis*), *P. tremula, P. trichocarpa, P. rouleauiana, P. balsamifera, P. maximowiczii* and crosses thereof. Pine: Genus=*Pinus.*

Isolated Nucleic Acid Molecules

One aspect of the invention pertains to isolated nucleic acid molecules that encode FRK or SuSy proteins, as well as nucleic acid fragments sufficient for use as hybridization probes to identify FRK or SuSy-encoding nucleic acids (e.g., FRK or SuSy mRNA) and fragments for use as PCR primers for the amplification or mutation of CCP nucleic acid molecules. As used herein, the term "nucleic acid molecule" is intended to include DNA molecules (e.g., eDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated FRK or SuSy nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a eDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule encoding the amino acid sequence of SEQ ID NO: 1-8 or a portion thereof, can be isolated using standard molecular biology techniques and the sequence information provided herein. For example, using all or portion of the amino acid sequence of SEQ ID NO: 1-8, as a hybridization probe, FRK or SuSy nucleic acid molecules can be isolated using standard hybridization and cloning techniques (e.g., as described in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989).

Moreover, a nucleic acid encoding all or a portion of the amino acid sequence of SEQ ID NO: 1-8 can be isolated by the polymerase chain reaction (PCR) using synthetic oligonucleotide primers designed based upon the sequence of NO: 1-8, respectively.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis: Furthermore, oligonucleotides corresponding to CCP nucleotide sequences can be prepared by standard synthetic techniques, e.g., using an automated DNA synthesizer.

In still another preferred embodiment, an isolated nucleic acid molecule of the present invention comprises a nucleotide sequence which encodes a protein that is at least about 40%, 50%, 55%, 60%, 65%, 70%, 75%, 80%, 85%, 90%, 95%, 98% or more homologous to the nucleotide sequence (e.g., to the entire length of the nucleotide sequence) that encodes the sequence NO: 1-8, or a portion of any of these nucleotide sequences.

It is well known that undue experimentation is not required for this isolation of the primers or probes. These are trivial methods that can be done for every gene in any species, once one knows the sequences of the gene and choose a reference gene, or just use ribosomal RNA (rRNA) as reference Examples for such primers used in the present invention are: CTCCGTTACATATCTGATCCTT (SEQ ID NO:27) and GACAGCATTGAAGTCACCTT (SEQ ID NO:28) for LeFRK1 (GenBank accession no. U64817), TTGTTGGTGCCCTTCTAACCA (SEQ ID NO:29) and ACGATGTTTCTATGCTCCTCCCT (SEQ ID NO:30) for LeFRK2 (GenBank accession no. U64818), and GACATTTACATGGATGAGAAGAAA (SEQ ID NO:31) and GCTGTGGCACCATCCAATATTT (SEQ ID NO:32) for LeFRK4 (GenBank accession no. AY099454). The tomato actin gene (GenBank accession no. U60482) served as a housekeeping gene for expression normalization. The primers used for actin were CACCATTGGGTCTGAGCGAT (SEQ ID NO:33) and GGGCGACAACCTTGATCTTC (SEQ ID NO:34). The primers for LeFRK3 were GTGGTGCATTGACCGTGATG (SEQ ID NO:35) and GGTCGGATCiGATATTATGCAACTG (SEQ ID NO:36) For LeFRK3 also, the tomato actin gene (GeneBank accession no. U60482) served as a control housekeeping gene for expression normalization.

Primers for sucrose synthase are provided in Planta (2011) 233:1011-1023, incorporated herein by reference. Supplemental Table 1 in Goren et al. 2011 shows PCR, RT-PCR and sequencing primers of SlSUS1, SlSUS3 and SlSUS4.

Activity Assay of Fructokinase

Figure 2:
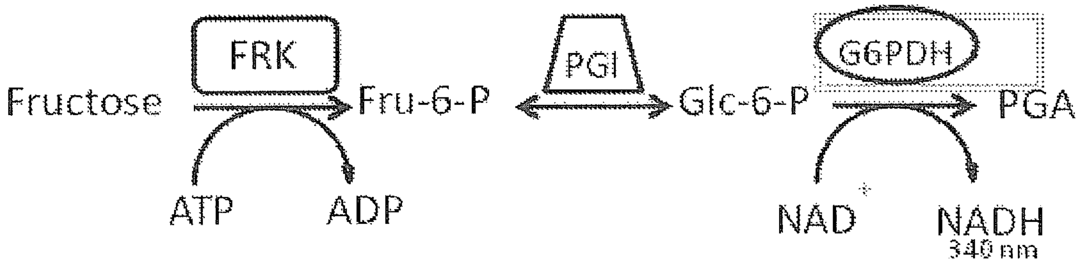
FIG. 2 shows Fructokinase activity assay scheme.

The activity of fructokinase activity is based on the hexose kinase (hexose phosphorylation) assay as described by (Schaffer and Petreikov 1997b). fructokinase activity was measured by an enzyme-linked assay which is based on phosphorylation of fructose (Fru) by fructokinase to get fructose-6-phosphate (Fru-6-P). Fru-6-P is than converted to Glucose-6-phosphate (Glc-6-P) by phosphoglucoisomerase (PGI). Glc-6-P is oxidized to 6-phospho-D-gluconate (PGA) with NAD dependent Glc-6-P dehydrogenase (G6PDH) by reduction of $NAD^+$ to NADH which is continuously monitored by reading at 340 nm (FIG. 2).

Activity Assay for Sucrose Synthase (SuSy)

Activity of disaccharide-cleaving enzymes is assayed in vitro at physiological pH levels in the cleavage direction. Crude protein extract (100 μl) from each sample was added to 400 μl of reaction buffer (0.2M Suc or Tre, 60 mM citrate/phosphate buffer at pH=5 or pH=7) in three independent tubes: one at pH 5, one at pH 7 and a third at pH 7 with 25 μl of 100 mM UDP added. Reaction tubes are incubated at 37° C. for 1 h, then Sumner reagent is added and tubes were incubated at 100° C. for 5 min. A fourth control tube for each sample has crude extract added after Sumner reagent. Reducing monosaccharide in the tubes is assayed by absorption at 550 nm, with the control tube serving as blank for each sample. Acidic invertase activity is calculated from the pH=5 tube, basic invertase from the pH=7 tube, and SuSy activity from the difference between the UDP tube and the pH=7 tube. Activity is normalized to protein amount in each sample.

It is noted that another SuSy enzyme activity, assayed for sucrose cleavage half reaction is based on (Chourey 1981). Protein extracted from plant leaves by the addition of a small portion of SiO2 grains to 0.5 g leaf and grind with a mortal and a pestle with the addition of 1.5 ml of extraction buffer (50 mM HEPES-KOH pH 7.5, 10 mM MgCl2, 1 mM EDTA, 2 mM DTT, 0.1% v/v Triton X-100, 10% v/v glycerol and protease inhibitor). The samples are centrifuged at 15,000 g for 20 min.

Wood Density Measurements

Determination of the basic density of wood chips was according to the standard TAPPI method (Grundelius 1990).

Basic density is defined as the ratio between the oven-dry mass of a woodsample and its green volume.

$$D=M/V$$

Where:

D=basic density, $kg/m^3$.

M=oven dry mass, kg.

V=green volume of a wood sample in equilibrium with surrounding water, $m^3$.

Chips are cut from the bottom of the tree and soaked in water for 72 hours. The green volume of the chips was determined twice, after they were drained and then after they were carefully wiped off by dipping the chips in water bath that was placed on a balance.

$$V=(C-B)/e$$

Whereas:

V=green volume of a wood sample in equilibrium with surrounding water, $m^3$.

C=mass of wood chips and sample basket when immersed in water, g.

B=mass of empty sample basket when immersed in water, g.

e=density of water surrounding sample basket, g/cm3.

Following determination of the green volume, chips were dried at 105° C. till constant weight.

Basic density was calculated.

Fiber and Vessel Characterization

Samples of wild type and transgenic lines were analyzed for the following characteristics:

- Fiber length
- Fiber width
- Diameter of fiber lumen
- Wall thickness
- Vessel length
- Vessel diameter
- Vessel area Wood chips were macerated in hot acetic acid/nitric acid solution (5:1) for 6 hours. After maceration, the samples were thoroughly washed in water and hydrated fibrous material, for at least 24 hours, then subjected to agitation for complete fiber separation. 100 fibers and 100 vessels were measured for each wood sample with video microscope and analyzed with image analyzer.

Cell Wall Composition

The classic 'wet' method for analysis of cell wall constituents is taught by K., G. H., and J., V.-S. P. (1970). Forage Fiber analyses. USDA Agricultural Handbook No. 379. Washington, D.C.: USDA; and AOAC. 1990. Official Methods of Analysis. 15th ed. Assoc. Off Anal. Chem., Arlington, Va. Specifically, examples of 'wet' methods are:

Crude Fiber—AOAC 978.10—this method measures only cellulose and some lignin; ADF-AOAC 973.18—ADF measures cellulose and ALL the lignin and NDF—AOAC 2002.04. NDF is the more complete measure of total fiber since it measures ALL the cellulose, lignin & hemicelluloses.

EXAMPLES

In order to illustrate the invention, the following examples are included. However, it is to be understood that these examples do not limit the invention and are only meant to suggest a method of practicing the invention.

In order to implement some of the embodiments of the invention, five transformation vectors were constructed and are illustrated in FIG. 1:

Vector #1—CaMV 35S promoter::FRK1.
Vector #2—CaMV 355 promoter::FRK2.
Vector #3 CaMV 355 promoter::FRK2 (potato).
Vector #4—CaMV 35S promoter::FRK1_SvBv promoter::SuSy.
Vector #5 4CL-1 promoter::FRK1_PAL2 promoter::SuSy.

Example 1

Increased Growth in FRK-Transformed *Eucalyptus*

A vector designated as Vector 2 illustrated in FIG. 1 was cloned into a plasmid pBI121 (GenBank: AF485783.1) under the CaMV 35S promoter and with the NOS terminator. Transgenic *Eucalyptus* plants are designed to express the exogenous potato FRK2 protein (accession number: Z12823; SEQ ID NO. 4). *Agrobacterium* EAH105 was electrotransformed, selected for 48 hours on kanamycin plates (100 μg/ml), and used for plant transformation. *Eucalyptus* transformation using a protocol essentially as described in Prakash et al., *In Vitro Cell Dev Biol.-Plant* 45:429-434, 2009. Briefly, shoots of *Eucalyptus* were propagated in vitro on Murashige and Skoog (MS) basal salt medium consisting of 3% (w/v) sucrose and 0.8% (w/v) agar.

Plant Growth and Physiological Measurements

Homozygous and heterozygous transgenic and wild type plants were grown in the greenhouse for six months. The canopy height and caliber were monthly measured. The height was determined by measuring the length of the stem of each transgenic plant from the root crown to the top. Dry weight was measured at the end of the experiment.

Plant Protein Extraction

*Eucalyptus* leaves (1 gr) were ground in liquid nitrogen and were homogenized with 4 ml extraction buffer (3 mM DIECA, 1% (w/v) PVPP, 2.5 mM DTT, and 1 mM PMSF at pH 7.6). The mixture was incubated on ice for 60 min and then centrifuged for 30 min at 13,000×g at 4° C. The supernatant was brought to 80% ammonium sulfate saturation and incubated on ice for 15 min. After centrifugation at 12,000×g (4° C.), the pellet was resuspended in 0.5 ml washing buffer (50 mM HEPES, 1 mM EDTA, 1 mM DTT, pH 7.5), desalted on a G-25 fine Sephadex column (55 mm×11 mm), and used as a crude protein extract for subsequent enzymatic analyses.

Gene Expression Analysis

Genomic DNA that was extracted from independent transgenic plants was analyzed by PCR for the presence of FRK2. Positive independent T0 plants were analyzed for FRK2 expression levels. Total RNA was isolated from 200 mg fresh leaves by the EZ-RNA kit (Biological Industries Co., Beit Haemek, Israel) according to the manufacturer's instructions. The RNA was treated with RNase-free DNase and first strand cDNA synthesis was carried out by reverse transcription reaction, FRK2 mRNA levels were analyzed by Real Time PCR using primers FRK2-F (5'-TTGTTGGTGCCCTTCTAACCA-3') (SEQ ID NO:29) and FRK2-R (5-ACGATGTTTCTATGCTCCTCCCT-3') (SEQ ID NO:30), FRK2 gene expression was normalized to the internal control gene histone H4 (AY263810) using primers P91 5'-CCAAGCGGCACAGAAAGGTCC-3 (SEQ ID NO:37) and P92 5'-CCGAAGCCATACAGGGTCCT 3' (SEQ ID NO:38).

Activity Assay of FRK in *Eucalyptus*

Fructokinase activity is measured by spectrophotometer with protein extracts using an enzyme linked assay. PGI enzyme converts F6P to glucose-6-phosphate (G6P) and G6P-dehydrogenase enzyme transfers hydrogen from G6P to NAD, converting it to NADH. The spectrophotometer reads the amount of NADH. The assay was conducted in 0.5 ml reaction mixture that contained 100 μl of crude protein extract, 30 mM HEPES (pH 7.6), 9 mM KCl, 1 M MgCl2, 1 mM ATP, 1 mM NAD, 0.5 unit PGI (type III), 0.5 unit NAD-dependent G-6-P DH. The reaction was initiated after the addition of 1 or 10 mM fructose. Enzyme activity (mg/ml) was examined at 37° C. and A340 nm was monitored continuously (Petreikov and Schaffer, 1997a).

Figure 3:
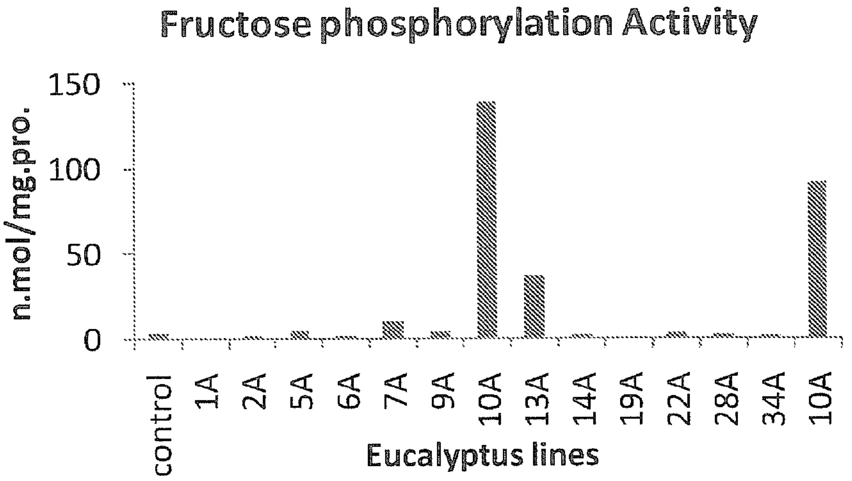
FIG. 3 shows FRK2 phosphorylation activity in wild-type and different transgenic *eucalyptus* lines.

As described above, the 35S::FRK2 construct was introduced into *Eucalyptus* tree by *Agrobacterium* mediated transformation and total of 14 transformed lines were obtained. In order to evaluate the activity of the transgene, the inventors analyzed FRK2 protein by extracting protein from fresh tissue and measuring activity. Line 10 showed the highest FRK2 activity, followed by 13A, 7A and 5A as expected with plant transformation experiments in which positioning effects, copy number, and other factors routinely provide varied results (FIG. 3). FIG. 3 shows FRK2 phosphorylation activity. Activity was measured in crude protein extracts of wild-type and different transgenic *eucalyptus* lines, with 10 mM fructose. Control, wild-type. Line 10A shows the strongest activity.

Figure 4:
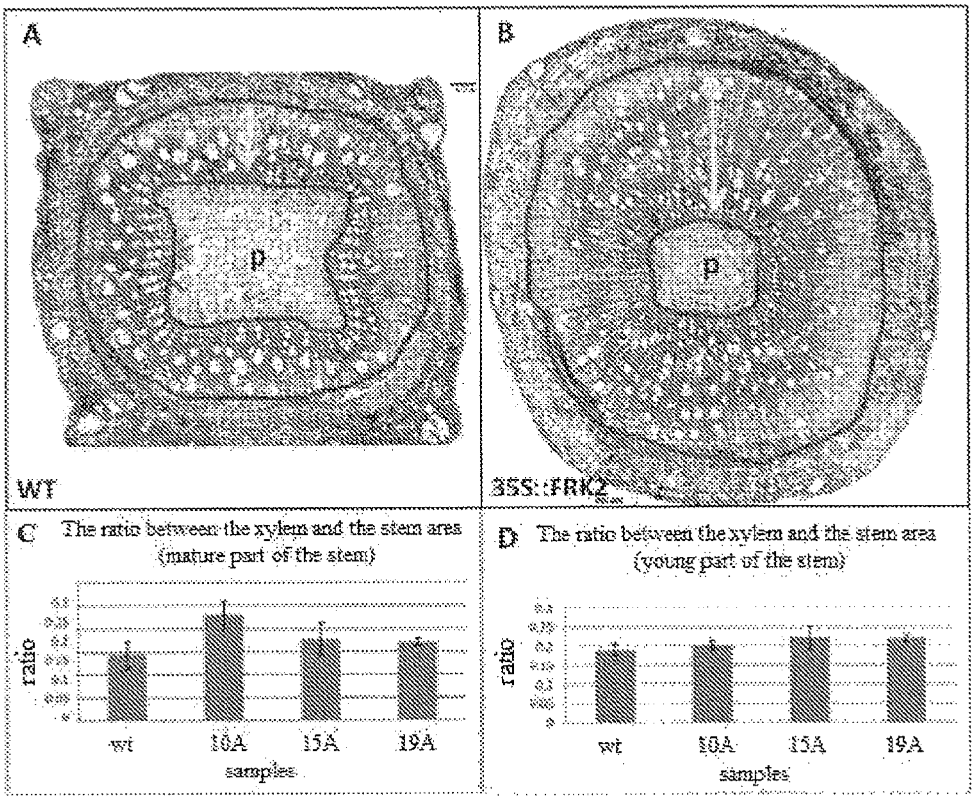
FIGS. 4A and 4B show micrographs of cross sections of *Eucalyptus* stem stained with safranin fast-green.
FIGS. 4C and 4D show the ratio between the xylem area and the total stem area.

Overexpression of FRK2 in *Eucalyptus* Increases Xylem Relative Area in the Stem The effect of 35S::FRK2 on vasculature development was analyzed by calculating the relative xylem area in cross sections that were taken from mature and young *eucalyptus* stems. While lines 15A and 19A showed relative xylem area similar to wild type in both mature and young stems, line 10A showed significantly higher ratio in mature stem relative to wild type (FIG. 4). Thus, 35S::FRK2 expression facilitates xylem formation.

FIG. 4 shows the effect of 35S::FRK2 on *Eucalyptus* vasculature. In A and B, Micrographs of cross sections of *Eucalyptus* stem stained with safranin fast-green. The outer and inner xylem borders are marked in red and possess the xylem (yellow double arrow). While the outer border indicates the cambium fraction, the inner xylem borders encompasses the pith (p). The ratio between the xylem and the total stem area is higher in 35S::FRK2 stem (B) relative to wild type (A). In C and D, The ratio between the xylem area and the total stem area, in mature (C) and young (D) stems, was calculated for cross sections of wild type and transgenic *Eucalyptus* lines. Line 10A shows the highest ratio between the xylem and the total stein area in mature stem (C) but not in young stem sections (D).

Anatomical Characterization—Histological Analysis

For analyzing the structure of the vascular system, stem tissues were fixed in FAA (1.85% formaldehyde, 5% glacial acetic acid, 63% ethanol,), dehydrated through an ethanol series (70, 80, 90, and 100%, 30 min each), embedded in paraffin, sectioned in a microtome (Leica RM2245), and stained with Safranin-O/Fast-green (Johansen 1940). The sectioned material was observed in a Leica IM1000 microscope, and digital images were taken with a CCD camera DC2000 (Leica, Germany).

Carbon Partitioning Analysis

The relative amounts of lignin/cellulose/hemicellulose vs. starch in the transformed plants are examined. Cell wall material (CWM) was obtained as previously described by Foster et al. (Foster et al. 2010) with minor modifications; mature inflorescence stems were air dried, ground and screened through 40 mesh sieve. Ground tissue was washed in 70% ethanol, vortexes and pelleted by centrifugation at 12,000 g for 10 min. The pellet was washed with chloroform:manethanol (1□1, v/v), vortexed, and centrifuged at 12,000 g for 10 min. The pellet was washed with acetone and, after centrifugation at 12,000 g for 10 min, was air-dried and weighed. Starch content was removed by incubation of the dried pellet with The dried powder was gelatinized in NaAc buffer (100 mM pH 5) for 20 min at 80° C. and freed of starch by amylase and pullulanase incubation. The pellet was washed with water and acetone and then air dried.

Cell Wall Analysis

Cellulose was quantified in CWM according to the Updegraff method (Updegraff 1969), the resulted cellulose was hydrolyzed by Saeman hydrolysis and quantified by the anthrone method (Scott Jr and Melvin 1953).

Monosaccharides composition of CWM was determined by two-stage sulfuric acid hydrolysis (Sluiter et aL 2004). After neutralization, monosaccharides (arabinose, galactose, glucose, mannose and xylose) in the hydrolyzates were were analyzed at 80° C. on a HPLC system equipped with PhenomenexRezex RPM-monosaccharide Pb$^{2}$ (8%) column (300 mm×7.80 mm) by RI detector using a gradient mobile phase of HPLC grade water. The lignin content of stems was determined by the acetyl bromide method (Fukushima and Hatfield 2001). Lignin composition was determined by thioacidolysis according to a method previously described (Robinson and Mansfield 2009). The resulted products were trimethylsilylated and then identified by GC/MS.

Figure 6:
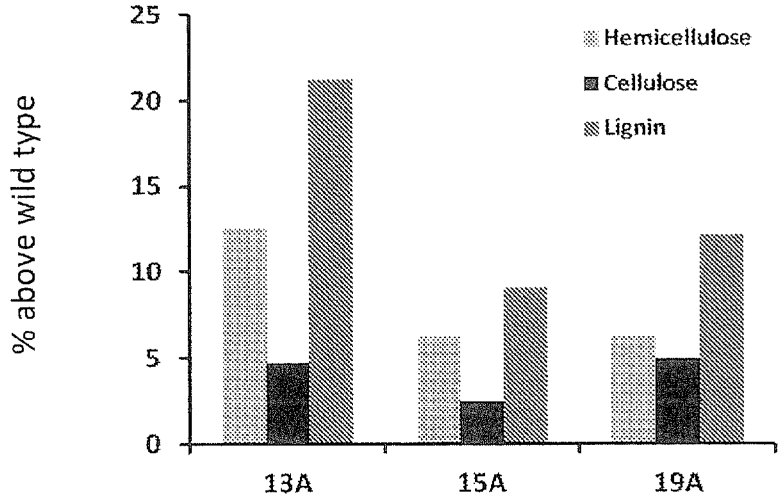
FIG. 6 shows the increased percentage of cell wall content in 35S::FRK2 *Eucalyptus* stem compare to the control plants.

FIG. 6 shows alterations of cell wall constituents by FRK2 expression in *Eucalyptus*. Cell wall components percentage was calculated relative to wild type in three different transgenic lines, 13A, 15A and 19A.

Example 2

Increased Growth in FRK & SuSy—Double Trangenic *Eucalyptus*

Transgenic *Eucalyptus* plants are produced as in Example 1 but with Vector 4 illustrated in FIG. 1 and shown in SEQ ID NO. 18 is cloned. In this expression vector, fructokinase 1 is under 355 promoter and SuSy under SvBv promoter. AGS terminator is used for fructokinase and NOS terminator for SuSy. Source for Fructokinase 1 (FRK1) is tomato, optimized for *Eucalyptus* expression. Source for the SuSy is cotton optimized for *eucalyptus* expression. FRK1 and SuSy mRNA levels were analyzed by Real Time PCR using the following primers: primers for FRK1 are: CTCCGTTACATATCTGATCCTT (SEQ ID NO:27); Rev: GACAGCATTGAAGTCACCTT (SEQ ID NO:28) (GenBank accession no. U64817). Primers for the *Eucalyptus* optimized SuSy from cotton are: Fw: TTGCATTGGCCGTGAG (SEQ ID NO:39); Rev: GCAAGTCCTCAATTTCTGGG (SEQ ID NO:40).

Activity Assay for Sucrose Synthase

Activity of disaccharide-cleaving enzymes was assayed in vitro at physiological pH levels in the cleavage direction, as described above. The reaction mixture for sucrose cleavage consisted of 64 μmoles MES buffer (pH 6.0), 125 μmoles sucrose, 0.5 μmoles uridine diphosphate (UDP), and 1, 5 or 10 μl of the crude enzyme preparation from various genotypes in a total volume of 0.4 ml in vials. Vials containing identical contents but lacking UDP constituted the controls. The tubes were incubated in a 30° C. water bath for 15 minutes and the reaction was terminated by adding DNS for measuring reducing sugars.

Soluble Carbohydrates and Starch

Sugars were extracted from stem segments by resuspending the segments in 5 ml of 80% ethanol in an 80° C. water bath for 60 min. This procedure was repeated twice. The ethanol solutions were combined and completely evaporated at 40° C. with the aid of continuous ventilation. The dried sugars were dissolved in 1 ml distilled water and were stored in −80° C. Sucrose, fructose, and glucose contents were determined by HPLC. The HPLC system consisted of a Shimadzu LC-10AT solvent delivery system and detection was by a Shimadzu RID10Arefractive index detector. Separation was carried out on an Alltech 700 CH Carbohydrate Column (Alltech, Deer-Weld, Ill., USA), maintained at 90° C. with a Xow rate of 0.5 ml/min, according to manufacturer's recommendations. The ethanol-insoluble residue was used to determine the concentration of starch in the grafted segment of the stem. Starch digestion was carried out by incubating and autoclaving samples with 6 ml water, and then adding 4 ml of buffer containing 200 units of amyloglucosidase and incubating overnight at 55° C. (Dinar et al. 1983). The amount of released glucose was determined using Sumner reagent. Optical density was determined at 550 nm. (Damari-Weissler, Rachamilevitch, Aloni, German, Cohen, Zwieniecki, Michele Holbrook and Granot 2009)

Example 3

Increased Growth in FRK & SuSy—Transformed *Eucalyptus*

Transgenic *Eucalyptus* plants are produced as in Example 2 but with Vector 5 illustrated in FIG. 1, and shown in SEQ ID NO. 19, is cloned. In this expression vector, fructokinase 1 is under 4CL-1 promoter and SuSy is under PAL2 promoter. AGS terminator is used for fructokinase and NOS terminator for SuSy. Source for Fructokinase 1 is tomato, optimized for *eucalyptus* expression. Source for the SuSy is cotton optimized for *eucalyptus* expression. FRK1 and SuSy mRNA levels were analyzed by Real Time PCR using primers as in Example 2.

Example 4

Increased Cell Wall Content in FRK-Transformed Tomato

Tomato Transformation and Selection of Transgenic Lines

FRK2 was introduced in sense and antisense orientation under the control of the cauliflower mosaic virus 35 promoter into the binary vector pBI121 containing the neomycin phosphotransferaseII gene (nptII) as a selectable marker. Transformation was done on MP-1, a tomato (*L. esculentum*) line known for its high transformation efficiency, essentially, as described by McCormick (McCormick 1991). T0 and T1 independent transgenic plants were analyzed by PCR and by DNA gel blotting for the presence and copy number of FRK2. FRK2 hemizygous and homozygous plants were identified among T1 seeds following kanamycin resistant segregation analysis of nptII, which is linked to FRK2. Two plants, FK3 and FK29, out of 15 independent T0 regenerants with sense-FRK2, were chosen based on their high expression and activity levels of FRK2 in leaves and fruits. Among the antisense-FRK2 transformed plants, only one plant out of 12 independent transformations (FK-3a,5) showed remarkable suppression of LeFRK2 expression and activity (German, Dai, Matsevitz, Hanael, Petreikov, Bernstein, Ioffe, Shahak, Schaffer and Granot 2003).

Modified Expression of FRK2 Affects Cell Wall Content

To examine the effect of FRK2 suppression or increased expression of FRK2 on cell wall Applicants analyzed total cell wall and cell wall constituents (cellulose, hemicellulose and lignin) in stems of FRK2-antisense transgenic tomato plants that had lower expression and activity of FRK2 compared to wild-type plants, and in transgenic tomato plants expressing potato FRK2 (accession number: Z12823) in the sense (coding) orientation (FRK2-sense plants) that had higher expression and activity of FRK2 compared to wild-type plants (FIG. 5A).

Cell Wall Content Analysis

Total cell wall, cellulose and lignin content in the stem were directly related to FRK2 expression and activity. The harvested plant material of 3 grams was oven-dried at 65° C. and was grounded to pass a 1-mm sieve. The samples were analyzed by the AOAC (1995) procedure no. 989.03, in which NDF and ADF were assayed according to Goering and Van. Soest (1970). The in vitro dry matter digestibility of (IVDMD) was evaluated according to Tilley and Terry (1963).

While FRK2-antisense plants had over 20% lower total cell wall and cellulose content compared to wild-type stem, sense plants had significantly higher total cell wall, cellulose and lignin content in stems (FIG. 5B).

Figure 5:
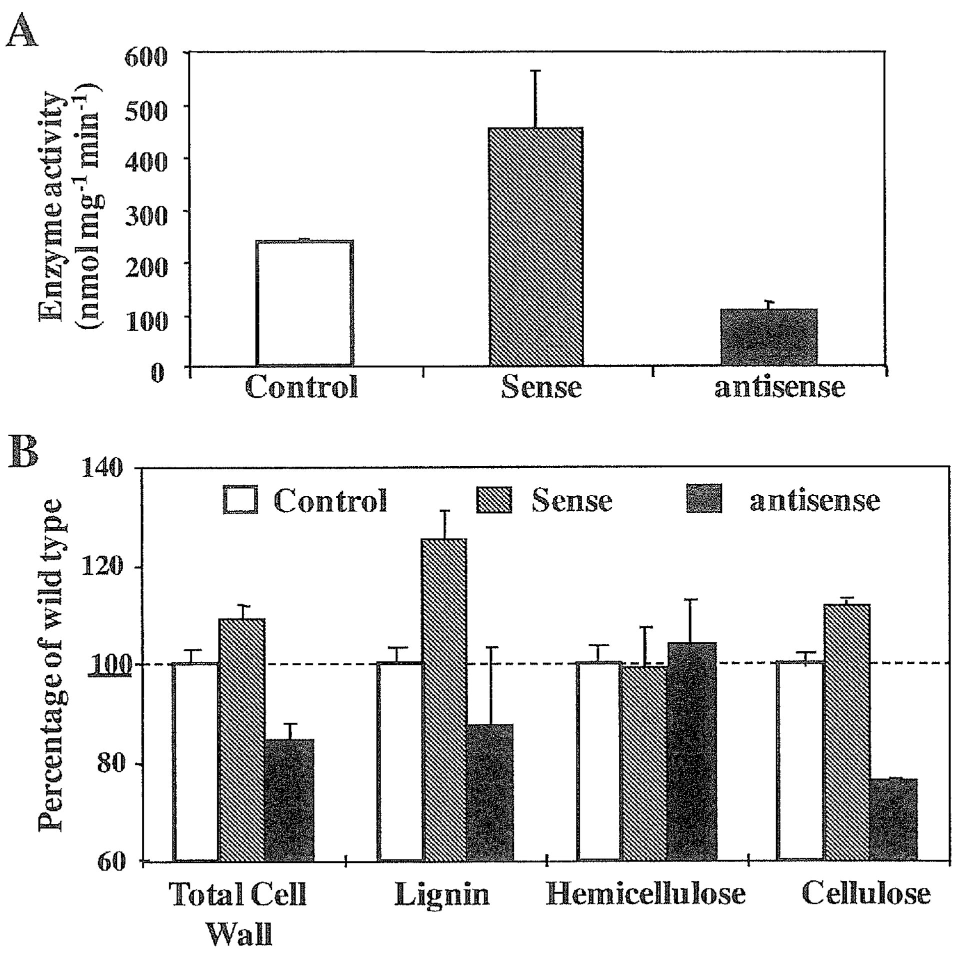
FIG. 5A shows FRK2 activity in wild-type (control), sense-FRK2 plants and antisense-FRK2 plants.
FIG. 5B shows percentages of cell wall constituents in wild-type (control), sense-FRK2 plants (sense) and antisense-FRK2 plants (antisense).

FIG. 5 shows alteration of cell wall constituents by FRK2 expression. In FIG. 5A, FRK2 activity in wild-type (control), sense-FRK2 plants and antisense-FRK2 plants. Enzyme activity was measured on plant protein extract. In FIG. 5B, percentages of cell wall constituents in wild-type (control), sense-FRK2 plants (sense) and antisense-FRK2 plants (antisense).

All publications, patents, and patent applications cited in this specification are herein incorporated by reference as if each individual publication or patent application were specifically and individually indicated to be incorporated by reference.

REFERENCES

Bosco, S., Barton, C. J., Taylor, N. G., Ryden, P., Neumetzler, L., Pauly, M., Roberts, K. and Seifert, G. J. (2006) Interactions between MUR10/CesA7-dependent secondary cellulose biosynthesis and primary cell wall structure. *Plant Physiol*, 142, 1353-1363.

Chourey, P. S. (1981) Genetic control of sucrose synthetase in maize endosperm. *Molecular and General Genetics MGG*, 184, 372-376.

Dai, N., German, M. A., Matsevitz, T., Hanael, R., Swartzberg, D., Yeselson, V., Petreikov, M., Schaffer, A. A. and Granot, D. (2002) LeFRK2, the gene encoding the major fructokinase in tomato fruits, is not required for starch biosynthesis in developing fruits. *Plant Science*, 162, 423-430.

Dai, N., Schaffer, A., Petreikov, M. and Granot, D. (1997) Potato (*Solanum tuberosum* L.) fructokinase expressed in yeast exhibits inhibition by fructose of both in vitro enzyme activity and rate of cell proliferation. *Plant Science*, 128, 191-197.

Damari-Weissler, H., Kandel-Kfir, M., Gidoni, D., Mett, A., Belausov, E. and Granot, D. (2006) Evidence for intracellular spatial separation of hexokinases and fructokinases in tomato plants. *Planta*, 224, 1495-1502.

Damari-Weissler, H., Rachamilevitch, S., Aloni, R., German, M. A., Cohen, S., Zwieniecki, M. A., Michele Holbrook, N. and Granot, D. (2009) LeFRK2 is required for phloem and xylem differentiation and the transport of both sugar and water. *Planta*, 230, 795-805.

Foster, C. E., Martin, T. M. and Pauly, M. (2010) Comprehensive compositional analysis of plant cell walls (Lignocellulosic biomass) part I: lignin. *J Vis Exp.*

Fukushima, R. S. and Hatfield, R. D. (2001) Extraction and isolation of lignin for utilization as a standard to determine lignin concentration using the acetyl bromide spectrophotometric method. *J Agric Food Chem*, 49, 3133-3139.

German, M. A., Asher, I., Petreikov, M., Dai, N., Schaffer, A. A. and Granot, D. (2004) Cloning, expression and characterization of LeFRK3, the fourth tomato (*Lycopersicon esculentum* Mill.) gene encoding fructokinase. *Plant Science*, 166, 285-291.

German, M. A., Dai, N., Chmelnitsky, L., Sobolev, I., Salts, Y., Barg, R., Schaffer, A. A. and Granot, D. (2002) LeFRK4, a novel tomato (*Lycopersicon esculentum* Mill.) fructokinase specifically expressed in stamens. *Plant Science,* 163, 607-613.

German, M. A., Dai, N., Matsevitz, T., Hanael, R., Petreikov, M., Bernstein, N., Ioffe, M., Shahak, Y., Schaffer, A. A. and Granot, D. (2003) Suppression of fructokinase encoded by LeFRK2 in tomato stem inhibits growth and causes wilting of young leaves. *Plant J,* 34, 837-846.

Goren, S., Huber, S. C. and Granot, D. (2011) Comparison of a novel tomato sucrose synthase, SlSUS4, with previously described SlSUS isoforms reveals distinct sequence features and differential expression patterns in association with stem maturation. *Planta,* 233, 1011-1023.

Granot, D. (2007) Role of tomato hexose kinases. *Functional Plant Biology,* 34, 564-570.

Grundelius, R. (1990) Determining the basic density of wood chips. *Tappi journal,* 73, 183-189.

Hatton, D., Sablowski, R., Yung, M. H., Smith, C., Schuch, W. and Bevan, M. (1995) Two classes of cis sequences contribute to tissue-specific expression of a PAL2 promoter in transgenic tobacco. *The Plant Journal,* 7, 859-876.

Hauffe, K. D., Paszkowski, U., Schulze-Lefert, P., Hahlbrock, K., Dana J. L. and Douglas, C. J. (1991) A parsley 4CL-1 promoter fragment specifies complex expression patterns in transgenic tobacco. *The Plant Cell Online,* 3, 435.

Johansen, D. A. (1940) *Plant Microtechniques* New York: McGraw-Hill Book.

Kanayania, Y., Dai, N., Granot, D., Petreikov, M., Schaffer, A. and Bennett, A. B. (1997) Divergent fructokinase genes are differentially expressed in tomato. *Plant Physiol,* 113, 1379-1384.

Kanayama, Y., Granot, D., Dai, N., Petreikov, M., Schaffer, A., Powell, A. and Bennett, A. B. (1998) Tomato fructokinases exhibit differential expression and substrate regulation. *Plant Physiol,* 117, 85-90.

Koch, K. (2004) Sucrose metabolism: regulatory mechanisms and pivotal roles in sugar sensing and plant development. *Curr Opin Plant Biol,* 7, 235-246.

McCormick, S. (1991) Transformation of tomato with *Agrobacterium tumefaciens. Plant Tiss. Cult. Man.,* 6, 1-9.

Odanaka, S., Bennett, A. B. and Kanayama, Y. (2002) Distinct physiological roles of fructokinase isozymes revealed by gene-specific suppression of frk1 and frk2 expression in tomato. *Plant Physiol,* 129, 1119-1126.

Petreikov, M., Dai, N., Granot, D. and Schaffer, A. A. (2001) Characterization of native and yeast-expressed tomato fruit fructokinase enzymes. *Phytochemistry,* 58, 841-847.

Petricka, J. J., Clay, N. K. and Nelson, T. M. (2008) Vein patterning screens and the defectively organized tributaries mutants in *Arabidopsis thaliana. Plant J,* 56, 251-263.

Robinson, A. R. and Mansfield, S. D. (2009) Rapid analysis of poplar lignin monomer composition by a streamlined thioacidolysis procedure and near-infrared reflectance-based prediction modeling. *Plant J,* 58, 706-714.

Schaffer, A. A. and Petreikov, M. (1997a) Inhibition of fructokinase and sucrose synthase by cytosolic levels of fructose in young tomato fruit undergoing transient starch synthesis. *Physiologia Plantarum,* 101, 800-806.

Schaffer, A. A. and Petreikov, M. (1997b) Sucrose-to-Starch Metabolism in Tomato Fruit Undergoing Transient Starch Accumulation, *Plant Physiol,* 113, 739-746, Scott Jr, T. A. and Melvin, E. H. (1953) Determination of dextran with anthrone. *Analytical Chemistry,* 25, 1656-1661.

Sluiter, A., flames, B., Ruiz, R., Scarlata, C., Sluiter, J., Templeton, D. and Crocker, D. (2004) Determination of structural carbohydrates and lignin in biomass. *NREL, Golden, Co.*

Updegraff, D. M. (1969) Semimicro determination of cellulose in biological materials. *Anal Biochem,* 32, 420-424.

Zhong, R, Peña, M. J., Thou, G. K., Nairn, C. J., Wood-Jones, A., Richardson, E. A., Morrison, W. H., Darvill, A. G., York, W. S. and Ye, Z. H. (2005) *Arabidopsis* fragile fiber8, which encodes a putative glucuronyltransferase, is essential for normal secondary wall synthesis. *Plant Cell,* 17, 3390-3408.

AOAC. (1995). Official Methods of Analysis. (Arlington, Va.).

Goering, H. K., and Van Soest, P. J. (1970). Forage fiber analysis (apparatus, reagents, procedures and some applications). In Agriculture Handbook (Washington, USA: Agriculture Research Service, United States Department of Agriculture).

Tilley, J. M. A., and Terry, R. A. (1963). A two-stage technique for the in vitro digestion of forage crops. Grass Forage Sci 18, 104-111.

The invention claimed is:

1. A nucleic acid construct comprising: a first nucleic acid that encodes a fructokinase (FRK) protein; and a second nucleic acid that encodes a sucrose synthase (SuSy) protein, wherein each of said nucleic acids is operatively linked to a plant-functional promoter, wherein said construct has the nucleic acid sequence of SEQ ID NO. 18.

2. A nucleic acid construct comprising: a first nucleic acid that encodes a fructokinase (FRK) protein; and a second nucleic acid that encodes a sucrose synthase (SuSy) protein, wherein each of said nucleic acids is operatively linked to a plant-functional promoter, wherein said construct has the nucleic acid sequence of SEQ ID NO. 19.

3. A nucleic acid construct according to claim 1, wherein said construct imparts to transgenic plants containing said construct, a feature selected from a group consisting of: increased cell wall content, higher growth rate and increased biomass relative to the same feature in a corresponding wild-type plant.

4. A nucleic acid construct according to claim 1, wherein said construct imparts to transgenic plants containing said construct, increased cell wall content relative to cell wall content in a corresponding wild-type plant.

5. A vector comprising the nucleic acid construct of claim 1.

6. A plant containing the vector of claim 5.

7. A vector comprising the construct of claim 2.

8. A plant containing the vector of claim 7.

9. A nucleic acid construct according to claim 2, wherein said construct imparts to transgenic plants containing said construct, a feature selected from a group consisting of: increased cell wall content, higher growth rate and increased biomass relative to the same feature in a corresponding wild-type plant.

10. A nucleic acid construct according to claim 2, wherein said construct imparts to transgenic plants containing said construct, increased cell wall content relative to cell wall content in a corresponding wild-type plant.

* * * * *